(12) United States Patent
Harada et al.

(10) Patent No.: US 6,750,232 B2
(45) Date of Patent: Jun. 15, 2004

(54) 2-AMINOPYRIDINE COMPOUNDS AND USE THEREOF AS DRUGS

(75) Inventors: Hitoshi Harada, Ibaraki (JP); Osamu Asano, Ibaraki (JP); Shuhei Miyazawa, Ibaraki (JP); Masato Ueda, Ibaraki (JP); Masahiro Yasuda, Ibaraki (JP); Nobuyuki Yasuda, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/333,689

(22) PCT Filed: Aug. 9, 2001

(86) PCT No.: PCT/JP01/06870

§ 371 (c)(1),
(2), (4) Date: Jan. 23, 2003

(87) PCT Pub. No.: WO02/14282

PCT Pub. Date: Feb. 21, 2002

(65) Prior Publication Data

US 2004/0006082 A1 Jan. 8, 2004

(30) Foreign Application Priority Data

Aug. 11, 2000 (JP) ......................................... 2000-245056

(51) Int. Cl.⁷ ....................... C07D 401/02; A61K 31/44
(52) U.S. Cl. .................. 514/334; 514/344; 514/352; 546/257; 546/289; 546/309; 546/310
(58) Field of Search ............................. 546/257, 289, 546/309, 310; 514/334, 344, 352

(56) References Cited

U.S. PATENT DOCUMENTS

| | | | |
|---|---|---|---|
| 5,686,470 A | 11/1997 | Weier et al. | 514/345 |
| 5,916,905 A | 6/1999 | Weier et al. | 514/345 |
| 6,030,969 A | 2/2000 | Bhagwat et al. | 514/345 |

FOREIGN PATENT DOCUMENTS

| | | |
|---|---|---|
| DE | 41 17 802 A1 | 12/1992 |
| JP | 11-263789 A | 9/1999 |
| WO | WO 96/24584 A1 | 8/1996 |
| WO | WO 99/21555 A2 | 5/1999 |

OTHER PUBLICATIONS

Konakahara, Takeo, et al. HETEROCYCLES, vol. 55, No. 2, pp. 313–322, Feb. 1, 2001.
Quinteiro, Margarita, et al. HETEROCYCLES, vol. 24, No. 6, pp. 1675–1682, 1986.
Hagen, Voler, et al. Chemical Abstracts, vol. 115, Abstract No. 115:92087, 1991.
Troschuetz, Reinhard, et al. Chemical Abstracts, vol. 121, Abstract No. 121:35267, 1994.
Troschuetz, Reinhard, et al. Arch. Pharm., vol. 327, No. 1, pp. 33–40, 1994.
El–Farargy, Ahmed, et al. Chemical Abstracts, vol. 120, Abstract No. 120:191650, 1994.
El–Farargy, Ahmed, et al. Collect. Czech. Chem. Commun., vol. 58, No. 8, pp. 1937–1943, 1993.
Van Calker, Dietrich, et al. Journal of Neurochemistry, vol. 33, pp. 999–1005, 1993.
Bruns, Robert F., et al. Molecular Pharmacology, vol. 29, pp. 331–346, Jan. 13, 1986.
Wan, W., et al. Journal of Neurochemistry, vol. 55, pp. 1763–1771, 1990.
Feoktistov, Igor, et al. J. Clin. Invest., vol. 96, pp. 1979–1986, Oct. 1995.
Dixon, Alistair, et al. British Journal of Pharmacology, vol. 188, pp. 1461–1468, 1999.
Peachey, Julie A., et al. Naunyn–Schmiedeberg's Arch. Pharmacol., vol. 359, pp. 140–146, 1999.
Kadowaki, Makoto, et al. British Journal of Pharmacology, vol. 129, pp. 871–876, 2000.
De Zwart, Maarten, et al. Drug Development Research, vol. 48, pp. 95–103, 1999.
Kim, Yong–Chul, et al. Journal of Medical Chemistry, vol. 43, pp. 1165–1172, 2000.

*Primary Examiner*—Zinna Northington Davis
(74) *Attorney, Agent, or Firm*—Birch, Stewart, Kolasch & Birch, LLP

(57) ABSTRACT

A class of substituted compounds is described for use in treating inflammation and inflammation-related disorders. Compounds of particular interest are defined by formula (II), wherein $R^1$ is selected from hydrido, halo, alkoxy, aryl, alkylthio, alkylamino, aralkoxy, azido and alkenyloxy; wherein $R^2$ is selected from hydrido, cyano, hydroxyalkyl, haloalkyl, aminoalkyl, alkylaminoalkyl, alkylcarbonyloxyalkyl, aminocarbonyl and alkylcarbonylaminoalkyl; and wherein $R^5$ and $R^6$ are one more radicals independently selected from halo, alkylsulfonyl, aminosulfonyl, alkoxy and alkylthio; provided one of $R^5$ and $R^6$ is substituted with alkysulfonyl, aminosulfonyl, or haloalkylsulfonyl; or a pharmaceutically-acceptable salt thereof.

(II)

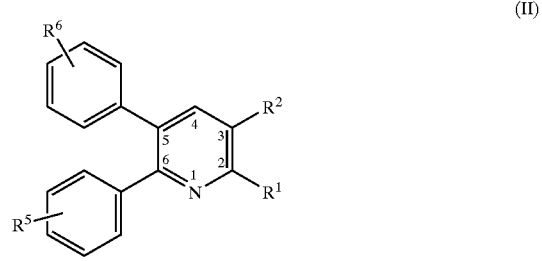

39 Claims, No Drawings

2-AMINOPYRIDINE COMPOUNDS AND USE THEREOF AS DRUGS

This application is the national phase under 35 U.S.C. §371 of PCT International Application No. PCT/JP01/06870 which has an International filing date of Aug. 9, 2001, which designated the United States of America.

TECHNICAL FIELD

The present invention relates to a novel 2-aminopyridine compound, a process for producing it, and use thereof as a medicament.

PRIOR ART

Adenosine is an important regulatory factor involved in various intracellular metabolisms such as regulation of energy levels and cAMP levels in the living body, opening and closing calcium channels, and inflow of calcium ions into cells, and can exhibit its physiological activity by interaction with G protein-conjugated receptors on the surface of a cell. Adenosine receptors were at first classified into 2 classes, that is, $A_1$ receptor and $A_2$ receptor on the basis of their participation in adenylate cyclase (J. Neurochem., 33, 999–1003 (1979)), and thereafter, the $A_2$ receptor was classified into 2 subtypes, that is, $A_{2A}$ and $A_{2B}$ on the basis of their affinity for NECA and CGS-21680 (Mol. Pharmacol., 29, 331–346 (1986); J. Neurochem., 55, 1763–1771 (1990)) which are adenosine $A_2$ receptor agonists. Thus, 4 receptor subtypes, $A_1$, $A_2$ ($A_{2A}$, $A_{2B}$) and $A_3$, have been identified until now. The $A_1$ receptor is a protein conjugated with $G_{i/o}$ family protein. By binding of ligands, it inhibits adenylate cyclase to suppress cAMP levels and activates phospholipase C (PLC) to promote production of inositol-1,4,5-triphosphate ($IP_3$) and release of intracellular calcium ions. It is known that similar to the $A_1$ receptor, the $A_3$ receptor is a receptor suppressing cAMP levels and activating PLC to promote production of $IP_3$ and release of intracellular calcium ions. On the other hand, the $A_{2A}$ and $A_{2B}$ receptors are those activating adenylate cyclase and promoting production of cAMP levels. It is also reported that $A_{2B}$ is conjugated with PLC via $G_q/G_{11}$ protein, and promotes production of $IP_3$ levels and inflow of calcium ions into cells (din. Invest., 96, 1979–1986 (1995)). These subtypes are different from one another in their distribution in tissues; that is, the $A_1$ receptor occurs relatively abundantly in the heart, aorta, bladder, etc., the $A_{2A}$ receptor in the eyeballs, skeletal muscles, etc., and the $A_3$ receptor in the spleen, uterus, prostate, etc., while the $A_{2B}$ receptor occurs relatively abundantly in proximity to the large intestine and in the eyeballs, lung, uterus and bladder (Br. J. Pharmacol., 118, 1461–1468 (1996)). The reason that adenosine receptor subtypes can exhibit their inherent functions is attributable to a difference in their distribution in tissues, a difference in topical adenosine levels and a difference in affinity of each subtype for ligands. Adenosine is involved in various physiological functions such as platelet agglutination, heartbeats, contraction of smooth muscles, inflammations, release of neurotransmitters, neurotransmission, release of hormones, cellular differentiation, growth of cells, death of cells, biosynthesis of DNA, etc., thus suggesting the relationship of adenosine with diseases in the neutral nerves, cardiovascular diseases, inflammatory diseases, diseases in the respiratory organs, immune diseases, etc., so usefulness of adenosine receptor agonists/antagonists against these diseases is expected. On one hand, important reports have been made in recent years on the relationship between the adenosine $A_2$ receptor and the intestinal tracts. For example, it is reported that a relaxing action on colon longitudinal muscles is mediated by $A_2$ receptor (Naunyn-Schmiedeberg's Arch. Pharmacol., 359, 140–146 (1999)), and that the relaxing action of adenosine on contraction of guinea pig distant colon longitudinal muscles is mediated by $A_1$ receptor and $A_{2b}$ receptor in longitudinal muscles (Br. J. Pharmacol., 129, 871–876 (2000)). Heretofore, antagonists for adenosine receptors, particularly for adenosine $A_2$ receptor, have been noted to be useful as an agent for treating or preventing diabetes, diabetic complications, diabetic retinopathy, obesity or asthma, and expected to be useful as a hypoglycemic agent, an improving agent for impaired glucose tolerance, a potentiating agent for insulin sensitivity, a hypotensive agent, a diuretic, a therapeutic agent for osteoporosis, an anti-Parkinson's disease agent, an anti-Alzheimer's disease agent, a therapeutic agent for inflammatory intestinal diseases or a therapeutic agent for Crohn's disease, etc.

For example, there are following reports on compounds having an antagonistic action particularly on $A_{2B}$ receptor.

(1) Compounds represented by the formulae:

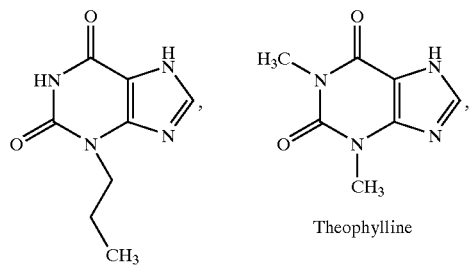

3-n-Propylxanthine

Theophylline

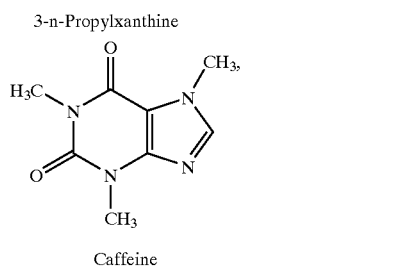

Caffeine

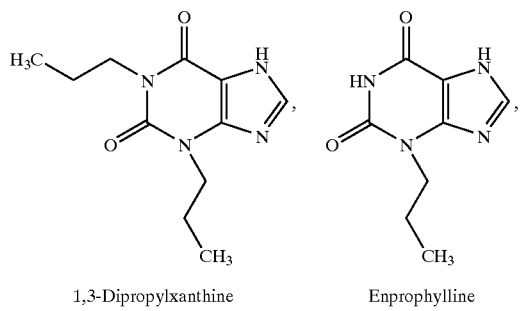

1,3-Dipropylxanthine

Enprophylline

-continued

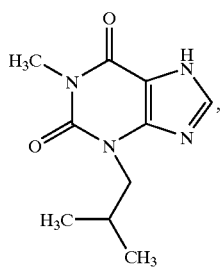

1-Methyl-3-isobutylxanthine

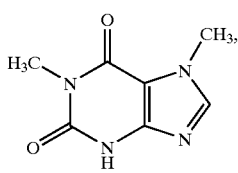

Paraxanthine

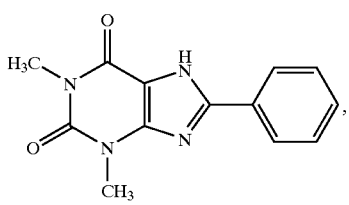

8-Phenyltheophylline

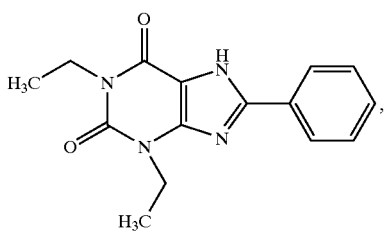

1,3-Diethyl-8-phenylxanthine

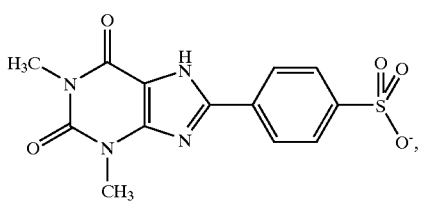

1,3-Dimethyl-8-(p-sulfophenyl)xanthine

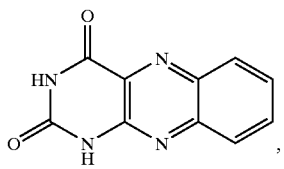

Alloxazine

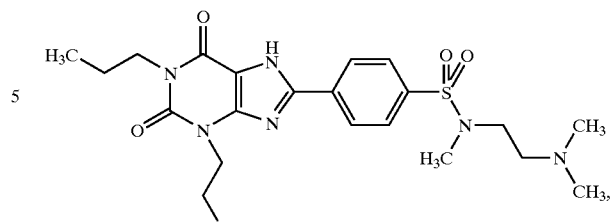

8-[4-[[[Methyl-(2-dimethylaminoethyl)-amino]sulfonyl]phenyl]-1,3-dipropylxanthine

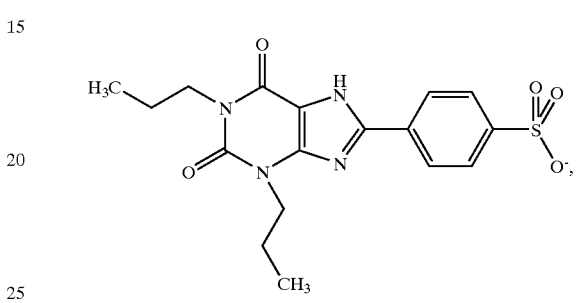

1,3-Dipropyl-8-(p-sulfophenyl)xanthine

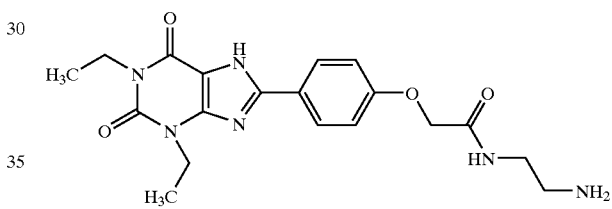

8-[4-[[[[(2-Aminoethyl)amino]carbonyl]methyl]oxy]phenyl]-1,3-dipropylxanthine, 2,4-Dioxobenzo[g]pteridine 2,4-Dioxobenzo[g]pteridine (2) Purine derivatives represented by the formula:

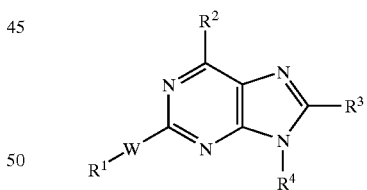

(wherein $R^1$ means (1) the formula

(wherein X means hydrogen atom, hydroxyl group, an optionally substituted lower alkyl group, an optionally substituted lower alkoxy group etc.; and $R^5$ and $R^6$ are the same as or different from each other and each means hydrogen atom, an optionally substituted lower alkyl group, an optionally substituted saturated or unsaturated $C_{3-8}$ cycloalkyl group etc.) or (2) a 5- to 6-membered aromatic ring which may have a substituent group and a hetero atom; W means the formula —CH$_2$CH$_2$—, —CH=CH— or —C≡C—; R$^2$ means an amino group which may be substituted with an optionally substituted lower alkyl group etc., etc.; R$^3$ means an optionally substituted C$_{3-8}$ cycloalkyl group, an optionally substituted aryl group, etc.; and R$^4$ means an optionally substituted lower alkyl group etc.), or a pharmacologically acceptable salt thereof or a hydrate of them (JP-A 11-263789).

(3) Purine derivatives represented by the formula:

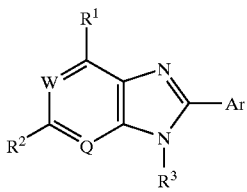

(wherein R$^1$ represents hydrogen atom, hydroxyl group, a halogen atom, an optionally substituted C$_{1-8}$ alkyl group, etc.; R$^2$ represents an amino group which may be substituted with a C$_{1-8}$ alkyl group, etc.; R$^3$ represents a C$_{3-8}$ alkynyl group which may be substituted with a halogen atom, hydroxyl group or a C$_{1-4}$ alkyl group, etc.; Ar represents an optionally substituted aryl group, an optionally substituted heteroaryl group, etc.; and Q and W are the same as or different from each other and each represents N or CH), a pharmacologically acceptable salt thereof or a hydrate of them.

(4) A$_{2B}$ receptor antagonists described in Drug Development Research, 48: 95–103 (1999) and J. Med. Chem., 43: 1165–1172 (2000).

On one hand, as pyridine compounds, for example, there are reports relating to 5,6-aromatic substituted pyridine compound in WO 96/24584, U.S. Pat. No. 5,686,470 and U.S. Pat. No. 5,916,905. Further, in DE-A1 4117802, there are reports relating to 2-amino-3-pyridinecarbonitrile, and relating to the compound in which the 4-, 5- and 6-positions of the pyridine ring are substituted with phenyl groups. However, the relationship of these compounds with an adenosine receptor is not described or suggested, and is not known at all.

As described above, those compounds having an antagonism to an adenosine receptor, particularly an antagonism to an adenosine A$_2$ receptor (especially A$_{2b}$ receptor), are expected to exhibit an excellent action as pharmaceutical preparations and desired to be provided. However, those compounds having an excellent antagonism to an adenosine receptor and also acting effectively as a medicament have never been found. Accordingly, the object of the present invention is to search for, and find, the receptor inhibiting compound which is useful as an agent for treating or preventing a disease to which an adenosine receptor (particularly A$_2$ receptor, A$_{2b}$ receptor) relates.

DISCLOSURE OF THE INVENTION

Considering the above-described circumstances, the present inventors made intensive study. As a result, they have succeeded for the first time in synthesizing a compound represented by the formula:

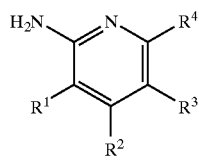

(wherein R$^1$ represents cyano group, carboxyl group or an optionally substituted carbamoyl group; R$^2$ represents hydrogen atom, hydroxyl group, an optionally substituted C$_{1-6}$ alkoxy group, an optionally substituted C$_{6-14}$ aromatic hydrocarbon cyclic group or an optionally substituted 5- to 14-membered aromatic heterocyclic group; and R$^3$ and R$^4$ are the same as or different from each other and each represents a C$_{3-8}$ cycloalkyl group, a C$_{3-8}$ cycloalkenyl group, a C$_{6-14}$ aromatic hydrocarbon cyclic group, a 5- to 14-membered non-aromatic heterocyclic group or a 5- to 14-membered aromatic heterocyclic group which may have a substituent group, respectively, provided that the cases where (1) R$^1$ is cyano group, R$^2$ is 4-bromo-2-thienyl group, R$^3$ is 3,4-dimethoxyphenyl group and R$^4$ is 2-thienyl group, (2) R$^1$ is cyano group, R$^2$ is hydrogen atom, and each of R$^3$ and R$^4$ is phenyl group, (3) R$^1$ is cyano group, R$^2$ is 4-chlorophenyl group, R$^3$ is phenyl group and R$^4$ is 4-(3,4-dichlorophenyl)-1-oxo-2(1H)-phthalazinyl group, (4) R$^1$ is cyano group, R$^2$ is hydrogen atom, R$^3$ is 4-pyridyl group and R$^4$ is 1-piperazinyl group, (5) R$^1$ is cyano group, R$^2$ is hydrogen atom, R$^3$ is 4-pyridyl group and R$^4$ is a 1-pyridyl group, (6) R$^1$ is cyano group, R$^2$ is hydrogen atom, R$^3$ is 4-pyridyl group and R$^4$ is 4-diphenylmethyl-1-piperazinyl group, (7) R$^1$ is cyano group, R$^2$ is hydrogen atom, R$^3$ is 4-pyridyl group and R$^4$ is 4-morpholinyl group, (8) R$^1$ is cyano group, R$^2$ is 4-methylphenyl group, and each of R$^3$ and R$^4$ is phenyl group and (9) R$^1$ is cyano group, and each of R$^2$, R$^3$ and R$^4$ is phenyl group are excluded) or a salt thereof, and they unexpectedly found that the compound and a salt thereof have an excellent antagonistic action on adenosine A$_2$ receptor, particularly A$_{2B}$ receptor. As a result of further intensive study, they found that the compound or a salt thereof is useful not only as an agent for treating, preventing or improving a disease to which an adenosine receptor, particularly A$_2$ receptor, especially A$_{2B}$ receptor, relates, for example, constipation, irritable bowel syndrome, constipation accompanying irritable bowel syndrome, organic constipation, constipation accompanying enteroparalytic ileus, constipation accompanying congenital digestive tract dysfunction, constipation accompanying ileus, diabetes, diabetic complications, diabetic retinopathy, obesity, asthma etc., but also useful as a hypoglycemic agent, an improving agent for impaired glucose tolerance, a potentiating agent for insulin sensitivity, hypotensive agent, a diuretic, a therapeutic agent for osteoporosis, an anti-Parkinson's disease agent, an anti-Alzheimer's disease agent, a therapeutic agent for inflammatory intestinal diseases, a therapeutic agent for Crohn's disease etc., and thus completed the present invention.

That is, the present invention relates to (1) a compound represented by the above formula (I) or a salt thereof; (2) the compound according to the above-mentioned (1) or a salt thereof, in which R$^1$ is cyano group; (3) the compound according to the above-mentioned (1) or a salt thereof, in which R$^1$ is a carbamoyl group represented by the formula:

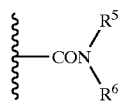

(wherein $R^5$ and $R^6$ are the same as or different from each other and each represents hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group or an optionally substituted 5- to 14-membered aromatic heterocyclic group); (4) the compound according to the above-mentioned (1) or a salt thereof, in which $R^2$ is a $C_{6-14}$ aromatic hydrocarbon cyclic group or 5- to 14-membered aromatic heterocyclic group, each of which may have a substituent group; (5) the compound according to the above-mentioned (1) or a salt thereof, in which $R^2$ is a phenyl group, naphthyl group, pyridyl group, thienyl group or furyl group, each of which may have a substituent group; (6) the compound according to the above-mentioned (1) or a salt thereof, in which $R^2$ is a phenyl group which may be substituted with a halogen atom; (7) the compound according to the above-mentioned (1) or a salt thereof, in which $R^2$ is hydrogen atom; (8) the compound according to the above-mentioned (1) or a salt thereof, in which $R^3$ and $R^4$ are the same as or different from each other and each represents a $C_{6-14}$ aromatic hydrocarbon cyclic group or a 5- to 14-membered aromatic heterocyclic group, each of which may have a substituent group; (9) the compound according to the above-mentioned (1) or a salt thereof, in which $R^3$ and $R^4$ are the same as or different from each other and each represents a phenyl group, pyrrolyl group, pyridinyl group, pyridazinyl group, pyrimidinyl group, pyrazinyl group, thienyl group, thiazolyl group, furyl group, naphthyl group, quinolinyl group, isoquinolinyl group, phthalazinyl group, naphthyridinyl group, indolyl group or isoindolyl group, each of which may have a substituent group; (10) the compound according to the above-mentioned (1) or a salt thereof, in which each of $R^3$ and $R^4$ represents a phenyl group, pyridyl group, thienyl group or furyl group which may have a substituent group, respectively; (11) the compound according to the above-mentioned (1) or salts thereof, wherein $R^3$ and/or $R^4$ represent a 5- to 14-membered non-aromatic heterocyclic group, a $C_{6-14}$ aromatic hydrocarbon cyclic group or a 5- to 14-membered aromatic heterocyclic group, each of which may be substituted with at least one group selected from the following substituent group a (the above-mentioned "substituent group a" is a group consisting of (1) a hydroxyl group, (2) a halogen atom, (3) a nitrile group, (4) a nitro group, (5) a $C_{1-6}$ alkyl group, $C_{2-6}$ alkenyl group or $C_{2-6}$ alkynyl group, each of which may be substituted with at least one group selected from (i) hydroxyl group, (ii) nitrile group, (iii) halogen atom, (iv) $C_{1-6}$ alkylamino group, (v) di($C_{1-6}$ alkyl)amino group, (vi) $C_{2-6}$ alkenylamino group, (vii) di($C_{2-6}$ alkenyl)amino group, (viii) $C_{2-6}$ alkynylamino group, (ix) di($C_{2-6}$ alkynyl)amino group, (x) N—$C_{1-6}$ alkyl-N—$C_{2-6}$ alkenylamino group, (xi) N—$C_{1-6}$ alkyl-N—$C_{2-6}$ alkynylamino group, (xii) N—$C_{2-6}$ alkenyl-N—$C_{2-6}$ alkynylamino group, (xiii) aralkyloxy group, (xiv) TBDMS oxy group, (xv) $C_{1-6}$ alkylsulfonylamino group, (xvi) $C_{1-6}$ alkylcarbonyloxy group, (xvii) $C_{2-6}$ alkenylcarbonyloxy group, (xviii) $C_{2-6}$ alkynylcarbonyloxy group, (xix) N—$C_{1-6}$ alkylcarbamoyl group, (xx) N—$C_{2-6}$ alkenylcarbamoyl group and (xxi) N—$C_{1-6}$ alkynylcarbamoyl group, (6) a $C_{1-6}$ alkoxy group, $C_{2-6}$ alkenyloxy group or $C_{2-6}$ alkynyloxy group, each of which may be substituted with at least one group selected from (i) $C_{1-6}$ alkylamino group, (ii) aralkyloxy group and (iii) hydroxyl group, (7) a $C_{1-6}$ alkylthio group, $C_{2-6}$ alkenylthio group or $C_{2-6}$ alkynylthio group, each of which may be substituted with at least one group selected from (i) hydroxyl group, (ii) nitrile group, (iii) halogen atom, (iv) $C_{1-6}$ alkylamino group, (v) aralkyloxy group, (vi) TBDMS oxy group, (vii) $C_{1-6}$ alkylsulfonylamino group, (viii) $C_{1-6}$ alkylcarbonyloxy group and (ix) $C_{1-6}$ alkylcarbamoyl group, (8) a carbonyl group substituted with a group selected from (i) $C_{1-6}$ alkoxy group, (ii) amino group, (iii) $C_{1-6}$ alkylamino group, (iv) di($C_{1-6}$ alkyl)amino group, (v) $C_{2-6}$ alkenylamino group, (vi) di($C_{2-6}$ alkenyl)amino group, (vii) $C_{2-6}$ alkynylamino group, (vii) di($C_{2-6}$ alkynyl)amino group, (viii) N—$C_{1-6}$ alkyl-N—$C_{2-6}$ alkenylamino group, (ix) N—$C_{1-6}$ alkyl-N—$C_{2-6}$ alkynylamino group and (x) N—$C_{2-6}$ alkenyl-N—$C_{2-6}$ alkynylamino group, (9) an amino group which may be substituted with one or two groups selected from (i) $C_{1-6}$ alkyl group, (ii) $C_{2-6}$ alkenyl group, (iii) $C_{2-6}$ alkynyl group, (iv) $C_{1-6}$ alkylsulfonyl group, (v) $C_{2-6}$ alkenylsulfonyl group, (vi) $C_{2-6}$ alkynylsulfonyl group, (vii) $C_{1-6}$ alkylcarbonyl group, (viii) $C_{2-6}$ alkenylcarbonyl group and (ix) $C_{2-6}$ alkynylcarbonyl group, (10) a $C_{1-6}$ alkylsulfonyl group, (11) a $C_{2-6}$ alkenylsulfonyl group, (12) a $C_{2-6}$ alkynylsulfonyl group, (13) a $C_{1-6}$ alkylsulfinyl group, (14) a $C_{2-6}$ alkenylsulfinyl group, (15) a $C_{2-6}$ alkynylsulfinyl group, (16) a formyl group, (17) a $C_{3-8}$ cycloalkyl group or $C_{3-8}$ cycloalkenyl group, each of which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, (18) a 5- to 14-membered non-aromatic heterocyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, (19) a $C_{6-14}$ aromatic hydrocarbon cyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, and (20) a 5- to 14-membered aromatic heterocyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group); (12) the compound according to the above-mentioned (1) or a salt thereof, in which $R^3$ and/or $R^4$ represent a phenyl group, pyridyl group, thienyl group or furyl group, each of which may be substituted with at least one group selected from hydroxyl group, a halogen atom, a $C_{1-6}$ alkyl group and a $C_{1-6}$ alkoxy group; (13) the compound according to the above-mentioned (1) or a salt thereof, in which $R^3$ or $R^4$ is a 6-oxo-1,6-dihydropyridyl group which may have a substituent group; (14) the compound according to the above-mentioned (1) represented by the formula:

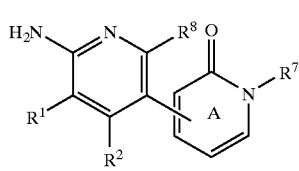

(II)

(wherein $R^1$ represents cyano group, carboxyl group or an optionally substituted carbamoyl group; $R^2$ represents hydrogen atom, hydroxyl group, an optionally substituted $C_{1-6}$ alkoxy group, an optionally substituted $C_{1-6}$ alkylthio group, an optionally substituted $C_{6-14}$ aromatic hydrocarbon cyclic group or an optionally substituted 5- to 14-membered aromatic heterocyclic group; $R^7$ represents a group selected from the following substituent group b; $R^8$ represents a $C_{6-14}$ aromatic hydrocarbon cyclic group or a 5- to 14-membered aromatic heterocyclic group which may have a substituent group, respectively; and ring A represents a nitrogen-containing 6-membered ring which may be substituted with 1 to 4 groups selected from the following substituent group b.

<substituent group b> a group consisting of hydrogen atom, a halogen atom, hydroxyl group, nitro group, cyano group, an optionally substituted $C_{1-6}$ alkyl group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{2-6}$ alkenyloxy group, an optionally substituted $C_{2-6}$ alkynyloxy group, an optionally substituted $C_{1-6}$ alkylthio group, an optionally substituted $C_{2-6}$ alkenylthio group, an optionally substituted $C_{2-6}$ alkynylthio group, a $C_{2-7}$ fatty acyl group, an optionally substituted carbamoyl group, an arylacyl group, a heteroaryl acyl group, an optionally substituted amino group, an optionally substituted $C_{1-6}$ alkylsulfonyl group, an optionally substituted $C_{2-6}$ alkenylsulfonyl group, an optionally substituted $C_{2-6}$ alkynylsulfonyl group, an optionally substituted $C_{1-6}$ alkylsulfinyl group, an optionally substituted $C_{2-6}$ alkenylsulfinyl group, an optionally substituted $C_{2-6}$ alkynylsulfinyl group, formyl group, an optionally substituted $C_{3-8}$ cycloalkyl group, an optionally substituted $C_{3-8}$ cycloalkenyl group, an optionally substituted 5- to 14-membered non-aromatic heterocyclic group, an optionally substituted $C_{6-14}$ aromatic hydrocarbon cyclic group and an optionally substituted 5- to 14-membered aromatic heterocyclic group) or a salt thereof; (15) the compound according to the above-mentioned (14) or a salt thereof, in which $R^1$ is cyano group; (16) the compound according to the above-mentioned (14) or a salt thereof, in which $R^1$ is carboxyl group; (17) the compound according to the above-mentioned (14) or a salt thereof, in which $R^1$ is a carbamoyl group represented by the formula:

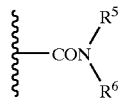

in which $R^5$ and $R^6$ have the same meanings as defined above; (18) the compound according to the above-mentioned (14) or a salt thereof, in which $R^2$ is a hydrogen atom; (19) the compound according to the above-mentioned (14) or a salt thereof, in which $R^7$ and the substituent groups other than $R^7$ in the ring A are selected from the above-mentioned substituent group a; (20) the compound according to the above-mentioned (14) or a salt thereof, in which $R^7$ is hydrogen atom, an optionally substituted $C_{1-6}$ alkyl group, an optionally substituted $C_{2-6}$ alkenyl group or an optionally substituted $C_{1-6}$ alkoxy group; (21) the compound according to the above-mentioned (14) or a salt thereof, in which $R^8$ is a phenyl group, pyridyl group, furyl group or a thienyl group, each of which may have a substituent group; (22) the compound according to the above-mentioned (14) or a salt thereof, in which $R^8$ is a phenyl group, pyridyl group, furyl group or a thienyl group, each of which may be substituted with a halogen atom; (23) the compound according to the above-mentioned (1), in which the compound is any one selected from 2-amino-6-(2-furyl)-5-(4-pyridyl)-3-pyridinecarbonitrile, 2-amino-6-(3-fluorophenyl)-5-(4-pyridyl)-3-pyridinecarbonitrile, 2-amino-6-(2-furyl)-5-(4-methoxy-3-pyridyl)-3-pyridinecarbonitrile, 2-amino-6-(2-furyl)-5-(6-oxo-1,6-dihydro-3-pyridinyl)nicotinonitrile, 2-amino-5-(1-ethyl-6-oxo-1,6-dihydro-3-pyridinyl)-6-(2-furyl)nicotinonitrile, 2-amino-6-(2-furyl)-5-(1-methyl-6-oxo-1,6-dihydro-3-pyridinyl)nicotinonitrile, 2-amino-6-(3-fluorophenyl)-5-(6-oxo-1,6-dihydro-3-pyridinyl)nicotinonitrile and 2-amino-6-(3-fluorophenyl)-5-(1-methyl-6-oxo-1,6-dihydro-3-pyridinyl)nicotinonitrile, or a salt thereof; (24) a pharmaceutical composition comprising a compound represented by the formula:

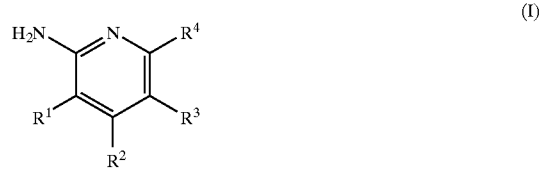

(wherein $R^1$ represents cyano group, carboxyl group or an optionally substituted carbamoyl group; $R^2$ represents hydrogen atom, hydroxyl group, an optionally substituted $C_{1-6}$ alkoxy group, an optionally substituted $C_{6-14}$ aromatic hydrocarbon cyclic group or an optionally substituted 5- to 14-membered aromatic heterocyclic group; and $R^3$ and $R^4$ are the same as or different from each other and each represents a $C_{3-8}$ cycloalkyl group, a $C_{3-8}$ cycloalkenyl group, a $C_{6-14}$ aromatic hydrocarbon cyclic group, a 5- to 14-membered non-aromatic heterocyclic group or a 5- to 14-membered aromatic heterocyclic group which may have a substituent group, respectively, provided that the cases where (1) $R^1$ is cyano group, $R^2$ is 4-bromo-2-thienyl group, $R^3$ is 3,4-dimethoxyphenyl group and $R^4$ is 2-thienyl group, (2) $R^1$ is cyano group, $R^2$ is hydrogen atom and each of $R^3$ and $R^4$ is phenyl group, (3) $R^1$ is cyano group, $R^2$ is 4-chloro-phenyl group, $R^3$ is phenyl group and $R^4$ is 4-(3,4-dichlorophenyl)-1-oxo-2(1H)-phthalazinyl group, (4) $R^1$ is cyano group, $R^2$ is hydrogen atom, $R^3$ is 4-pyridyl group and $R^4$ is 1-piperazinyl group, (5) $R^1$ is cyano group, $R^2$ is hydrogen atom, $R^3$ is 4-pyridyl group and $R^4$ is 1-pyridyl group, (6) $R^1$ is cyano group, $R^2$ is hydrogen atom, $R^3$ is 4-pyridyl group and $R^4$ is 4-diphenylmethyl-1-piperazinyl group, (7) $R^1$ is cyano group, $R^2$ is hydrogen atom, $R^3$ is 4-pyridyl group and $R^4$ is 4-morpholinyl group, (8) $R^1$ is cyano group, $R^2$ is 4-methylphenyl group and each of $R^3$ and $R^4$ is phenyl group, and (9) $R^1$ is cyano group and each of $R^2$, $R^3$ and $R^4$ is phenyl group are excluded) or a salt thereof; (25) the composition according to the above-mentioned (24), which is an agent for treating or preventing a disease to which an adenosine receptor relates; (26) the composition according to the above-mentioned (24), which is an agent for treating or preventing a disease to which an adenosine $A_2$ receptor relates; (27) the composition according to the above-mentioned (24), which is an agent for treating or preventing a disease to which an adenosine $A_{2B}$ receptor relates; (28) the composition according to the above-mentioned (24), which is an adenosine receptor antagonist; (29) the composition according to claim 24, which is an adenosine $A_2$ receptor antagonist; (30) the composition according to the above-mentioned (24), which is an adenosine $A_{2B}$ receptor antagonist; (31) the composition according to the above-mentioned (24), which is used for promoting defecation; (32) the composition according to the above-mentioned (24), which is an agent for treating, preventing or improving constipation; (33) the composition according to the above-mentioned (24), in which the constipation is functional constipation; (34) the composition according to the above-mentioned (24), which is an agent for treating irritable bowel syndrome, constipation accompanying irritable bowel syndrome, organic constipation, constipation accompanying enteroparalytic ileus, constipation accompanying congenital digestive tract dysfunction or constipation accompanying ileus; (35) the composition according to the above-mentioned (24), which is used for evacuating intestinal tracts at the time of examination of digestive tracts or before and after an operation; (36) the composition according to the above-mentioned (24), which is an agent for treating or preventing diabetes, diabetic complications, diabetic retinopathy, obesity or asthma; (37) the composition according to the above-mentioned (24), which is a hypoglycemic agent, an improving agent for impaired glucose tolerance and a potentiating agent for insulin sensitivity; (38) the composition according to the above-mentioned (24), which is a hypotensive agent, a diuretic, a therapeutic agent for osteoporosis, an anti-Parkinson's disease agent, an anti-Alzheimer's disease agent, a therapeutic agent for inflammatory intestinal diseases or a therapeutic agent for Crohn's disease, etc.

That is, the present invention is a pharmaceutical composition comprising the above-mentioned 2-aminopyridine compound or a pharmacologically acceptable salt thereof and a pharmaceutically acceptable carrier, use of the above-mentioned compound or a pharmacologically acceptable salt thereof for producing an agent for treating or preventing a disease to which an adenosine receptor relates, and a method of treating or preventing a disease to which an adenosine receptor relates, by administering a pharmacologically effective dose of the above-mentioned compound or a pharmacologically acceptable salt thereof to a patient.

Hereinafter, the meanings of symbols, terms etc. used in the present specification are described, and the present invention is described in detail.

The "antagonist" in this specification refers to an agent having affinity for adenosine receptors, particularly adenosine $A_2$ receptor (most preferably $A_{2B}$ receptor) and inactivating the receptor.

In this specification, the "disease to which an adenosine receptor relates" means a disease to which an adenosine $A_1$ receptor, $A_{2a}$ receptor, $A_{2b}$ receptor or $A_3$ receptor relates. For example, various kinds of constipation, irritable bowel syndrome, constipation accompanying irritable bowel syndrome, organic constipation, constipation accompanying intestinal paralytic ileus, constipation accompanying congenital digestive tract dysfunction, constipation accompanying ileus, diabetes, diabetic complications, diabetic retinopathy, obesity or asthma, or a disease against which a hypoglycemic agent, an improving agent for impaired glucose tolerance, a potentiating agent for insulin sensitivity, a hypotensive agent, a diuretic, a therapeutic agent for osteoporosis, an anti-Parkinson's disease agent, an anti-Alzheimer's disease agent, a therapeutic agent for inflammatory intestinal diseases or a therapeutic agent for Crohn's disease is efficacious.

The term "and/or" used in this specification refers to both of "and" and "or".

The structural formulae of the compound in this specification may, for convenience' sake, indicate a certain isomer, but the present invention encompasses all possible isomers which can occur in the structures of the compound, for example, geometric isomer, optical isomer based on asymmetrical carbon, rotational isomer, stereoisomer and tautomer, as well as a mixture of such isomers, so the compound of the invention may be any isomers or a mixture thereof without limitation to the formulae shown for convenience' sake. Accordingly, the compound of the present invention can have an intramolecular asymmetrical carbon to occur as optically active isomers or racemic modifications, and any of such compounds are included in the present invention without limitation. Further, crystal polymorphism may present also without limitation, and it may be in a single crystal form or a mixed crystal form. The compound (I) according to the present invention or a salt thereof may be anhydrides or hydrates, any of which fall under the claims in the present specification. Metabolites formed by decomposition of the Compound (I) according to the present invention in vivo, as well as prodrugs of the compound (I) according to the present invention or a salt thereof also fall under the claims in the present specification.

As the "halogen atom" used in the present specification, for example, atoms such as fluorine atom, chlorine atom, bromine atom, iodine atom etc. may be proposed, and fluorine atom, chlorine atom and bromine atom are preferred.

The "$C_{1-6}$ alkyl group" used in this specification refers to an alkyl group containing 1 to 6 carbon groups, and examples thereof include linear or branched alkyl groups such as methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1,-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group or 3-methylpentyl group may be proposed.

The "$C_{2-6}$ alkenyl group" used in this specification refers to an alkenyl group containing 2 to 6 carbon atoms. As the preferable examples thereof, for example, vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group, 1,6-hexanedienyl group etc. may be proposed.

The "$C_{2-6}$ alkynyl group" used in this specification refers to an alkynyl group containing 2 to 6 carbon atoms. As the preferable examples thereof, for example, ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexanediynyl group, 1,6-hexanediynyl group etc. may be proposed.

The "$C_{1-6}$ alkoxy group" used in this specification refers to an alkoxy group containing 1 to 6 carbon groups, for example, methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2- dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group, hexyloxy group etc.

The "$C_{2-6}$ alkenyloxy group" used in this specification refers to an alkenyloxy group containing 2 to 6 carbon atoms. As the preferable group, for example, vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexanedienyloxy group, 1,6-hexanedienyloxy group etc. may be proposed.

The "$C_{2-6}$ alkynyloxy group" used in this specification refers to an alkynyloxy group containing 2 to 6 carbon atoms. Preferably, for example, ethynyloxy group, 1-propynyloxy group, 2-propynyloxy group, 1-butynyloxy group, 2-butynyloxy group, 3-butynyloxy group, 3-methyl-1-propynyloxy group, 1-ethynyl-2-propynyloxy group, 2-methyl-3-propynyloxy group, 1-pentynyloxy group, 1-hexynyloxy group, 1,3-hexanediynyloxy group, 1,6-hexanediynyloxy group etc. may be proposed.

The "$C_{1-6}$ alkylthio group" used in this specification refers to an alkoxy group containing 1 to 6 carbon groups. For example, methylthio group, ethylthio group, n-propylthio group, iso-propylthio group, sec-propylthio group, n-butylthio group, iso-butylthio group, sec-butylthio group, tert-butylthio group, n-pentylthio group, iso-pentylthio group, sec-pentylthio group, n-hexylthio group, iso-hexylthio group, 1,1-dimethylpropylthio group, 1,2-dimethylpropylthio group, 2,2-dimethylpropylthio group, 2-ethylpropylthio group, 1-methyl-2-ethylpropylthio group, 1-ethyl-2-methylpropylthio group, 1,1,2-trimethylpropylthio group, 1,1,2-trimethylpropylthio group, 1,1,-dimethylbutylthio group, 1,2-dimethylbutylthio group, 2,2-dimethylbutylthio group, 2,3-dimethylbutylthio group, 1,3-dimethylbutylthio group, 2-ethylbutylthio group, 1,3-dimethylbutylthio group, 2-methylpentylthio group, 3-methylpentylthio group etc. may be proposed. The "$C_{2-6}$ alkenylthio group" used in this specification refers to an alkenylthio group containing 2 to 6 carbon atoms. The preferable examples thereof include vinylthio group, allylthio group, 1-propenylthio group, 2-propenylthio group, isopropenylthio group, 2-methyl-1-propenylthio group, 3-methyl-1-propenylthio group, 2-methyl-2-propenylthio group, 3-methyl-2-propenylthio group, 1-butenylthio group, 2-butenylthio group, 3-butenylthio group, 1-pentenylthio group, 1-hexenylthio group, 1,3-hexanedienylthio group, 1,6-hexanedienylthio group, etc. The "$C_{2-6}$ alkynylthio group" used in this specification refers to an alkynylthio group containing 2 to 6 carbon atoms. The preferable examples thereof include ethynylthio group, 1-propynylthio group, 2-propynylthio group, 1-butynylthio group, 2-butynylthio group, 3-butynylthio group, 3-methyl-1-propynylthio group, 1-ethynyl-2-propynylthio group, 2-methyl-3-propynylthio group, 1-pentynylthio group, 1-hexynylthio group, 1,3-hexanediynylthio group, 1,6-hexanediynylthio group, etc.

The "$C_{3-8}$ cycloalkyl group" used in this specification refers to a cycloalkyl group containing 3 to 8 carbon atoms, and examples thereof include cyclopropyl group, cyclobutyl group, cyclopentyl group, cyclohexyl group, cycloheptyl group, cyclooctyl group etc.

The "$C_{3-8}$ cycloalkenyl group" used in this specification refers to a $C_{3-8}$ cycloalkenyl group containing 3 to 8 carbon atoms. For example, cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl, cyclohepten-1-yl, cyclohepten-3-yl, cyclohepten-4-yl, cyclohepten-5-yl, 1,3-cyclohepten-2-yl, 1,3-cyclohepten-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-7-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl, 1,3,6-cyclooctatrien-6-yl group, etc. may be proposed.

The "5- to 14-membered non-aromatic heterocyclic group" used in this specification refers to a monocyclic, bicyclic or tricyclic, 5- to 14-membered non-aromatic heterocyclic group containing at least one heteroatom selected from nitrogen atom, sulfur atom and oxygen atom. Specific examples of the group include pyrrolidinyl group, pyrrolyl group, piperidinyl group, piperazinyl group, imidazolyl group, pyrazolidyl group, imidazolidyl group, morpholyl group, tertrahydrofuryl group, tetrahydropyranyl group, pyrrolinyl group, dihydrofuryl group, dihydropyranyl group, imidazolinyl group, oxazolinyl group, etc. Further, the non-aromatic heterocyclic group also includes a group derived from a pyridone ring or a non-aromatic fused ring (for example, a group derived from a phthalimide ring, succinimide ring, etc.).

The "$C_{6-14}$ aromatic hydrocarbon cyclic group" and "aryl" used in this specification refer to an aromatic hydrocarbon cyclic group containing 6 to 14 carbon atoms, and include a monocyclic group and a condensed ring such as bicyclic group, tricyclic group etc. Specific examples of this group include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, benzocyclooctenyl group, etc. may be proposed.

In this specification, the "5- to 14-membered aromatic heterocyclic group" and "heteroaryl" refer to a monocyclic, bicyclic or tricyclic, 5- to 14-membered aromatic heterocyclic group containing at least one heteroatom selected from nitrogen atom, sulfur atom and oxygen atom. Specific examples of the group include, for example, 1) nitrogen-containing aromatic heterocyclic groups such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, pyrimidinyl group, phenanthrolinyl group, phenacynyl group, imidazopyridinyl group, imidazopyrimidinyl group, pyrazolopyridinyl group, pyrazolopyridinyl group, etc.; 2) sulfur-containing aromatic heterocyclic groups such as thienyl group, benzothienyl group, etc.; 3) oxygen-containing aromatic heterocyclic groups such as furyl group, pyranyl group, cyclopentapyranyl group, benzofuryl group, isobenzofuryl group, etc.; and 4) aromatic heterocyclic group containing two or more heteroatoms, such as thiazolyl group, isothiazolyl group, benzothiazolyl group, benzthiadiazolyl group, phenothiazinyl group, isoxazolyl group, furazanyl group, phenoxazinyl group, oxazolyl group, isoxazoyl group, benzoxazolyl group, oxadiazolyl group, pyrazolooxazolyl group, imidazothiazolyl group, thienofuranyl group, furopyrrolyl group, pyridoxazinyl group, etc.

The "$C_{2-7}$ fatty acyl group" used in this specification refers to an atomic group derived by removing an OH group from a carboxyl group of a $C_{2-7}$ fatty carboxylic acid. As the preferable group thereof, for example, acetyl group, propionyl group, butyroyl group, etc. may be proposed.

The "arylacyl group" used in this specification refers to a carbonyl group substituted with a $C_{6-14}$ aromatic hydrocarbon cyclic group, and the "heteroarylacyl group" refers to a carbonyl group substituted with a 5- to 14-membered aromatic heterocyclic group. The "$C_{6-14}$ aromatic hydrocarbon cyclic group" and "5- to 14-membered aromatic heterocyclic group" have the same meaning as defined above.

Preferable examples of the "$C_{1-6}$ alkylsulfonyl group", "$C_{2-6}$ alkenylsulfonyl group" and "$C_{2-6}$ alkynylsulfonyl group" used in this specification include methylsulfonyl group, ethylsulfonyl group, n-propylsulfonyl group, iso-propylsulfonyl group, n-butylsulfonyl group, tert-butylsulfonyl group, vinylsulfonyl group, allylsulfonyl group, iso-propenylsulfonyl group, iso-pentenylsulfonyl group, ethynylsulfonyl group etc. Preferable examples of the "$C_{1-6}$ alkylsulfinyl group", "$C_{2-6}$ alkenylsulfinyl group" and "$C_{2-6}$ alkynylsulfinyl group" used in this specification include methylsulfinyl group, ethylsulfinyl group, n-propylsulfinyl group, iso-propylsulfinyl group, n-butylsulfinyl group, tert-butylsulfinyl group, vinylsulfinyl group, allylsulfinyl group, iso-propenylsulfinyl group, iso-pentenylsulfinyl group, ethynylsulfinyl group, etc.

As the "substituent group" in the "optionally substituted amino group" used in this specification, for example, one or two groups selected from a $C_{1-6}$ alkyl group, $C_{2-6}$ alkenyl group, $C_{2-6}$ alkynyl group, $C_{1-6}$ alkylsulfonyl group, $C_{2-6}$ alkenylsulfonyl group, $C_{2-6}$ alkynylsulfonyl group, $C_{1-6}$ alkylcarbonyl group, $C_{2-6}$ alkenylcarbonyl group and $C_{2-6}$ alkynylcarbonyl group, each of which may have a substituent group may be proposed, and the substituent groups may be bound together to form a 3- to 8-membered nitrogen-containing ring. Preferable examples of the "substituent group" of the above-mentioned $C_{1-6}$ alkyl group, $C_{2-6}$ alkenyl group, $C_{2-6}$ alkynyl group, $C_{1-6}$ alkylsulfonyl group, $C_{2-6}$ alkenylsulfonyl group, $C_{2-6}$ alkynylsulfonyl group, $C_{1-6}$ alkylcarbonyl group, $C_{2-6}$ alkenylcarbonyl group and $C_{2-6}$ alkynylcarbonyl group include hydroxyl group, a halogen atom, nitrile group, a $C_{1-6}$ alkoxy group, a $C_{1-6}$ alkylthio group, etc. Specifically, as the particularly preferable examples of the above-mentioned "amino group which may have a substituent group", methylamino group, ethylamino group, n-propylamino group, iso-propylamino group, n-butylamino group, iso-butylamino group, tert-butylamino group, n-pentylamino group, iso-pentylamino group, neopentylamino group, n-hexylamino group, 1-methylpropylamino group, 1,2-dimethylpropylamino group, 2-ethylpropylamino group, 1-methyl-2-ethylpropylamino group, 1-ethyl-2-methylpropylamino group, 1,1,2-trimethylpropylamino group, 1-methylbutylamino group, 2-methylbutylamino group, 1,1-dimethylbutylamino group, 2,2-dimethylbutylamino group, 2-ethylbutylamino group, 1,3-dimethylbutylamino group, 2-methylpentylamino group, 3-methylpentylamino group, N,N-dimethylamino group, N,N-diethylamino group, N,N-di(n-propyl)amino group, N,N-di(iso-propyl)amino group, N,N-di(n-butyl)amino group, N,N-di(iso-butyl)amino group, N,N-di(tert-butyl)amino group, N,N-di(n-pentyl)amino group, N,N-di(iso-pentyl)amino group, N,N-di(n-pentyl)amino group, N,N-di(n-hexyl)amino group, N,N-di(1-methylpropyl)amino group, N,N-di(1,2-dimethylpropyl)amino group, N-methyl-N-ethylamino group, N-ethyl-N-(n-propyl)amino group, N-methyl-N-(i-propyl)amino group, vinylamino group, allylamino group, (1-propenyl)amino group, isopropenylamino group, (1-buten-1-yl)amino group, (1-buten-2-yl)amino group, (1-buten-3-yl)amino group, (2-buten-1-yl)amino group, (2-buten-2-yl)amino group, N,N-divinylamino group, N,N-diallylamino group, N,N-di(1-propenyl)amino group, N,N-isopropenylamino group, N-vinyl-N-allylamino group, ethynylamino group, 1-propynylamino group, 2-propynylamino group, butynylamino group, pentynylamino group, hexynylamino group, N,N-diethynylamino group, N,N-(1-propynyl)amino group, N,N-(2-propynyl)amino group, N,N-dibutynylamino group, N,N-dipentynylamino group, N,N-dihexynylamino group, hydroxymethylamino group, 1-hydroxyethylamino group, 2-hydroxyethylamino group, 3-hydroxy-n-propyl group, methylsulfonylamino group, ethylsulfonylamino group, n-propylsulfonylamino group, iso-propylsulfonylamino group, n-butylsulfonylamino group, tert-butylsulfonylamino group, vinylsulfonylamino group, allylsulfonylamino group, iso-propenylsulfonylamino group, iso-pentenylsulfonylamino group, ethynylsulfonylamino group, methylcarbonylamino group, ethylcarbonylamino group, n-propylcarbonylamino group, iso-propylcarbonylamino group, n-butylcarbonylamino group, tert-butylcarbonylamino group, vinylcarbonylamino group, allylcarbonylamino group, iso-propenylcarbonylamino group, iso-pentenylcarbonylamino group, ethynylcarbonylamino group, etc.

As the "substituent group" in the "which may have a substituent group" used in this specification, a halogen atom (for example, fluorine atom, chlorine atom, bromine atom, iodine atom etc.), hydroxyl group, nitro group, cyano group, a $C_{1-6}$ alkyl group (for example, methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group etc.), a $C_{2-6}$ alkenyl group (for example, vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexanedienyl group, 1,6-hexanedienyl group, etc.), a $C_{2-6}$ alkynyl group (for example, ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexanediynyl group, 1,6-hexanediynyl group, etc.), a $C_{1-6}$ alkoxy group (for example, methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, etc.), a $C_{2-6}$ alkenyloxy group (for example, vinyloxy group, allyloxy group, 1-propenyloxy group, 2-propenyloxy group, isopropenyloxy group, etc.), a $C_{2-6}$ alkynyloxy group (for example, ethynyloxy group, 1-propynyloxy group, 2-propynyloxy group, etc.), a $C_{1-6}$ alkylthio group (for example, methylthio group, ethylthio group, n-propylthio group, iso-propylthio group, sec-propylthio group, n-butylthio group, iso-butylthio group, sec-butylthio group, tert-butylthio group, etc.), a $C_{2-6}$ alkenylthio group (for example, vinylthio group, allylthio group, 1-propenylthio group, 2-propenylthio group, etc.), a $C_{2-6}$ alkynylthio group (for example, ethynylthio group, 1-propynylthio group, 2-propynylthio group, etc.), a $C_{2-7}$ fatty acyl group (for example, acetyl group, propionyl group, butyroyl group, etc.), carbamoyl group, arylacyl group, heteroarylacyl group, amino group, a $C_{1-6}$ alkylsulfonyl group, a $C_{2-6}$ alkenylsulfonyl group, a $C_{2-6}$ alkynylsulfonyl group, a $C_{1-6}$ alkylsulfinyl group, $C_{2-6}$ alkenylsulfinyl group, a $C_{2-6}$ alkynylsulfinyl group (for example, methylsulfonyl group, ethylsulfonyl group, n-propylsulfonyl group, iso-propylsulfonyl group, n-butylsulfonyl group, tert-butylsulfonyl group, vinylsulfonyl group, allylsulfonyl group, iso-propenylsulfonyl group, iso-pentenylsulfonyl group, ethynylsulfonyl group, methylsulfinyl group, ethylsulfinyl group, n-propylsulfinyl group, iso-propylsulfinyl group, n-butylsulfinyl group, tert-butylsulfinyl group, vinylsulfinyl group, allylsulfinyl group, iso-propenylsulfinyl group, iso-pentenylsulfinyl group, ethynylsulfinyl group, etc.), formyl group, a $C_{3-8}$ cycloalkyl group (for example, cyclopropyl group, cyclobutyl group, cyclopentyl group, cyclohexyl group, cycloheptyl group, cyclooctyl group etc.), a $C_{3-8}$ cycloalkenyl group (for example, cyclopropenyl, cyclobutenyl, cyclopentenyl, cyclohexenyl group, etc.), a 5- to 14-membered non-aromatic heterocyclic group (for example, pyrrolidinyl group, pyrrolyl group, piperidinyl group, piperazinyl group, imidazolyl group, pyrazolidyl group, imidazolidyl group, morpholyl group, tertrahydrofuryl group, tetrahydropyranyl group, pyrrolinyl group, dihydrofuryl group, dihydropyranyl group, imidazolinyl group, oxazolinyl group, a group derived from a pyridone ring, a group derived from a phthalimide ring or succinimide ring, etc.), a $C_{6-14}$ aromatic hydrocarbon cyclic group (for example, phenyl group, indenyl group, 1-naphthyl group, 2-naphthyl group, biphenyl group, indacenyl group etc.), a 5- to 14-membered aromatic heterocyclic ring (for example, pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, iso-indolyl group, indolizinyl group, purinyl group, indazolyl group, quinolyl group, iso-quinolyl group, quinolizyl group, phthalazyl group, naphthylidinyl group, quinoxalyl group, quinazolinyl group, cynnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenacinyl group, imidazopyridinyl group, imidazopyrimidinyl group, pyrazolopyridinyl group, pyrazolopyridinyl group, thienyl group, benzothienyl group, furyl group, pyranyl group, cyclopentapyranyl group, benzofuryl group, iso-benzofuryl group, thiazolyl group, iso-thiazolyl group, benzothiazolyl group, benzthiadiazolyl group, phenothiazinyl group, isoxazolyl group, furazanyl group, phenoxazinyl group, oxazolyl group, isoxazoyl group, benzoxazolyl group, oxadiazolyl group, pyrazoloxazolyl group, imidazothiazolyl group, thienofuranyl group, furopyrrolyl group, pyridoxadinyl group etc.), and these substituent groups may further have substituent groups.

In the formula (I) above, $R^1$ represents cyano group, carboxyl group or a carbamoyl group which may have a substituent group, and the most preferable group is not particularly limited. As the preferable example of the "substituent group" in the "carbamoyl group which may have a substituent group", a group selected from a $C_{1-6}$ alkyl group which may have a substituent group, a $C_{2-6}$ alkenyl group which may have a substituent group, a $C_{2-6}$ alkynyl group which may have a substituent group, a $C_{3-8}$ cycloalkyl group which may have a substituent group, a $C_{3-8}$ cycloalkenyl group which may have a substituent group, a $C_{6-14}$ aromatic hydrocarbon cyclic group which may have a substituent group, a 5- to 14-membered aromatic heterocyclic group which may have a substituent group etc. may be proposed. The nitrogen atom in the carbamoyl group may be substituted with one or two groups selected from the substituent groups described above. Further, the above-mentioned substituent groups may be bound together to form a 3- to 14-membered nitrogen-containing ring (for example, pyrrolidyl group, pyrrolinyl group, piperidyl group, piperazinyl group, imidazolyl group, pyrazolidyl group, imidazolidyl group, morpholinyl group, tetrahydropyranyl group, aziridinyl group, oxiranyl group, oxathiolanyl group, phthalimidoyl group, succinimidyl group, pyrrolyl group, pyridyl group, pyridazinyl group, pyrimidinyl group, pyrazinyl group, pyrazolyl group, etc.), and the nitrogen-containing rings may further have substituent groups.

Preferable groups of $R^2$ in the formula (I) above are not particularly limited, but more preferable groups include hydrogen atom, a $C_{1-6}$ alkoxy group, phenyl, naphthyl, pyridyl, pyridazyl, pyrimidyl, pyrazyl, thienyl, furyl and imidazolyl groups, each of which may have a substituent group, and further preferably hydrogen atom.

In the formula (I) above, $R^3$ and $R^4$ are independent of each other and each represents a $C_{3-8}$ cycloalkyl group, a $C_{3-8}$ cycloalkenyl group, a $C_{6-14}$ aromatic hydrocarbon cyclic group, a 5- to 14-membered non-aromatic heterocyclic group or a 5- to 14-membered aromatic heterocyclic group, each of which may have a substituent group, and preferable groups include a $C_{6-14}$ aromatic hydrocarbon cyclic group (for example, phenyl group, naphthyl group etc.), a 5- to 14-membered non-aromatic heterocyclic group (for example, pyrrolidinyl group, pyrrolinyl group, piperidinyl group, piperazinyl group, imidazolinyl group, pyrazolidinyl group, imidazolidinyl, morpholinyl group, tetrahydropyranyl group, aziridinyl group, oxiranyl group, oxathiolanyl group, a 6-oxo-1,6-dihydropyridyl group whose nitrogen atom may be substituted etc.) or a 5- to 14-membered aromatic heterocyclic group (for example, pyrrolyl group, pyridyl group, pyridazinyl group, pyrimidinyl group, pyrazinyl group, pyrazolyl group, imidazolyl group, indolyl group, isoindolyl group, indolizinyl group, quinolinyl group, isoquinolinyl group, quinolizinyl group, phthalazinyl group, naphthyridyl group, quinoxalyl group, quinazolyl group, imidazotriazinyl group, pyrazinopyridazinyl group, thienyl group, benzothienyl group, furyl group, pyranyl group, cyclopentapyranyl group, benzofuryl group, isobenzofuryl group, thiazolyl group, isothiazolyl group, benzthiazolyl group, benzthiadiazolyl group, phenothiazyl group, isoxazolyl group, pyrazoloxazolyl group, imidazothiazolyl group, thienofuryl group, furopyrrolyl group, pyridoxazinyl group etc.), and these substituent groups may have substituent groups. As the more preferable examples of $R^3$ and $R^4$, for example, groups represented by the formulae:

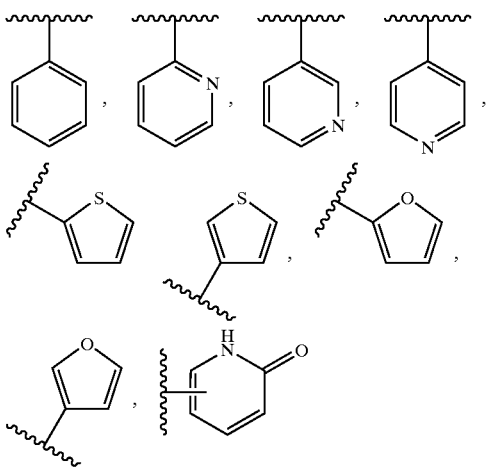

which may be substituted, respectively. When the above-mentioned 6-oxo-1,6-dihydropyridyl group has a substituent group, the case where the substituent group is bound to the nitrogen atom is also included.

As the "substituent" in the "$C_{3-8}$ cycloalkyl group which may have a substituent group", "$C_{3-8}$ cycloalkenyl group which may have a substituent group", "$C_{6-14}$ aromatic hydrocarbon cyclic group which may have a substituent group", "5- to 14-membered non-aromatic heterocyclic group which may have a substituent group" and "5- to 14-membered aromatic heterocyclic group which may have a substituent group" represented by $R^3$ and $R^4$, (1) one or more groups selected from hydroxyl group, a halogen atom, cyano group, nitro group, a $C_{1-6}$ alkyl group which may have a substituent group, a $C_{2-6}$ alkenyl group which may have a substituent group, a $C_{2-6}$ alkynyl group which may have a substituent group, a $C_{1-6}$ alkoxy group which may have a substituent group, a $C_{2-6}$ alkenyloxy group which may have a substituent group, a $C_{1-6}$ alkylthio group which may have a substituent group, a $C_{2-6}$ alkenylthio group which may have a substituent group, a $C_{2-6}$ alkynylthio group which may have a substituent group, a substituted carbonyl group, an amino group which may have a substituent group, a $C_{1-6}$ alkylsulfonyl group which may have a substituent group, a $C_{2-6}$ alkenylsulfonyl group which may have a substituent group, a $C_{2-6}$ alkynylsulfonyl group which may have a substituent group, a $C_{1-6}$ alkylsulfinyl group which may have a substituent group, a $C_{2-6}$ alkenylsulfinyl group which may have a substituent group, a $C_{2-6}$ alkynylsulfinyl group which may have a substituent group, a formyl group, a $C_{3-8}$ cycloalkyl group which may have a substituent group, a $C_{3-8}$ cycloalkenyl group which may have a substituent group, a 5- to 14-membered non-aromatic heterocyclic group which may have a substituent group, a $C_{6-14}$ aromatic hydrocarbon cyclic group which may have a substituent group and a 5- to 14-membered aromatic heterocyclic group which may have a substituent group are preferred; (2) one or more groups selected from 1) hydroxyl group, 2) a halogen atom, 3) cyano group, 4) nitro group, 5) a $C_{1-6}$ alkyl group, $C_{2-6}$ alkenyl group or $C_{2-6}$ alkynyl group, each of which may be substituted with at least one group selected from (i) hydroxyl group, (ii) cyano group, (iii) halogen atom, (iv) $C_{1-6}$ alkylamino group, (v) di($C_{1-6}$ alkyl)amino group, (vi) $C_{2-6}$ alkenylamino group, (vii) di($C_{2-6}$ alkenyl)amino group, (viii) $C_{2-6}$ alkynylamino group, (ix) di($C_{2-6}$ alkynyl)amino group, (x) N—$C_{1-6}$ alkyl-N—$C_{2-6}$ alkenylamino group, (xi) N—$C_{1-6}$ alkyl-N—$C_{2-6}$ alkynylamino group, (xii) N—$C_{2-6}$ alkenyl-N—$C_{2-6}$ alkynylamino group, (xiii) aralkyloxy group, (xiv) TBDMS oxy group, (xv) $C_{1-6}$ alkylsulfonylamino group, (xvi) $C_{1-6}$ alkylcarbonyloxy group, (xvii) $C_{2-6}$ alkenylcarbonyloxy group, (xviii) $C_{2-6}$ alkynylcarbonyloxy group, (xix) N—$C_{1-6}$ alkylcarbamoyl group, (xx) N—$C_{2-6}$ alkenylcarbamoyl group and (xxi) N—$C_{1-6}$ alkynylcarbamoyl group, 6) a $C_{1-6}$ alkoxy group, $C_{2-6}$ alkenyloxy group or $C_{2-6}$ alkynyloxy group, each of which may be substituted with at least one group selected from (i) $C_{1-6}$ alkylamino group, (ii) aralkyloxy group and (iii) hydroxyl group, 7) a $C_{1-6}$ alkylthio group, $C_{2-6}$ alkenylthio group or $C_{2-6}$ alkynylthio group, each of which may be substituted with at least one group selected from (i) hydroxyl group, (ii) nitrile group, (iii) halogen atom, (iv) $C_{1-6}$ alkylamino group, (v) aralkyloxy group, (vi) TBDMS oxy group, (vii) $C_{1-6}$ alkylsulfonylamino group, (viii) $C_{1-6}$ alkylcarbonyloxy group and (ix) $C_{1-6}$ alkylcarbamoyl group, 8) a carbonyl group substituted with a group selected from (i) $C_{1-6}$ alkoxy group, (ii) amino group, (iii) $C_{1-6}$ alkylamino group, (iv) di($C_{1-6}$ alkyl) amino group, (v) $C_{2-6}$ alkenylamino group, (vi) di($C_{2-6}$ alkenyl) amino group, (vii) $C_{2-6}$ alkynylamino group, (vii) di ($C_{2-6}$ alkynyl) amino group, (viii) N—$C_{1-6}$ alkyl-N—$C_{2-6}$ alkenylamino group, (ix) N—$C_{1-6}$ alkyl-N—$C_{2-6}$ alkynylamino group and (x) N—$C_{2-6}$ alkenyl-N—$C_{2-6}$ alkynylamino group, 9) an amino group which may be substituted with one or two groups selected from (i) $C_{1-6}$ alkyl group, (ii) $C_{2-6}$ alkenyl group, (iii) $C_{2-6}$ alkynyl group, (iv) $C_{1-6}$ alkylsulfonyl group, (v) $C_{2-6}$ alkenylsulfonyl group, (vi) $C_{2-6}$ alkynylsulfonyl group, (vii) $C_{1-6}$ alkylcarbonyl group, (viii) $C_{2-6}$ alkenylcarbonyl group and (ix) $C_{2-6}$ alkynylcarbonyl group, 10) a $C_{1-6}$ alkylsulfonyl group, 11) a $C_{2-6}$ alkenylsulfonyl group, 12) a $C_{2-6}$ alkynylsulfonyl group, 13) a $C_{1-6}$ alkylsulfinyl group, 14) a $C_{2-6}$ alkenylsulfinyl group, 15) a $C_{2-6}$ alkynylsulfinyl group, 16) formyl group, 17) a $C_{3-8}$ cycloalkyl group or $C_{3-8}$ cycloalkenyl group, each of which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, 18) a 5- to 14-membered non-aromatic heterocyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, 19) a $C_{6-14}$ aromatic hydrocarbon cyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, and 20) a 5- to 14-membered aromatic heterocyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group are more preferred; and (3) one or more groups selected from hydroxy group, a halogen atom (for example, fluorine atom, chlorine atom, bromine atom, iodine atom, etc.), cyano group, nitro group, a $C_{1-6}$ alkyl group (for example, methyl group, ethyl group, n-propyl group, iso-propyl group, n-butyl group, iso-butyl group, tert-butyl group, n-pentyl group, i-pentyl group, neopentyl group, n-hexyl group, etc.), a $C_{2-6}$ alkenyl group (for example, vinyl group, allyl group, 1-propenyl group, isopropenyl group, etc.), a $C_{2-6}$ alkynyl group (for example, ethynyl group, 1-propynyl group, 2-propynyl group, butynyl group, pentynyl group, hexynyl group, etc.), a $C_{1-6}$ alkoxy group (methoxy group, ethoxy group, n-propoxy group, iso-propoxy group, n-butoxy group, etc.) and a $C_{2-6}$ alkenyloxy group (vinyloxy group, allyloxy group, 1-propenyloxy group, isopropenyloxy group, etc.) are the most preferred.

The preferable mode of the compound represented by the formula (I) above according to the present invention or a salt thereof is not particularly limited, among which more preferable mode is a compound or a salt thereof, wherein $R^3$ is a group represented by the formula:

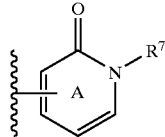

(wherein $R^7$ represents a group selected from the above substituent group b; and ring A represents a nitrogen-containing 6-membered ring which may be substituted with 1 to 4 groups selected from the above substituent group b), and still more preferable mode is a compound represented by the formula:

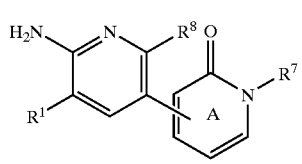

(II)'

(wherein $R^1$ represents cyano group, carboxyl group or an optionally substituted carbamoyl group; $R^2$ represents hydrogen atom, hydroxyl group, a $C_{1-6}$ alkoxy group which may have a substituent group, a $C_{1-6}$ alkylthio group which may have a substituent group, a $C_{6-14}$ aromatic hydrocarbon cyclic group which may have a substituent group or a 5- to 14-membered aromatic heterocyclic group which may have a substituent group; $R^7$ represents a group selected from the above substituent group b; $R^8$ represents a $C_{6-14}$ aromatic hydrocarbon cyclic group or a 5- to 14-membered aromatic heterocyclic group, each of which may have a substituent group; ring A represents a nitrogen-containing 6-membered ring which may be substituted with 1 to 4 groups selected from the substituent group b above) or a salt thereof. The preferable mode of each $R^1$, $R^7$ and $R^8$ are as described above.

In this specification, the "salt" is not particularly limited insofar as it forms a salt with the compound accroding to the present invenvention and is pharmacologically acceptable. Preferably, hydrogen halides (for example, hydrofluoride, hydrochloride, hydrobromide and hydroiodide), inorganic acid salts (for example, sulfate, nitrate, perchlorate, phosphate, carbonate and bicarbonate), organic carboxylic acid salts (for example, acetate, trifluoroacetate, oxalate, maleate, tartrate, fumarate and citrate), organic sulfonic acid salts (for example, methanesulfonate, trifluoromethanesulfonate, ethanesulfonate, benzenesulfonate, toluenesulfonate and camphor sulfonate), amino acid salts (for example, aspartate and glutamate), quaternary amine salts, alkali metal salts (for example, sodium salt and potassium salt), alkaline earth metal salts (for example, magnesium salt and calcium salt), etc. may be proposed., and hydrochloride, oxalte etc. are more preferred as the "pharmacologically acceptable salt".

Production Process

A typical process for producing the compound according to the present invention represented by the above formula (I) will be shown below. Here, the "room temperature" mentioned below refers to 0 to around 40° C.

Production Process 1

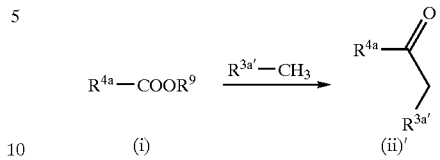

(i)    (ii)'

In the formula, $R^{3a'}$ represents a 5- to 14-membered aromatic heterocyclic group which has a nitrogen atom at the 4-position and may have a substituent group (for example, 4-pyridyl group, 4-pyrimidinyl group, 4-pyridazinyl group, etc.); $R^{4a}$ represents a $C_{6-14}$ aromatic hydrocarbon cyclic group which may have a substituent group or a 5- to 14-membered aromatic heterocyclic group which may have a substituent group; and $R^9$ represents a $C_{1-8}$ alkyl group. The 1,2-biaryl-1-ethanone compound (ii)' as the starting material of the compound represented by the above formula (I) according to the present invention can be produced by reacting the aromatic carboxylate (i) with a 4-methyl aromatic heterocyclic compound represented by the formula $R^{3a'}$—$CH_3$ in the presence of a base in a solvent, followed by dealcoholic condensation. The base used varies depending on the starting material, the solvent used etc., and is not particularly limited so long as it is inert to the reaction. Preferably, secondary amine metal salts represented by lithium bis(trimethylsilyl)amide and lithium diisopropylamide may be proposed. The solvent used varies depending on the starting material, reagents etc., and is not particularly limited insofar as it is inert to the reaction and dissolves the starting material to a certain degree. Preferably, ethers such as tetrahydrofuran, dioxane, dimethoxyethane or diethylene glycol may be proposed. The reaction temperature is usually −78° C. to room temperature, preferably around 0° C.

Production Process 2

$$R^{4a}—CHO \xrightarrow{R^{3b''}—CH_2X^1}$$

(iii)    (ii)''

In the formula, $R^{3a''}$ represents a $C_{6-14}$ aromatic hydrocarbon cyclic group which may have a substituent group or a 5- to 14-membered aromatic heterocyclic group which may have a substituent group; $R^{4a}$ has the same meaning as defined above; and $X^1$ represents a halogen atom, an alkylsulfonyloxy group or an arylsulfonyloxy group. The 1,2-biaryl-1-ethanone compound (ii)'' as the starting material for producing the compound represented by the above formula (I) according to the present invention can also be produced by Production Process 2 instead of the above-mentioned Production Process 1. That is, it is produced by allowing an aromatic trialkylsilyl cyanohydrin compound prepared from the aromatic aldehyde (iii) to be condensed with a compound represented by the formula $R^{3a'''}$—$CH_2X^1$ in the presence of a base; and then allowing a fluorine compound to act, followed by decyanating trialkylsilylation. As the reagent used for preparing the aromatic trialkylsilyl cyanohydrin from (iii), using a trialkylsilyl cyanide compound represented by trimethylsilyl cyanide is preferred. In this case, simultaneously using a metal salt such as zinc (II) iodide as a catalyst is also preferred, and it makes possible to achieve rapid reaction. The base used varies depending on the starting material, the solvent used etc., and is not particularly limited so long as it is inert to the reaction. Preferably, secondary amine metal salts represented by lithium bis(trimethylsilyl)amide and lithium diisopropylamide, etc. may be proposed. The fluorine compound used varies depending on the starting material, the solvent used etc., and is not particularly limited so long as it is inert to the reaction. Preferably, hydrofluoric acid, hydrofluoride amine, and more preferably tetrabutylammonium fluoride may be proposed. The solvent used varies depending on the starting material, reagents etc., and is not particularly limited insofar as it is inert to the reaction and dissolves the starting material to a certain degree. Preferably, ethers such as tetrahydrofuran, dioxane, dimethoxyethane or diethylene glycol may be proposed. The reaction temperature is preferably −78° C. to room temperature.

Production Process 3

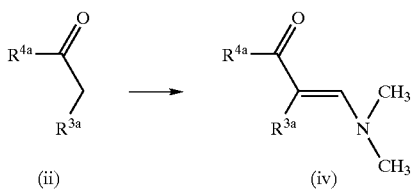

In the formula, $R^{3a}$ and $R^{4a}$ represent a $C_{6-14}$ aromatic hydrocarbon cyclic group which may have a substituent group or a 5- to 14-membered aromatic heterocyclic group which may have a substituent group. The 3-(dimethylamino)-2-propen-1-one derivative (iv) is the starting material for producing the compound (I) according to the present invention. (iv) can be produced by allowing N,N-dimethylformamide dimethylacetal to act on active methylene of (ii) produced in the above-mentioned Production Process 1 or 2. This reaction is carried out most preferably in the absence of a solvent, but preferable results can be achieved even if it is carried out by diluting with a solvent which is inert to the reaction and dissolves the starting material to a certain degree (for example, N,N-dimethylformamide, tetrahydrofuran, dioxane, N,N-methylpyrrolidone, benzene, toluene etc.), etc. The reaction temperature is usually room temperature to 120° C., more preferably around 100° C.

Using the compounds obtained in the above-mentioned Production Processes 1 to 3, the compound (vii) according to the present invention can be produced as follows.

Production Process 4

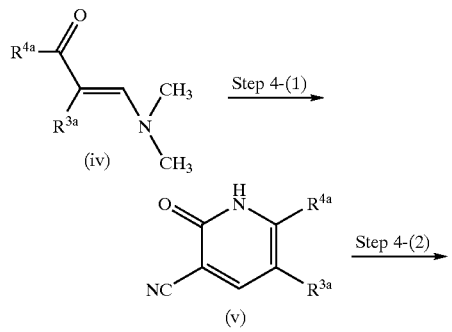

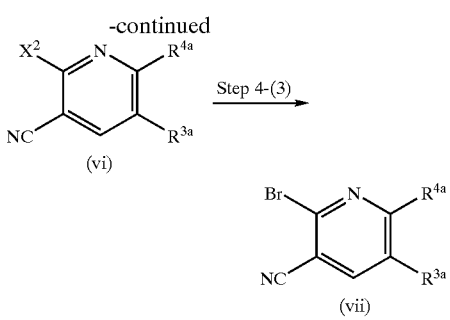

In the formula, $R^{3a}$ and $R^{4a}$ have the same meanings as defined above; and $X^2$ represents a halogen atom. The compound (vii) can be produced via the intermediates (v) and (vi) in this order from the compound (iv) obtained in the above-mentioned Production Process 3 (steps 4-(1) to 4-(3) in the formula). The 2-oxo-1,2-dihydro-3-pyridylcarbonitrile derivative (v) can be produced by reacting (iv) with 2-cyanoacetamide in the presence of a base (step 4-(1)). The base used varies depending on the starting material, the solvent used etc., and is not particularly limited insofar as it is inert to the reaction. Preferably, an alkali metal alkoxide such as sodium methoxide, sodium ethoxide or potassium tert-butoxide may be proposed. Further, also by using alkali metal carbonates such as potassium carbonate or sodium carbonate, a preferable result can be obtained. The solvent used varies depending on the starting material, reagents etc., and is not particularly limited insofar as it is inert to the reaction and dissolves the starting material to a certain degree. Preferably, N,N-dimethylformamide, N-methylpyrrolidone, dimethyl sulfoxide, methanol, ethanol etc. may be proposed. The reaction temperature is usually room temperature to 120° C., more preferably around 80° C. The 2-halogeno-3-pyridylcarbonitrile derivative (vi) can be produced by converting an oxo group in (v) into a halogen atom (step 4-(2)). The reaction is conducted preferably in the absence of a solvent. Further, when it is conducted by being suspending in a solvent which is inert to the reaction and dissolves the starting material to a certain degree (for example, acetonitrile, dioxane, tetrahydrofuran etc.), a preferable result can be also obtained. The halogenating agent used for converting the oxo group into a halogen atom varies depending on the starting material, the solvent used etc., and is not particularly limited so long as it is inert to the reaction. Preferably, phosphorus oxychloride, phosphorus oxybromide etc. may be proposed. It is preferably conducted by acting these halogenating agent at a reaction temperature of 70 to 120° C. Further, when a tertiary amine such as tripropylamine, a quaternary amine salt such as tetraethyl ammonium chloride, or N,N-dimethylformamide etc., is added to this reaction system, the reaction is further promoted and a good result can be obtained. The 2-amino-3-pyridylcarbonitrile compound (vii) according to the present invention can be produced by reacting $X^2$ (halogen atom) in (vi) with ammonia (step 4-(3)). The present reaction is carried out usually at 0 to 150° C., more preferably in an autoclave (50 to 100° C.). The solvent used varies depending on the starting material, reagents etc., and is not particularly limited insofar as it is inert to the reaction and dissolves the starting material to a certain degree. Preferably, alcohols such as methanol or ethanol, ethers such as tetrahydrofuran, dioxane, dimethoxyethane or diethylene glycol dimethyl ether, N,N-dimethylformamide, 1-methyl pyrrolidinone etc. may be proposed.

Production Process 5

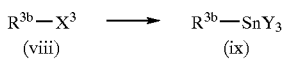

In the formula, $R^{3b}$ represents a $C_{6-14}$ aromatic hydrocarbon cyclic group which may have a substituent group or a 5- to 14-membered aromatic heterocyclic group which may have a substituent group; $X^3$ represents a halogen atom; and Y represents a $C_{1-6}$ alkyl group. The aryl tin reagent (ix) used in the "step 6-(4)" in Production Process 6 can be produced by lithiation of an aryl halide (viii); and then allowing halogenotrialkyl tin to act. In the lithiation reaction, use of alkyl lithium such as n-butyl lithium, sec-butyl lithium, tert-butyl lithium etc. is preferred. The halogenotrialkyl tin used varies depending on the starting material, the solvent used etc., and is not particularly limited so long as it is inert to the reaction. Preferably, trimethyltin chloride such as chlorotributyltin, or triethyltin bromide etc. may be proposed. The solvent used varies depending on the starting material, reagents etc., and is not particularly limited insofar as it is inert to the reaction and dissolves the starting material to a certain degree. Preferably, an ether such as tetrahydrofuran, diethyl ether etc. may be proposed. The reaction temperature is preferably $-100°$ C. to room temperature.

When the 3-(dimethylamino)-2-propen-1-one derivative obtained by subjecting the compound (acetylated aryl or acetylated heteroaryl represented by the formula $R^{4a}$—$COCH_3$) wherein $R^{3a}$ in (ii) was replaced by a hydrogen atom to the reaction in Production Process 3, is further subjected to "step 4-(1)" in Production Process 4, the compound (x) wherein $R^{3a}$ in (v) was replaced by a hydrogen atom is obtained. The method of producing the compound (xiv) according to the present invention from the compound (x) is shown below.

Production Process 6

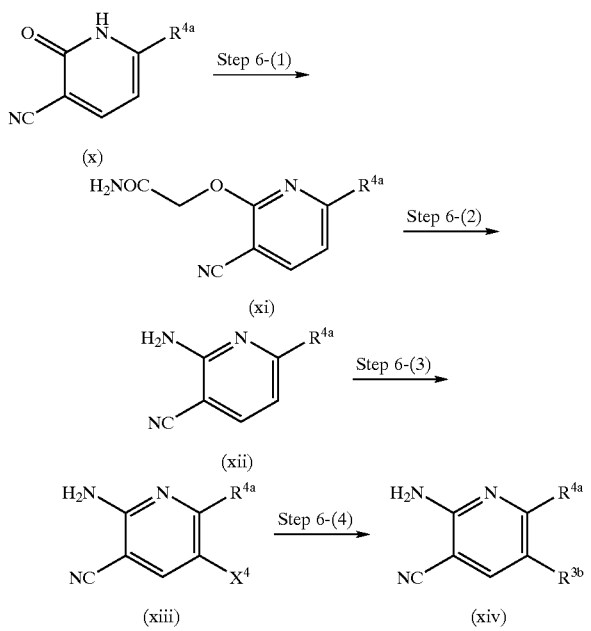

In the formula, $R^{3b}$ and $R^{4a}$ have the same meanings as defined above; and $X^4$ represents a halogen atom. The compound (xiv) according to the present invention can be produced from (x) through steps 6-(1) to 6-(4) (intermediates (xi) to (xiii)). The compound (xi) can be produced by alkylating an oxygen atom at the 2-position in (x) with 2-halogenoacetamide in the presence of a base (step 6-(1)). The 2-halogenoacetamide used varies depending on the starting material, the solvent used etc., and is not particularly limited so long as it is inert to the reaction. The reaction conducted by using 2-chloroacetamide is preferred, and conducted by further adding sodium iodide is more preferred. The base used varies depending on the starting material, the solvent used etc., and is not particularly limited so long as it is inert to the reaction. Preferably, sodium hydride, sodium hydroxide, potassium hydroxide, sodium bicarbonate, sodium carbonate and potassium carbonate may be proposed. The solvent used varies depending on the starting material, reagents etc., and is not particularly limited insofar as it is inert to the reaction and dissolves the starting material to a certain degree. Preferably, ketones such as acetone or methyl ethyl ketone, alcohols such as methanol or ethanol, ethers such as tetrahydrofuran, dioxane, dimethoxyethane or diethylene glycol dimethyl ether, N,N-dimethylformamide, dimethyl sulfoxide, 1-methyl pyrrolidinone etc. may be proposed. The reaction temperature is usually 0 to 100° C. The compound (xii) can be produced by transaminating the 2-aminocarbonylmethyloxy-3-cyanopyridine derivative (xi) in the presence of a base in a solvent (step 6-(2)). The base used varies depending on the starting material, the solvent used etc., and is not particularly limited so long as it is inert to the reaction. Preferably, sodium hydride, sodium hydroxide, potassium hydroxide, sodium bicarbonate, sodium carbonate, potassium carbonate etc. may be proposed. The solvent used varies depending on the starting material, reagents etc. and is not particularly limited insofar as it is inert to the reaction and dissolves the starting material to a certain degree. Preferably, ketones such as acetone or methyl ethyl ketone, alcohols such as methanol, ethanol, propanol or butanol, ethers such as tetrahydrofuran, dioxane, dimethoxyethane or diethylene glycol dimethyl ether, N,N-dimethylformamide, dimethyl sulfoxide, 1-methyl pyrrolidinone etc. may be proposed. The reaction temperature is usually room temperature to 150° C. The compound (xiii) can be produced by halogenating the 5-position of the pyridine ring in the 2-aminonicotinonitrile derivative (xii) with a halogenating agent in a solvent (step 6-(3)). As the halogenating agent used, N-bromosuccinimide, bromine etc. are preferred. The solvent used varies depending on the starting material, reagents etc., and is not particularly limited insofar as it is inert to the reaction and dissolves the starting material to a certain degree. Preferably, alcohols such as methanol or ethanol, ethers such as tetrahydrofuran, dioxane, dimethoxyethane or diethylene glycol dimethyl ether, N,N-dimethylformamide, 1-methyl pyrrolidinone etc. may be proposed. The reaction temperature is usually $-20°$ C. to room temperature. The compound (xiv) according to the present invention can be produced by allowing the aryl tin reagent obtained in Production Process 5 to act on the 2-amino-5-halogenonicotinonitrile derivative (xiii) in the presence of a palladium catalyst in a solvent to introduce an aromatic group into the 5-position of the pyridine ring in (xiii) (step 6-(4)). The palladium catalyst used varies depending on the starting material, the solvent used etc., and is not particularly limited so long as it is inert to the reaction. Preferably, dichlorobis(triphenylphoshine) palladium (II), palladium (II) acetate, tetrakis (triphenylphosphine) palladium (0), tris(dibenzylidene acetone) dipalladium (0) etc. may be proposed. The solvent used varies depending on the starting material, reagents etc., and is not particularly limited insofar as it is inert to the reaction and dissolves the starting material to a certain degree. Preferably, alcohols such as methanol or ethanol, ethers such as tetrahydrofuran, dioxane, dimethoxyethane or diethylene glycol dimethyl ether, toluene, xylene, N,N-dimethylformamide, 1-methyl pyrrolidinone etc. may be proposed. The reaction temperature is usually room temperature to 150° C.

Out of the compounds represented by the above formula (I) according to the present invention, those compounds wherein $R^2$, $R^3$ and/or $R^4$ represent an α-hydroxy nitrogen-containing aromatic heterocyclic group having a hydroxyl group at the α-position of the nitrogen atom can be produced as follows.

For example, the compound (xvi) having an α-hydroxy nitrogen-containing aromatic heterocyclic group at the 5-position of the pyridine ring can be produced by hydrolysis of the α-alkoxy nitrogen-containing aromatic heterocyclic compound (xv).

Production Process 7

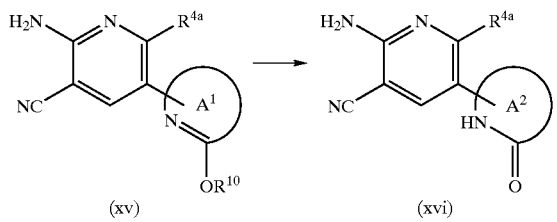

In the formula, $R^{4a}$ has the same meaning as defined above; $R^{10}$ represents a $C_{1-6}$ alkyl group, a $C_{2-6}$ alkenyl group, a $C_{2-6}$ alkynyl group etc.; the ring $A^1$ represents a pyridinyl group, pyrimidyl group and pyrazinyl group; and the ring $A^2$ represents a dihydrooxopyridinyl group, a dihydrooxopyrimidyl group, a dihydropyrazinyl group or a tetrahydropyrazinyl group. The reaction is carried out preferably in an aqueous solution of a mineral acid such as, for example, hydrochloric acid, hydrobromic acid or sulfuric acid, or in a mixed solvent of the above-mentioned aqueous solution of the mineral acid and acetic acid. The reaction temperature is usually room temperature to 100° C.

Further, a substituent can be introduced into the α-hydroxy nitrogen-containing aromatic heterocyclic ring in the compound (xvi) according to the present invention obtained by the above-mentioned Production Process 7, by the following method.

Production Process 8

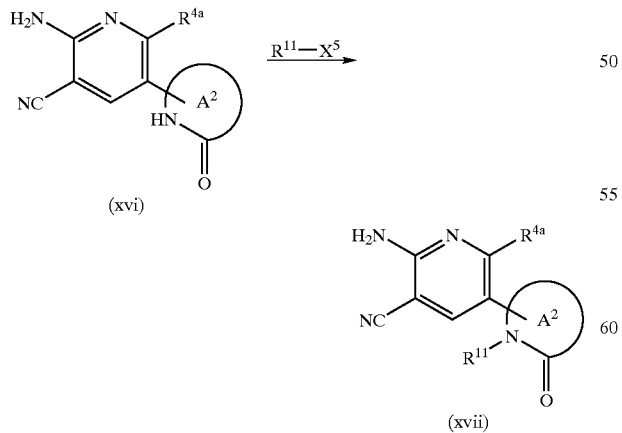

In the formula, $R^{4a}$ and ring $A^2$ have the same meanings as defined above; $R^{11}$ represents a $C_{1-6}$ alkyl group, a $C_{2-6}$ alkenyl group, a $C_{2-6}$ alkynyl group etc.; and $X^5$ represents a halogen atom. According to this process, (xvi) is reacted with an alkyl halide compound etc. in the presence of a base in a solvent, whereby the compound (xvii) having a substituent group introduced into the nitrogen atom on the ring $A^2$ can be produced. The base used varies depending on the starting material, the solvent used etc., and is not particularly limited so long as it is inert to the reaction. Preferably, sodium hydride, sodium hydroxide, potassium hydroxide, sodium bicarbonate, sodium carbonate and potassium carbonate may be proposed. The solvent used varies depending on the starting material, reagents etc., and is not particularly limited insofar as it is inert to the reaction and dissolves the starting material to a certain degree. Preferably, alcohols such as methanol or ethanol, ethers such as tetrahydrofuran, dioxane, dimethoxyethane or diethylene glycol dimethyl ether, N,N-dimethylformamide, dimethyl sulfoxide, 1-methyl pyrrolidinone, etc. may be proposed. The reaction temperature is usually 0 to 100° C.

Production Process 9

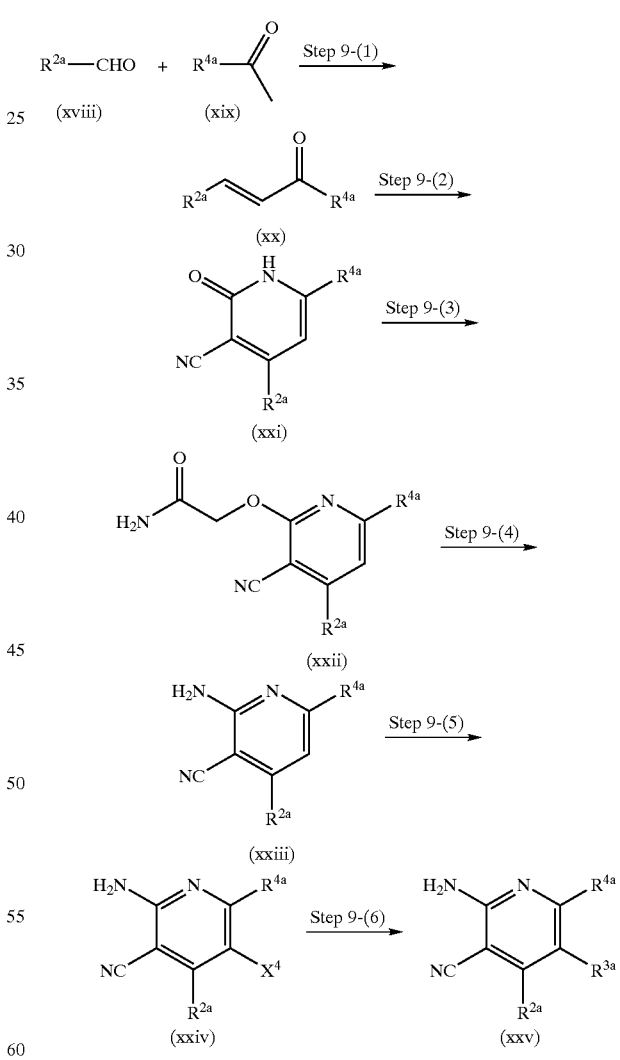

In the formula, $R^{3a}$, $R^{4a}$ and $X^4$ have the same meanings as defined above; and $R^{2a}$ represents a $C_{6-14}$ aromatic hydrocarbon cyclic group which may have a substituent group or a 5- to 14-membered aromatic heterocyclic group which may have a substituent group. The compound (xxv) according to the present invention can be produced from (xviii) and (xix) through steps 9-(1) to 9-(6) (intermediates (xx) to (xxiv)). The compound (xx) can be produced by dehydrating condensation of (xviii) and (xix) in the presence of a base (step 9-(1)). The base used in the reaction varies depending on the starting material, the solvent used etc., and is not particularly limited so long as it is inert to the reaction. Preferably, inorganic salts such as potassium hydroxide or sodium hydroxide may be proposed. The solvent used varies depending on the starting material, reagents etc., and is not particularly limited insofar as it is inert to the reaction and dissolves the starting material to a certain degree. Preferably, a mixed solvent of an alcohol such as ethanol and water may be proposed. The 2-oxo-1,2-dihydro-3-pyridylcarbonitrile derivative (xxi) can be produced by reacting (xx) with 2-cyanoacetamide in the presence of a base (step 9-(2)). The reaction can be promoted in an oxygen atmosphere. The base used varies depending on the starting material, the solvent used etc., and is not particularly limited insofar as the reaction is not inhibited. Preferably, an alkali metal alkoxide such as sodium methoxide, sodium ethoxide or potassium tert-butoxide may be proposed. Otherwise, using alkali metal carbonates such as potassium carbonate or sodium carbonate can also bring about a preferable result. The solvent used varies depending on the starting material, reagents etc., and is not particularly limited insofar as it is inert to the reaction and dissolves the starting material to a certain degree. Preferably, N,N-dimethylformamide, N-methylpyrrolidone, dimethyl sulfoxide, methanol, ethanol etc. may be proposed. The reaction temperature is preferably room temperature to 120° C., more preferably around room temperature. The compound (xxii) can be produced by alkylating an oxygen atom at the 2-position in (xxi) with 2-halogenoacetamide in the presence of a base (step 9-(3)). The 2-halogenoacetamide used varies depending on the starting material, the solvent used etc., and is not particularly limited so long as it is inert to the reaction. The reaction conducted by using 2-chloroacetamide is preferred, and conducted by further adding sodium iodide is more preferred. The base used varies depending on the starting material, the solvent used etc., and is not particularly limited so long as it is inert to the reaction. Preferably, sodium hydride, sodium hydroxide, potassium hydroxide, sodium bicarbonate, sodium carbonate and potassium carbonate may be proposed. The solvent used varies depending on the starting material, reagents etc., and is not particularly limited insofar as it is inert to the reaction and dissolves the starting material to a certain degree. Preferably, ketones such as acetone or methyl ethyl ketone, alcohols such as methanol or ethanol, ethers such as tetrahydrofuran, dioxane, dimethoxyethane or diethylene glycol dimethyl ether, N,N-dimethylformamide, dimethyl sulfoxide, 1-methyl pyrrolidinone etc. may be proposed. The reaction temperature is usually 0 to 100° C. The compound (xxiii) can be produced by transaminating the 2-aminocarbonylmethyloxy-3-cyanopyridine derivative (xxii) in the presence of a base in a solvent (step 9-(4)). The base used varies depending on the starting material, the solvent used etc., and is not particularly limited so long as it is inert to the reaction. Preferably, for example, sodium hydride, sodium hydroxide, potassium hydroxide, sodium bicarbonate, sodium carbonate, potassium carbonate etc. may be proposed. The solvent used varies depending on the starting material, reagents etc., and is not particularly limited insofar as it is inert to the reaction and dissolves the starting material to a certain degree. Preferably, N,N-dimethylformamide, dimethyl sulfoxide, 1-methylpyrrolidinone etc. may be proposed, other than ketones such as acetone or methyl ethyl ketone, alcohols such as methanol, ethanol, propanol or butanol, ethers such as tetrahydrofuran, dioxane, dimethoxyethane or diethylene glycol dimethyl ether maybe proposed. The reaction temperature is usually room temperature to 150° C. The compound (xxiv) can be produced by halogenating the 5-position of the pyridine ring in the 2-aminonicotinonitrile derivative (xxiii) with a halogenating agent in a solvent (step 9-(5)). The halogenating agent used varies depending on the starting material, the solvent used etc., and is not particularly limited so long as it is inert to the reaction. Preferably, N-bromosuccinimide, bromine etc. may be proposed. Further, the solvent used varies depending on the starting material, reagents etc., and is not particularly limited insofar as it inert to the reaction and dissolves the starting material to a certain degree. Preferably, alcohols such as methanol or ethanol, ethers such as tetrahydrofuran, dioxane, dimethoxyethane or diethylene glycol dimethyl ether, N,N-dimethylformamide, 1-methyl pyrrolidinone etc. may be proposed. The reaction temperature is usually −20° C. to room temperature. The compound (xxv) according to the present invention can be produced by reacting the 2-amino-5-halogenonicotinonitrile derivative (xxiv) with the aryl tin reagent obtained in Production Process 5 in the presence of a palladium catalyst in a solvent, to introduce an aromatic group into the 5-position of the pyridine ring in (xxiv) (step 9-(6)). The palladium catalyst used varies depending on the starting material, the solvent used etc., and is not particularly limited so long as it is inert to the reaction. Preferably, dichlorobis (triphenylphoshine) palladium (II), palladium (II) acetate, tetrakis(triphenylphosphine) palladium (0), tris (dibenzylidene acetone) dipalladium (0), dichlorobis (acetonitrile) palladium (II) etc. may be proposed. Further, the solvent used varies depending on the starting material, reagents etc., and is not particularly limited insofar as it is inert to the reacton and dissolves the starting material to a certain degree. Preferably, alcohols such as methanol, ethanol, propanol or butanol, ethers such as tetrahydrofuran, dioxane, dimethoxyethane or diethylene glycol dimethyl ether, toluene, xylene, N,N-dimethylformamide, 1-methyl pyrrolidinone etc. may be proposed The reaction temperature is usually room temperature to 150° C.

Production Process 10

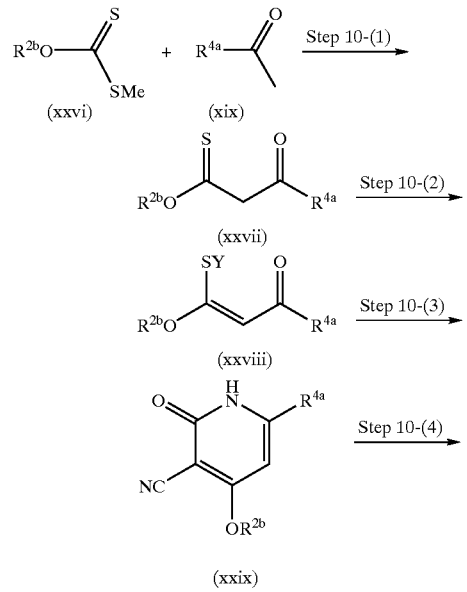

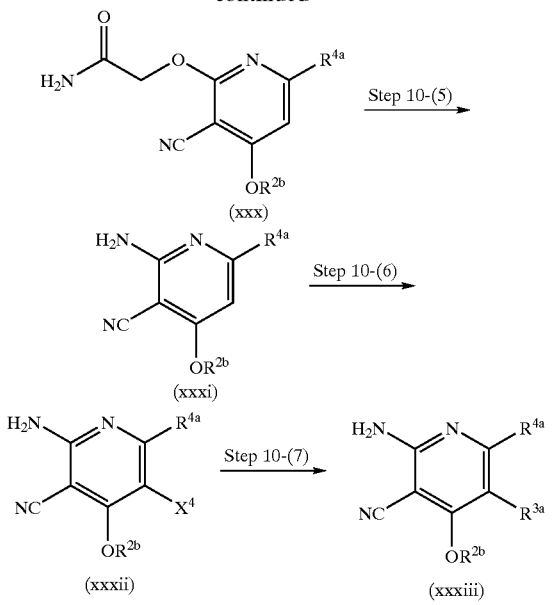

In the formula, $R^{3a}$, $R^{4a}$ and $X^4$ have the same meanings as defined above; $R^{2b}$ represents an optionally substituted alkyl group; and Y represents a lower alkyl group. The compound (xxxiii) according to the present invention can be produced from (xxvi) and (xix) through steps 10-(1) to 10-(7) (intermediates (xxvii) to (xxxii)). The compound (xxvii) can be produced by condensation of (xxvi) with (xix) (step 10-(1)). The base used varies depending on the starting material, the solvent used etc., and is not particularly limited so long as it is inert to the reaction. Preferably, potassium tert-butoxide etc. may be proposed. The solvent used varies depending on the starting material, reagents etc., and is not particularly limited insofar as it is inert to the reaction and dissolves the starting material to a certain degree. tert-Butanol is preferred. The reaction temperature is preferably room temperature to 120° C., more preferably around room temperature. The compound (xxxviii) can be produced by alkylating (xxvii) with methyl halide in the presence of a base (step 10-(2)). The base used in the reaction varies depending on the starting material, the solvent used etc., and is not particularly limited so long as it is inert to the reaction. Preferably, an inorganic base such as potassium carbonate etc. may be proposed. Preferable example of the methyl halide is methyl iodide. The solvent used varies depending on the starting material, reagents etc., and is not particularly limited insofar as it is inert to the reaction and dissolves the starting material to a certain degree. Preferably, a ketone such as acetone or methyl ethyl ketone may be proposed. The reaction temperature is preferably room temperature to 12° C, more preferably around room temperature. The 2-oxo-1,2-dihydro-3-pyridyl carbonitrile derivative (xxix) can be produced by reacting (xxviii) with 2-cyanoacetamide in the presence of a base (step 10-(3)). The base used varies depending on the starting material, the solvent used etc., and is not particularly limited so long as it is inert to the reaction. Preferably, an alkali metal alkoxide such as sodium methoxide, sodium ethoxide, sodium isopropoxide, potassium tert-butoxide etc. may be proposed. The solvent used varies depending on the starting material, reagents etc., and is not particularly limited insofar as it is inert to the reaction and dissolves the starting material to a certain degree. Preferably, N,N-dimethylformamide, N-methylpyrrolidone, dimethyl sulfoxide, isopropanol etc. The reaction temperature is preferably 0° C. to 120° C. The compound (xxx) can be produced by alkylating an oxygen atom at the 2-position of (xxix) with 2-halogenoacetamide in the presence of a base (step 10-(4)) As the 2-halogenoacetamide used, 2-chloroacetamide is preferred, and the reaction in which sodium iodide is further added is more preferred. The base used varies depending on the starting material, the solvent used etc., and is not particularly limited so long as it is inert to the reaction. Preferably, sodium hydride, sodium hydroxide, potassium hydroxide, sodium bicarbonate, sodium carbonate and potassium carbonate may be proposed. The solvent used varies depending on the starting material, reagents etc., and is not particularly limited so long as it is inert to the reaction and dissolves the starting material to a certain degree. Preferably, ketones such as acetone or methyl ethyl ketone, alcohols such as methanol or ethanol, ethers such as tetrahydrofuran, dioxane, dimethoxyethane or diethylene glycol dimethyl ether, N,N-dimethylformamide, dimethyl sulfoxide, 1-methyl pyrrolidinone, etc. may be proposed. The reaction temperature is usually 0 to 100° C. The compound (xxxi) can be produced by transaminating the 2-aminocarbonylmethyloxy-3-cyanopyridine derivative (xxx) in the presence of a base in a solvent (step 10-(5)). The base used varies depending on the starting material, the solvent used etc., and is not particularly limited so long as it is inert to the reaction. Preferably, sodium hydride, sodium hydroxide, potassium hydroxide, sodium bicarbonate, sodium carbonate, potassium carbonate etc. may be proposed. The solvent used varies depending on the starting material, the solvent used etc., and is not particularly limited unless it is inert to the reaction. Preferably, ketones such as acetone or methyl ethyl ketone, alcohols such as methanol, ethanol, propanol or butanol, ethers such as tetrahydrofuran, dioxane, dimethoxyethane or diethylene glycol dimethyl ether, N,N-dimethylformamide, dimethyl sulfoxide, 1-methyl pyrrolidinone, etc. may be proposed. The reaction temperature is usually room temperature to 150° C. The compound (xxii) can be produced by halogenating the 5-position of the pyridine ring in the 2-aminonicotinonitrile derivative (xxxi) with a halogenating agent in a solvent (step 10-(6)). The halogenating agent used varies depending on the starting material, the solvent used etc., and is not particularly limited so long as it is inert to the reaction. Preferably, N-bromosuccinimide, bromine etc. may be proposed. The solvent used varies depending on the starting material, reagents etc., and is not particularly limited insofar as it is inert to the reaction and dissolves the starting material to a certain degree. Preferably, alcohols such as methanol or ethanol etc., ethers such as tetrahydrofuran, dioxane, dimethoxyethane or diethylene glycol dimethyl ether etc., N,N-dimethylformamide, 1-methyl pyrrolidinone etc. may be proposed. The reaction temperature is usually −20° C. to room temperature. The compound (xxxiii) according to the present invention can be produced by allowing the aryl tin reagent obtained in Production Process 5 to act on the 2-amino-5-halogenonicotinonitrile derivative (xxxii) in the presence of a palladium catalyst in a solvent, to introduce an aromatic group into the 5-position of the pyridine ring in (xxxii) (step 10-(7)). As the palladium catalyst used is, for example, dichlorobis(triphenylphoshine) palladium (II), palladium (II) acetate, tetrakis(triphenylphosphine) palladium (0), tris(dibenzylidene acetone) dipalladium (0), dichlorobis (acetonitrile) palladium (II) etc. are preferred. The solvent used varies depending on the starting material, reagents etc., and is not particularly limited insofar as it is inert to the reaction and dissolves the starting material to a certain degree. Preferably, alcohols such as methanol or ethanol, ethers such as tetrahydrofuran, dioxane, dimethoxyethane or diethylene glycol dimethyl ether, toluene, xylene, N,N-dimethylformamide, 1-methyl pyrrolidinone etc. may be proposed. The reaction temperature is usually room temperature to 150° C.

Production Process 11

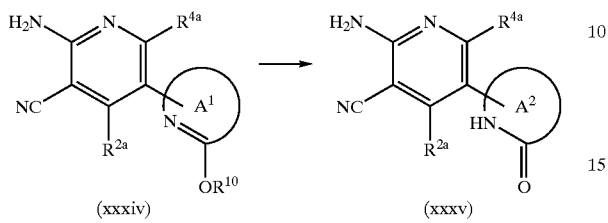

(xxxiv) (xxxv)

In the formula, $R^{2a}$ and $R^{4a}$ have the same meanings as defined above; $R^{10}$ represents a $C_{1-6}$ alkyl group, a $C_{2-6}$ alkenyl group, a $C_{2-6}$ alkynyl group etc.; the ring $A^1$ represents a pyridinyl group, a pyrimidyl group or a pyrazinyl group; and the ring $A^2$ represents a dihydrooxopyridinyl group, a dihydrooxopyrimidyl group, a dihydropyrazinyl group or a tetrahydropyrazinyl group. The compound (xxxv) having an α-hydroxy nitrogen-containing aromatic heterocyclic group at the 5-position of the pyridine ring can be produced by hydrolyzing the α-alkoxy nitrogen-containing aromatic heterocyclic compound (xxxiv). The solvent used in this reaction varies depending on the starting material, reagents etc., and is not particularly limited insofar as it is inert to the reaction and dissolves the starting material to a certain degree. Preferably, an aqueous solution of a mineral acid such as hydrochloric acid, hydrobromic acid or sulfuric acid, or a mixed solvent of the above-mentioned aqueous solution of the mineral acid and acetic acid may be proposed. The reaction temperature is usually room temperature to 100° C.

Production Process 12

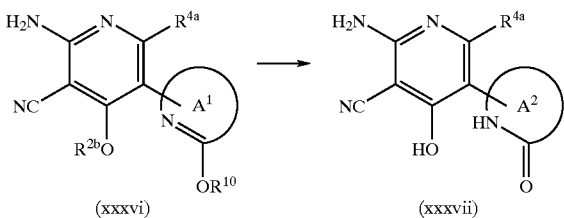

(xxxvi) (xxxvii)

In the formula, $R^{2b}$, $R^{4a}$, the ring $A^1$ and the ring $A^2$ have the same meanings as defined above; and $R^{10}$ represents a $C_{1-6}$ alkyl group, a $C_{2-6}$ alkenyl group, a $C_{2-6}$ alkynyl group, etc. The compound (xxxvii) having an α-hydroxy nitrogen-containing aromatic heterocyclic group at the 5-position of the pyridine ring can be produced by hydrolyzing the α-alkoxy nitrogen-containing aromatic heterocyclic compound (xxxvi). The solvent used in this reaction varies depending on the starting material, reagents etc., and is not particularly limited insofar as it is inert to the reaction and dissolves the starting material to a certain degree. Preferably, an aqueous solution of a mineral acid such as hydrochloric acid, hydrobromic acid or sulfuric acid, or a mixed solvent of the above-mentioned aqueous solution of the mineral acid and acetic acid may be proposed. The reaction temperature is usually room temperature to 100° C.

Production Process 13

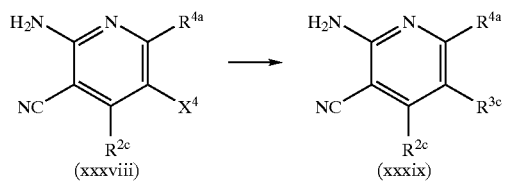

(xxxviii) (xxxix)

In the formula, $R^{2c}$ represents hydrogen atom, hydroxyl group, a $C_{1-6}$ alkoxy group which may have a substituent group, a $C_{1-6}$ alkyl group which may have a substituent group, a $C_{6-14}$ aromatic hydrocarbon cyclic group which may have a substituent group or a 5- to 14-membered aromatic heterocyclic group which may have a substituent group; $R^{3c}$ represents a $C_{6-14}$ aromatic hydrocarbon cyclic group which may have a substituent group or a 5- to 14-membered aromatic heterocyclic group which may have a substituent group; and $R^{4a}$ and $X^4$ have the same meanings as defined above. The compound (xxviii) according to the present invention can be produced by reacting the 2-amino-5-halogenonicotinonitrile derivative (xxxix) with an aryl boron reagent or an aryl tin reagent in the presence of a palladium catalyst and a base in a solvent, to introduce an aromatic group into the 5-position of the pyridine ring in (xxxix). The palladium catalyst used varies depending on the starting material, the solvent used etc., and is not particularly limited so long as it is inert to the reaction. Preferably, dichlorobis(triphenylphoshine) palladium (II), palladium (II) acetate, tetrakis(triphenylphosphine) palladium (0), tris(dibenzylidene acetone) dipalladium (0), dichlorobis(acetonitrile) palladium (II) etc. may be proposed. The base used varies depending on the starting material, the solvent used, etc., and is not particularly limited so long as it is inert to the reaction. Preferably, an inorganic base such as potassium carbonate or calcium phosphate, or an organic amine such as ethyl diisopropyl amine may be proposed. The solvent used varies depending on the starting material, reagents etc., and is not particularly limited insofar as it is inert to the reaction and dissolves the starting material to a certain degree. Preferably, alcohols such as methanol or ethanol, ethers such as tetrahydrofuran, dioxane, dimethoxyethane, diethylene glycol or dimethyl ether, toluene, xylene, N,N-dimethylformamide, 1-methyl pyrrolidinone etc. may be proposed. The reaction temperature is usually room temperature to 150° C.

Production Process 14

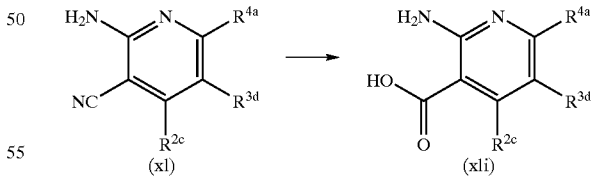

(xl) (xli)

In the formula, $R^{3d}$ represents a $C_{6-14}$ aromatic hydrocarbon cyclic group which may have a substituent group, a 5- to 14-membered aromatic heterocyclic group which may have a substituent group or a 5- to 14-membered non-aromatic heterocyclic group which may have a substituent group; and $R^{2c}$ and $R^{4a}$ have the same meanings as defined above. The compound (xli) according to the present invention can be produced by hydrolyzing the cyano group of the compound (xl) in the presence of a base in a solvent. The base used varies depending on the starting material, the solvent used etc., and is not particularly limited so long as it is inert to the reaction. Preferably, an inorganic base such as sodium hydroxide or potassium hydroxide may be proposed. The solvent used varies depending on the starting material, reagents etc., and is not particularly limited insofar as it is inert to the reacton and dissolves the starting material to a certain degree. Preferably, alcohols such as methanol or ethanol, or a mixture of such alcohols and water. The reaction temperature is usually room temperature to 150° C.

Production Process 15

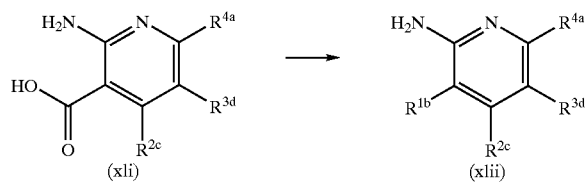

In the formula, $R^{1b}$ represents a carbamoyl group which may have a substituent group; and $R^{2c}$, $R^{3d}$ and $R^{4a}$ have the same meanings as defined above. The carbamoyl derivative (xlii) according to the present invention can be produced by dehydrating condensation of the carboxylic acid derivative (xli) with an amine in the presence of a condensing agent in a solvent. As the condensing agent used, 3-(3-dimethylaminopropyl)-1-ethylcarbodiimide etc. are preferred. The reaction is promoted by adding 1-hydroxybenzotriazole etc. When the amine to be condensed with the carboxylic acid has formed a salt with hydrogen chloride etc., a suitable amount of tertiary amine such as triethylamine is added. As the solvent used, for example, ethers such as tetrahydrofuran, dioxane, dimethoxyethane or diethylene glycol, N,N-dimethylformamide, 1-methyl pyrrolidinone etc. are preferred. The reaction temperature is usually 0 to 50° C., and more preferably around room temperature.

Production Process 16

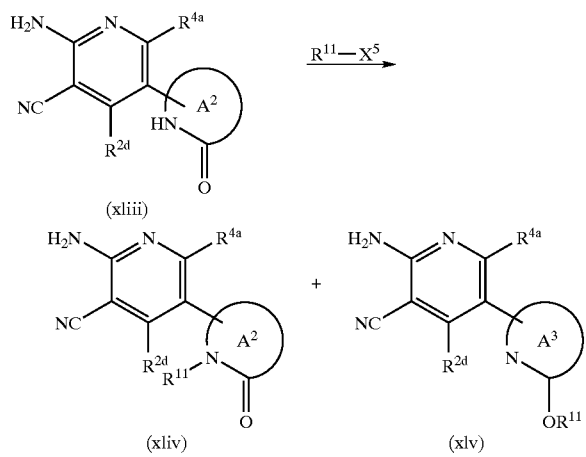

In the formula, $R^{2d}$ represents hydrogen atom, a $C_{1-6}$ alkoxy group which may have a substituent group, a $C_{1-6}$ alkyl group which may have a substituent group, a $C_{6-14}$ aromatic hydrocarbon cyclic group which may have a substituent group or a 5- to 14-membered aromatic heterocyclic group which may have a substituent group; the ring $A^3$ represents pyridinyl group, pyrimidyl group or pyrazinyl group; $R^{11}$ represents a $C_{1-6}$ alkyl group which may have a substituent group, a $C_{2-6}$ alkenyl group which may have a substituent group or a $C_{2-6}$ alkynyl group which may have a substituent group; $X^5$ represents an eliminating group such as a halogen atom or a sulfonate group which may have a substituent group; and $R^{4a}$ and ring $A^2$ have the same meanings as defined above, respectively. The compounds (xliv) and (xlv) according to the present invention can be produced by reacting the compound (xliii) with $R^9$—$X^5$ in the presence of a base in a solvent. The base used varies depending on the starting material, the solvent used etc., and is not particularly limited so long as it is inert to the reaction. Preferably, inorganic bases represented by potassium carbonate, potassium bicarbonate and sodium carbonate may be proposed. The solvent generally used varies depending on the starting material, reagents etc., and is not particularly limited insofar as it it inert to the reacton and dissolves the starting material to a certain degree. Preferably, an amide such as N,N-dimethylformamide may be proposed. The reaction temperature is preferably room temperature to 100° C., and more preferably around 65° C.

Production Process 17

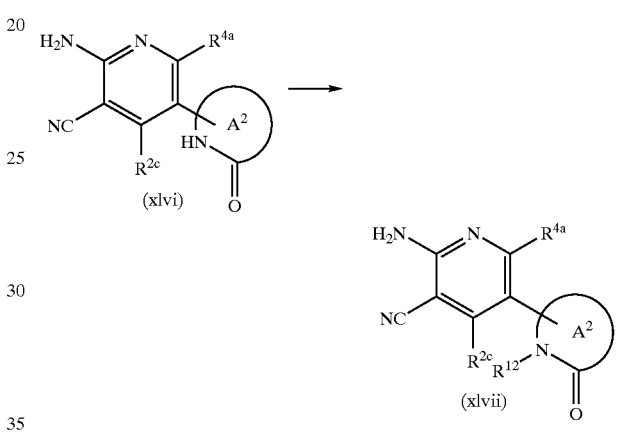

In the formula, $R^{12}$ represents a $C_{6-14}$ aromatic hydrocarbon cyclic group which may have a substituent group or a 5- to 14-membered aromatic heterocyclic group which may have a substituent group; and $R^{2c}$, $R^{4a}$ and ring $A^2$ have the same meanings as defined above, respectively. The compound (xlvii) according to the present invention can be produced by reacting the compound (xlvi) with an aryl boron reagent in the presence of a base and a copper catalyst in a solvent. The base used in the reaction varies depending on the starting material, the solvent used etc., and is not particularly limited insofar as it is inert to the reaction. Preferably, a tertiary amine such as pyridine, diisopropyl ethylamine, triethylamine etc. may be proposed. The copper catalyst used varies depending on the starting material, the solvent used etc., and is not particularly limited insofar as it is inert to the reaction. Preferably, divalent copper such as copper acetate, copper bromide, copper sulfate etc. may be proposed, and copper acetate is more preferred. The solvent used varies depending on the starting material, reagents etc., and is not particularly limited insofar as it is inert to the reaction and dissolves the starting material to a certain degree. Preferably, N,N-dimethylformamide, tetrahydrofuran, ethyl acetate etc. may be proposed. The reaction temperature is preferably around room temperature.

The foregoing is a typical example of the method of producing the compound (I) according to the present invention, and the starting compound in production of the compound of the present invention may form a salt or a hydrate and is not particularly limited so long as it is inert to the reaction. Further, when the compound (I) according to the present invention is obtained in a free form, it can be converted into a salt which may be formed by the above-mentioned compound (I), in a usual manner. Further, the various resulting isomers (for example, geometric isomer, optical isomer based on asymmetric carbon, rotational isomer, stereoisomer and tautomer) of the compound (I) according to the present invention can be purified and isolated by using usual separating means, for example, re-crystallization, diastereomer salt method, enzyme fractionation method, and various kinds of chromatography (for example, thin layer chromatography, column chromatography and gas chromatography).

The compound represented by the above formula (I) according to the present invention, a salt thereof or a hydrate of them can be formed into a pharmaceutical preparation by a conventional method. As the preferable preparation forms, tablets, powders, fine granules, granules, coated tablets, capsules, syrups, troches, inhalations, suppositories, injections, ointments, eye ointments, eye drops, nose drops, ear drops, poultices, lotions etc. may be proposed. In pharmaceutical manufacturing, ordinarily used fillers, binders, disintegrating agents, lubricants, coloring agents, flavoring agents, and as necessary stabilizers, emulsifiers, absorption promoters, surfactants, pH adjusters, preservatives and antioxidants may be used, and it may be prepared in a conventional method by blending ingredients generally used as starting materials for pharmaceutical preparations. As these ingredients, for example, (1) animal and vegetable oils such as soybean oil, tallow or synthetic glyceride; (2) hydrocarbons such as liquid paraffin, squalane or solid paraffin; (3) ester oils such as octyldodecyl myristate or isopropyl myristate; (4) higher alcohols such as cetostearyl alcohol or behenyl alcohol; (5) silicon resin; (6) silicon oil; (7) surfactants such as polyoxyethylene fatty ester, sorbitan fatty ester, glycerin fatty ester, polyoxyethylene sorbitan fatty ester, polyoxyethylene hydrogenated castor oil or polyoxyethylene-polyoxypropylene block copolymer; (8) water-soluble polymers such as hydroethyl cellulose, polyacrylic acid, carboxyvinyl polymer, polyethylene glycol, polyvinylpyrrolidone or methyl cellulose; (9) lower alcohols such as ethanol or isopropanol; (10) polyhydric alcohols such as glycerin, propylene glycol, dipropylene glycol or sorbitol; (11) sugars such as glucose or sucrose; (12) inorganic powder such as silicic anhydride, aluminum magnesium silicate or aluminum silicate; and (13) pure water may be proposed. 1) As the fillers, for example, lactose, corn starch, white sugar, glucose, mannitol, sorbitol, crystalline cellulose, silicon dioxide etc.; 2) as the binders, for example, polyvinyl alcohol, polyvinyl ether, methyl cellulose, ethyl cellulose, arabic gum, tragacanth, gelatin, shellac, hydroxypropyl cellulose, hydroxypropyl methyl cellulose, polyvinylpyrrolidone, polypropylene glycol-polyoxyethylene block polymer, megulumin, calcium citrate, dextrin, pectin etc.; 3) as the disintegrating agents, for example, starch, agar, gelatin powder, crystalline cellulose, calcium carbonate, sodium bicarbonate, calcium citrate, dextrin, pectin, carboxymethyl cellulose calcium etc.; 4) as the lubricants, for example, magnesium stearate, talc, polyethylene glycol, silica, hardened vegetable oil etc.; 5) as the coloring agents, any of which are approved to be added to pharmaceutical preparations; 6) as the flavoring agents, cocoa powder, menthol, aromatic powder, peppermint oil, borneol, cinnamon powder etc.; and 7) as the antioxidants, those which are approved to be added to pharmaceutical preparations, such as ascorbic acid, α-tocopherol etc., maybe used, respectively.

1) The oral preparation is produced by mixing the compound according to the present invention or a salt thereof with fillers and if necessary with a binder, a disintegrating agent, a lubricant, a coloring agent, a flavoring agent etc., and then forming it in a usual manner into powders, fine granules, granules, tablets, coated tablets, capsules, etc. 2) The tablets and granules may be coated with a sugar or gelatin coating or if necessary with another suitable coating. 3) The liquid preparations such as syrups, injections and eye drops are prepared by mixing the active agent with a pH adjuster, a solubilizer and an isotonizing agent etc., and with a solubilizing aid, a stabilizer, a buffer, a suspension agent, an antioxidant etc. if necessary, followed by forming it into a preparation in a usual manner. The liquid preparation may be formed into a freeze-dried product and the injection can be administered intravenously, subcutaneously or intramuscularly. Preferable examples of the suspension agent include methyl cellulose, Polysorbate 80, hydroxyethyl cellulose, arabic gum, tragacanth powder, sodium carboxymethyl cellulose, polyoxyethylene sorbitan monolaurate etc.; preferable examples of the solubilizing aid include polyoxyethylene hardened castor oil, Polysorbate 80, nicotinamide, polyoxyethylene sorbitan monolaurate etc.; preferable examples of the stabilizer include sodium sulfite, sodium metasulfite, ether etc.; preferable examples of the preservative include methyl p-oxybenzoate, ethyl p-oxybenzoate, sorbic acid, phenol, cresol, chlorocresol etc. 4) The agent for external application can be produced in any conventional method. That is, the starting base material can make use of various starting materials ordinarily used in pharmaceutical preparations, quasi-drug, cosmetics, etc. For example, the material includes animal and vegetable oils, mineral oil, ester oil, waxes, higher alcohols, fatty acids, silicon oil, surfactants, phospholipids, alcohols, polyvalent alcohols, water-soluble polymers, clay minerals, pure water etc. If necessary, a pH adjuster, an antioxidant, a chelating agent, a preservative, a coloring agent, a perfume etc. can further be added. Further, ingredients having a differentiation-inducing action, a blood-stream promoting agent, a sterilizer, an antiinflammatory agent, a cell activator, vitamins, amino acids, a humectant, a keratin solubilizer etc. can also be incorporated as necessity.

Although the dose of the medicament according to the present invention varies depending on severeness of symptoms, age, sex, body weight, administration form, type of salt, chemical sensitivity, type of disease etc., it is given daily in one portion or in divided portions to an adult in a dose of usually about 30 µg to 10 g, preferably 100 µg to 5 g, more preferably 100 µg to 100 mg for oral administration, or about 30 µg to 1 g, preferably 100 µg to 500 mg, more preferably 100 µg to 30 mg for injection.

According to the present invention, a novel 2-aminopyridine compound could be provided. The compounds according to the present invention or a salt thereof have an excellent antagonistic action on an adenosine receptor (adenosine $A_1$, $A_{2a}$, $A_{2b}$ or $A_3$ receptor), and are excellent as an antagonist for an adenosine $A_2$ receptor, particularly for an adenosine $A_{2B}$ receptor. The compounds according to the present invention or a salt thereof are useful as an agent for treating or preventing a disease to which an adenosine receptor (adenosine $A_1$, $A_{2a}$, $A_{2b}$ or $A_3$ receptor) relates, and a disease against which an antagonist for the receptor is efficacious. The compound according to the present invention or a salt thereof is useful not only as an agent for treating, preventing or improving constipation, irritable bowel syndrome, constipation accompanying irritable bowel syndrome, organic constipation, constipation accompanying enteroparalytic ileus, constipation accompanying congenital digestive tract dysfunction, constipation accompanying ileus, diabetes, diabetic complications, diabetic retinopathy, obesity, asthma etc., but also useful as a hypoglycemic agent, an improving agent for impaired glucose tolerance, a potentiating agent for insulin sensitivity, hypotensive agent, a diuretic, a therapeutic agent for osteoporosis, an anti-Parkinson's disease agent, an anti-Alzheimer's disease agent, a therapeutic agent for inflammatory intestinal diseases, a therapeutic agent for Crohn's disease, etc.

EXAMPLES

Reference Examples, Examples and Test Examples shown below are described merely for illustrative purposes, and the compounds of the invention are not limited to the following specific examples in any case. The present invention can be carried out to the maximum by those skilled in the art by making various modifications not only to the following examples but also to the claims in the present specification, and such modifications fall under the claims of the present application.

Reference Example 1
1-(2-Furyl)-2-(4-pyridyl)-1-ethanone

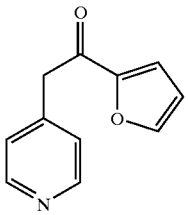

In a nitrogen atmosphere, lithium bis (trimethylsilyl) amide (100 mL, 100 mmol) was added dropwise into a solution of 4-picoline (4.6 g, 49.4 mmol) and ethyl 2-furancarboxylate (7.7 g, 54.9 mmol) in tetrahydrofuran (40 mL) at 0° C. over 1 hour, followed by stirring as it was for 2 hours. Hexane (140 mL) was added to the reaction solution, and the resulting crystals were collected by filtration. The resulting crystals were dissolved in ethyl acetate and an aqueous saturated solution of ammonium chloride. The organic layer was washed with an aqueous saturated solution of ammonium chloride (×2) and brine, dried over anhydrous sodium sulfate, and concentrated. Hexane was added to the residue, and the resulting precipitates were collected by filtration and washed with hexane, to give the title compound (6.5 g, 70%) as a pale yellow solid.

$^1$H NMR (400 MHz, DMSO-$d_6$) δ ppm; 4.26 (2H, s), 6.77 (1H, dd, J=2.0, 3.6 Hz), 7.31 (2H, dd, J=1.6, 4.4 Hz), 7.65 (1H, dd, J=0.8, 3.6 Hz), 8.05 (1H, dd, J=0.8, 2.0 Hz), 8.51 (2H, dd, J=1.6, 4.4 Hz).

Reference Example 2
3-(Dimethylamino)-1-(2-furyl)-2-(4-pyridyl)-2-propen-1-one

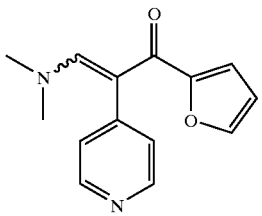

N,N-Dimethylformamide dimethylacetal (5 mL) was added to 1-(2-furyl)-2-(4-pyridyl)-1-ethanone (2.0 g, 10.7 mmol), followed by stirring at 100° C. for 2 hours. After cooling as it was, the reaction solution was diluted with ethyl acetate and an aqueous saturated solution of ammonium chloride. The aqueous layer was extracted with ethyl acetate (×6). The combined organic layer was dried over anhydrous sodium sulfate and concentrated, to give the title compound (2.5 g, 97%) as a reddish brown oil.

$^1$H NMR (400 MHz, DMSO-$d_6$) δ ppm; 2.80 (6H, br s), 6.53 (1H, br), 6.60 (1H, br), 7.10 (2H, d, J=4.0 Hz), 7.65 (1H, br), 7.75 (1H, s), 8.44 (2H, d, J=4.0 Hz).

Reference Example 3
6-(2-Furyl)-2-oxo-5-(4-pyridyl)-1,2-dihydro-3-pyridinecarbonitrile

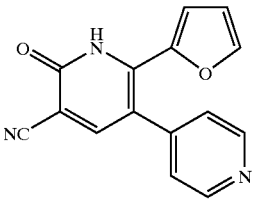

Sodium methoxide (1.20 g, 22.2 mmol) was added to a solution of 3-(dimethylamino)-1-(2-furyl)-2-(4-pyridyl)-2-propen-1-one (2.27 g, 9.37 mmol) and 2-cyanoacetamide (950 mg, 11.3 mmol) in N,N-dimethylformamide, followed by stirring at 80° C. for 2 hours in a nitrogen atmosphere. After cooling as it was, the reaction solution was concentrated and diluted with water. After neutralized with 6 N hydrochloric acid, the resulting solid was collected by filtration and washed with water, to give the title compound (1.78 g, 72%) as a pale brown solid.

$^1$H NMR (400 MHz, DMSO-$d_6$) δ ppm; 6.64 (1H, dd, J=1.6, 4.0 Hz), 6.92 (1H, d, J=4.0 Hz), 7.24 (2H, dd, J=1.6, 4.4 Hz), 7.75 (1H, dd, J=0.8, 1.6 Hz), 8.21 (1H, s), 8.57 (2H, dd, J=1.6, 4.4 Hz).

Reference Example 4
2-Chloro-6-(2-furyl)-5-(4-pyridyl)-3-pyridinecarbonitrile

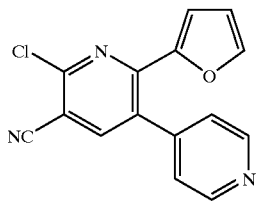

A suspension of 6-(2-furyl)-2-oxo-5-(4-pyridyl)-1,2-dihydro-3-pyridinecarbonitrile (21.0 g, 79.8 mmol) in phosphorus oxychloride (90 g) was stirred in a nitrogen atmosphere at 110° C. After 4 hours, additional phosphorus oxychloride (50 g) was added thereto, followed by heating under stirring for further 5 hours. After cooling as it was, the reaction solution was concentrated. After ice was added to the residue, it was neutralized with saturated sodium bicarbonate. After extracting with ethyl acetate (2 1)-tetrahydrofuran (1 1), the organic layer was washed with brine, dried over anhydrous magnesium sulfate and concentrated. After adding diethyl ether to the residue, the resulting solid was collected by filtration and washed with diethyl ether, to give the title compound (13.6 g, 61%) as a dark yellow solid.

$^1$H NMR (400 MHz, DMSO-$d_6$) δ ppm; 6.62 (1H, dd, J=1.6, 3.6 Hz), 6.78 (1H, dd, J=0.8, 3.6 Hz), 7.42 (2H, dd, J=1.6, 4.4 Hz), 7.76 (1H, dd, J=0.8, 1.6 Hz), 8.48 (1H, s), 8.69 (2H, dd, J=1.6, 4.4 Hz).

Reference Example 5
3-(Dimethylamino)-1-(2-furyl)-2-propen-1-one

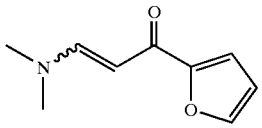

A mixture of 2-acetylfuran (25.0 g, 0.227 mmol) and N,N-dimethylformamide dimethylacetal (40 ml) was stirred at 100° C. for 9 hours. After cooling as it was, the reaction solution was concentrated. Diethyl ether and hexane were added to the residue, and the resulting solid was collected by filtration and washed with hexane, to give the title compound (36.5 g, 97%) as a brown solid.

$^1$H NMR (400 MHz, DMSO-d$_6$) δ ppm; 2.88 (3H, br s), 3.14 (3H, br s), 5.65 (1H, d, J=12.6 Hz), 6.60 (1H, dd, J=2.0, 3.4 Hz), 7.10 (1H, dd, J=0.8, 3.4 Hz), 7.68 (1H, d, J=12.6 Hz), 7.79 (1H, dd, J=0.8, 2.0 Hz).

Reference Example 6
6-(2-Furyl)-2-oxo-1,2-dihydro-3-pyridinecarbonitrile

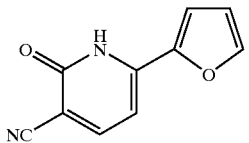

A suspension of 3-(dimethylamino)-1-(2-furyl)-2-propen-1-one (15.0 g, 90.9 mmol), 2-cyanoacetamide (8.5 g, 101 mmol) and potassium carbonate (38.0 g, 275 mmol) in dimethyl sulfoxide (80 ml) was stirred at 120 to 140° C. for 21 hours. After cooling as it was, the reaction mixture was diluted with water. After adjusting to pH 3 with conc. hydrochloric acid, the resulting solid was collected by filtration and washed with water, to give the title compound (13.0 g, 77%) as a brown solid.

$^1$H NMR (400 MHz, DMSO-d$_6$) δ ppm; 6.75 (1H, d, J=8.0 Hz), 6.78 (1H, dd, J=1.6, 3.6 Hz), 7.61 (1H, d, J=3.6 Hz), 8.02 (1H, d, J=1.6 Hz), 8.15 (1H, d, J=8.0 Hz).

Reference Example 7
2-[[3-Cyano-6-(2-furyl)-2-pyridyl]oxy]acetamide

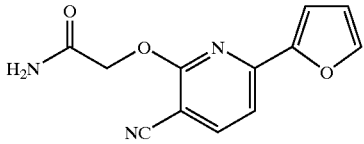

A suspension of 6-(2-furyl)-2-oxo-1,2-dihydro-3-pyridinecarbonitrile (6.0 g, 32.3 mmol), 2-chloroacetamide (3.0 g, 37.7 mmol), sodium iodide (5.7 g, 38.0 mmol) and potassium carbonate (9.0 g, 56.2 mmol) in acetone (100 ml) was stirred at 60° C. for 6 hours. After cooling as it was, the reaction solution was diluted with ethyl acetate and water. The organic layer was washed with an aqueous saturated solution of sodium bicarbonate (×2) and an aqueous saturated solution of ammonium chloride, dried over anhydrous sodium sulfate, and concentrated. Diethyl ether was added to the residue, and the resulting precipitates were collected by filtration and washed with diethyl ether, to give the title compound (4.2 g, 54%) as a brown solid.

$^1$H NMR (400 MHz, DMSO-d$_6$) δ ppm; 4.87 (2H, s), 6.75 (1H, dd, J=2.0, 3.4 Hz), 7.26 (1H, br), 7.26 (1H, dd, J=0.8, 3.4 Hz), 7.45 (1H, d, J=8.0 Hz), 7.61 (1H, br), 7.96 (1H, dd, J=0.8, 2.0 Hz), 8.29 (1H, d, J=8.0 Hz).

Reference Example 8
2-Amino-6-(2-furyl)nicotinonitrile

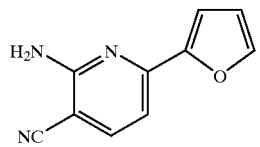

A suspension of 2-[[3-cyano-6-(2-furyl)-2-pyridyl]oxy]acetamide (8.0 g, 32.9 mmol) and potassium carbonate (9.1 g, 65.9 mmol) in N,N-dimethylformamide (80 ml) was stirred at 120° C. for 1.5 hours. After cooling as it was, the reaction solution was diluted with water and ethyl acetate, and the insoluble matters were filtered off. The aqueous layer in the filtrate was extracted with ethyl acetate. The combined organic layer was washed with an aqueous saturated solution of ammonium chloride (×2), dried over anhydrous sodium sulfate, and concentrated. The residue was suspended in methanol, and the resulting solid was collected by filtration and washed with methanol, to give the title compound (3.81 g, 63%) as a brown solid.

$^1$H NMR (400 MHz, DMSO-d$_6$) δ ppm; 6.68 (1H, dd, J=1.6, 3.6 Hz), 6.96 (2H, br s), 7.02 (1H, d, J=8.2 Hz), 7.13 (1H, dd, J=0.8, 3.6 Hz), 7.89 (1H, dd, J=0.8, 1.6 Hz), 7.91 (1H, d, J=8.2 Hz).

Reference Example 9
2-Amino-5-bromo-6-(2-furyl)nicotinonitrile

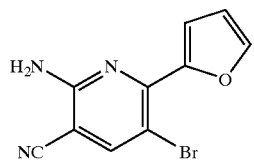

N-Bromosuccinimide (3.5 g, 19.7 mmol) was added to a solution (60 ml) of 2-amino-6-(2-furyl)nicotinonitrile (4.0 g, 21.6 mmol) in N,N-dimethylformamide in a nitrogen atmosphere at 1 to 2° C., followed by stirring as it was. After 30 minutes, the reaction solution was diluted with ethyl acetate and an aqueous saturated solution of potassium carbonate. The organic layer was washed with an aqueous saturated solution of potassium carbonate and an aqueous saturated solution of ammonium chloride, then dried over anhydrous sodium sulfate and concentrated. Methanol was added to the residue, and the resulting solid was collected by filtration and washed with methanol, to give the title compound (3.02 g, 53%) as a brown solid.

$^1$H NMR (400 MHz, DMSO-d$_6$) δ ppm; 6.72 (1H, dd, J=1.8, 3.6 Hz), 7.19 (2H, br s), 7.44 (1H, dd, J=0.8, 3.6 Hz), 7.96 (1H, dd, J=0.8, 1.8 Hz), 8.26 (1H, s)

Reference Example 10
5-Bromo-2-methoxypyridine

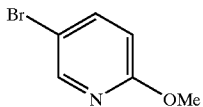

After sodium (10 g, 0.435 mol) was dissolved in methanol (500 ml), 2,5-dibromopyridine (50 g, 0.211 mol) was added thereto and the mixture was heated for 2 days under reflux. The reaction solution was cooled as it was, and then concentrated. Then, the residue was diluted with ethyl acetate and an aqueous saturated solution of ammonium chloride. The organic layer was washed with an aqueous saturated solution of ammonium chloride and brine, and then dried over anhydrous sodium sulfate and concentrated, to give the title compound (33 g, 83%) as a pale brown oil.

$^1$H NMR (400 MHz, DMSO-d$_6$) δ ppm; 3.84 (3H, s), 6.72 (1H, dd, J=0.8, 8.8 Hz), 7.89 (1H, dd, J=2.4, 8.8 Hz), 8.29 (1H, dd, J=0.8, 2.4 Hz).

Reference Example 11
2-Methoxy-5-(1,1,1-tributylstannyl)pyridine

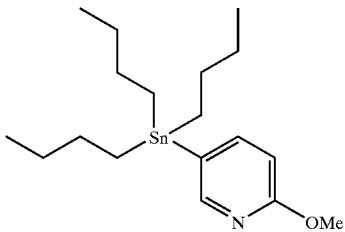

2.5 M n-butyl lithium solution in hexane (12.0 ml, 30.0 mmol) was added dropwise to a solution of 5-bromo-2-methoxypyridine (5.0 g, 26.6 mmol) in tetrahydrofuran (100 ml) over 30 minutes at −70° C. in a nitrogen atmosphere. Then, a solution of tributyltin chloride (10.4 ml, 32.0 mmol) in tetrahydrofuran (20 ml) was added dropwise thereinto over 1 hour. Then, the reaction solution was heated to room temperature and stirred as it was. After 30 minutes, the reaction solution was diluted with an aqueous saturated solution of ammonium chloride and ethyl acetate. The organic layer was washed with an aqueous saturated solution of ammonium chloride and brine, dried over anhydrous sodium sulfate and concentrated. The residue was subjected to silica gel column chromatography (elution solvent; hexane, hexane:ethyl acetate=40:1), to give the title compound (7.9 g, 75%) as a colorless oil.

$^1$H NMR (400 MHz, DMSO-d$_6$) δ ppm; 0.82–0.90 (9H, m), 1.02–1.08 (6H, m), 1.22–1.35 (6H, m), 1.46–1.54 (6H, m), 3.82 (3H, s), 6.80 (1H, dd, J=0.8, 8.0 Hz), 7.69 (1H, dd, J=1.6, 8.0 Hz), 8.10 (1H, dd, J=0.8, 1.6 Hz).

Reference Example 12
(E)-1,3-Di(3-fluorophenyl)-2-propen-1-one

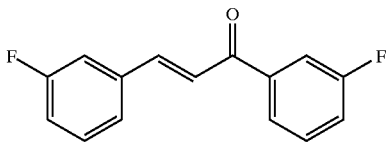

A mixture of 3-fluorobenzaldehyde (7.63 mL, 72.4 mmol), 3-fluoroacetophenone (10 g, 72.4 mmol), potassium hydroxide (5.18 g, 92.6 mmol), ethanol (23 mL) and water (47 mL) was stirred overnight at room temperature. After the reaction solution was diluted with water, the solid was collected by filtration and washed with ethanol and diethyl ether, to give the title compound (16.4 g, 93%).

$^1$H NMR (400 MHz, DMSO-d$_6$) δ ppm; 7.10–7.16 (1H, m), 7.27–7.37 (2H, m), 7.39–7.42 (2H, m), 7.46 (1H, d, J=15 Hz), 7.50 (1H, dd, J=5.4, 7.7 Hz), 7.68–7.73 (1H, m), 7.77 (1H, d, J=15 Hz), 7.78–7.82 (1H, m).

Reference Example 13
4,6-Di(3-fluorophenyl)-2-oxo-1,2-dihydro-3-pyridinecarbonitrile

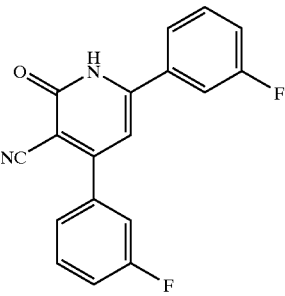

(E)-1,3-Di(3-fluorophenyl)-2-propen-1-one (16.4 g, 67.2 mmol), 2-cyanoacetamide (6.21 g, 73.9 mmol), and a solution of potassium t-butoxide (30.2 g, 269 mmol) in dimethyl sulfoxide (131 mL) were stirred overnight at room temperature in an oxygen atmosphere. Water (300 mL) and 6 N hydrochloric acid (390 mL) were added to the reaction solution. The solid was collected by filtration and washed with water, to give the title compound (17.4 g, 84%).

$^1$H NMR (400 MHz, DMSO-d$_6$) δ ppm; 6.81 (1H, s), 7.28–7.36 (1H, m), 7.50–7.58 (1H, m), 7.68–7.88 (2H, m).

Reference Example 14
Isopropyl 3-(2-furyl)-3-oxopropanethioate

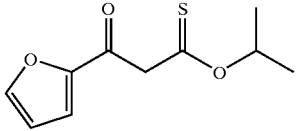

A mixture of isopropyl (methylsulfanyl)methanethioate (7.0 g, 46.7 mmol), 2-acetyl furan (5.14 g, 46.7 mmol), potassium t-butoxide (10.5 g, 93.5 mmol) and t-butanol (35 mL) was stirred overnight at room temperature. Ice was added to the reaction solution, followed by acidifying with 5 N hydrochloric acid. The solid was collected by filtration and washed with water, to give the title compound (3.7 g, 37%).

$^1$H NMR (400 MHz, DMSO-d$_6$) δ ppm; 1.38 (6H, d, J=8.8 Hz), 5.58–5.69 (1H, m), 6.27 (1H, s), 6.53 (1H, dd, J=2.0, 3.3 Hz), 7.05 (1H, dd, J=0.4, 3.3 Hz), 7.52 (1H, dd, J=0.4, 2.0 Hz).

Reference Example 15
(Z)-1-(2-Furyl)-3-isopropoxy-3-(methylsulfanyl)-2-propen-1-one

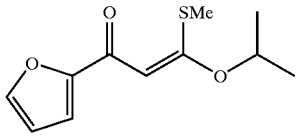

A mixture of isopropyl 3-(2-furyl)-3-oxopropanethioate (3.7 g, 17.5 mmol), potassium carbonate (7.3 g, 52.4 mmol) and acetone (15 mL) was heated under reflux for 1 hour. After cooling the mixture to 0° C., methyl iodide (2.17 mL, 34.9 mmol) was added thereto, followed by stirring at room temperature for 2 hours. After diluting the reaction solution with ethyl acetate, the insoluble matters were filtered off. The filtrate was concentrated, and then the residue was purified by silica gel column chromatography (elution solvent; ethyl acetate/hexane=1:1), to give the title compound (3.2 g, 81%).
$^1$H NMR (400 MHz, DMSO-d$_6$) δ ppm; 1.42 (6H, d, J=6.0 Hz), 2.28 (3H, s), 4.72–4.82 (1H, m), 6.35 (1H, s), 6.49 (1H, dd, J=1.5, 3.6 Hz), 7.10 (1H, dd, J=1.0, 3.6 Hz), 7.47 (1H, dd, J=1.0, 1.5 Hz).

Reference Example 16
6-(2-Furyl)-4-isopropoxy-2-oxo-1,2-dihydro-3-pyridinecarbonitrile

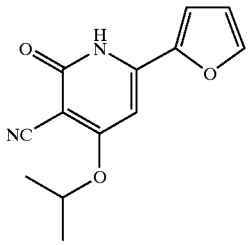

Sodium (309 mg, 13.4 mmol) was dissolved in isopropanol (46 mL). Then, (Z)-1-(2-furyl)-3-isopropoxy-3-(methylsulfanyl)-2-propen-1-one (3.03 g, 13.4 mmol) and 2-cyanoacetamide (1.13 g, 13.4 mmol) were added thereto, followed by stirring overnight at room temperature. Ice-water was added to the reaction solution, and then the solid was collected by filtration, and washed with water and diethyl ether, to give the title compound (2.3 g, 70%).
$^1$H NMR (400 MHz, DMSO-d$_6$) δ ppm; 1.35 (6H, d, J=6.0 Hz), 4.98–5.08 (1H, m), 6.60–6.66 (1H, m), 6.77–6.81 (1H, m), 7.60–7.67 (1H, m), 8.00–8.05 (1H, m).

Example 1
2-Amino-6-(2-furyl)-5-(4-pyridyl)-3-pyridinecarbonitrile

A solution of ammonia in ethanol, 30 ml, (ethanol saturated at 0° C. with an ammonia gas) was added to 2-chloro-6-(2-furyl)-5-(4-pyridyl)-3-pyridinecarbonitrile (200 mg, 0.710 mmol). Then, it was sealed in a stainless steel autoclave, and heated under stirring at 100° C. After 24 hours, the reaction solution was cooled as it was and concentrated. The residue was subjected to silica gel column chromatography (elution solvent; hexane, hexane:ethyl acetate=2:1, 1:1, 1:2), and then suspended in diethyl ether. The resulting precipitates were collected by filtration and washed with diethyl ether, to give the title compound (50 mg, 27%) as a pale orange solid.
$^1$H NMR (400 MHz, DMSO-d$_6$) δ ppm; 6.54 (1H, dd, J=1.6, 3.6 Hz), 6.57 (1H, dd, J=0.8, 3.6 Hz), 7.20 (2H, br s), 7.24 (2H, dd, J=1.6, 4.4 Hz), 7.64 (1H, dd, J=0.8, 1.6 Hz), 7.92 (1H, s), 8.55 (2H, dd, J=1.6, 4.4 Hz);
MS m/e (ESI) 263 (MH$^+$).

Example 2
2-Amino-6-(fluorophenyl)-5-(4-pyridyl)-3-pyridinecarbonitrile

The title compound was synthesized in the same manner as in Examples 18 to 20 described below or by its analogous method.
$^1$H NMR (400 MHz, DMSO-d$_6$) δ ppm; 6.99–7.03 (1H, m), 7.09–7.14 (3H, m), 7.16–722 (1H, m), 7.28–7.35 (3H, m), 8.09 (1H, s), 8.43 (2H, dd, J=1.6, 4.4 Hz);
MS m/e (ESI) 291 (MH$^+$).

Example 3
2-Amino-6-(2-furyl)-5-(4-methoxy-3-pyridyl)-3-pyridinecarbonitrile A solution of 2-amino-5-bromo-6-(2-furyl)nicotinonitrile (1.80 g, 6.82 mmol), 2-methoxy-5-(1,1,1-tributylstannyl)pyridine (5.20 g, 13.1 mmol) and dichlorobis(triphenylphosphine) palladium (II) (480 mg, 0.634 mmol) in N,N-dimethylformamide (18 ml) was stirred at 80° C. for 2 hours in a nitrogen atmosphere. After cooling as it was, the reaction solution was diluted with ethyl acetate and an aqueous saturated solution of ammonium chloride. The organic layer was washed with an aqueous saturated solution of ammonium chloride (×2), then dried over anhydrous sodium sulfate and concentrated. The residue was subjected to silica gel column chromatography (elution solvent; hexane, hexane:ethyl acetate=8:1, 4:1), and then suspended in diethyl ether. The resulting solid was collected by filtration and washed with diethyl ether, to give the title compound (1.12 g, 56%) as a yellow solid.
$^1$H NMR (400 MHz, DMSO-d$_6$) δ ppm; 3.88 (3H, s), 6.38 (1H, dd, J=0.8, 3.6 Hz), 6.51 (1H, dd, J=1.6, 3.6 Hz), 6.83 (1H, d, J=4.6 Hz), 7.08 (2H, br s), 7.54 (1H, dd, J=2.4, 4.6 Hz), 7.67 (1H, dd, J=0.8, 1.6 Hz), 7.84 (1H, s), 8.04 (1H, d, J=2.4 Hz).

Example 4
2-Amino-6-(2-furyl)-5-(6-oxo-1,6-dihydro-3-pyridinyl)nicotinonitrile A solution of 2-amino-6-(2-furyl)-5-(4-methoxy-3-pyridyl)-3-pyridinecarbonitrile (1.0 g, 3.42 mmol) in acetic acid (6 ml)-conc. hydrobromic acid (10 ml) was stirred at 100° C. for 1.5 hours. After cooling as it was, the reaction solution was adjusted to pH 12 to 13 with 5 N sodium hydroxide and washed with ethyl acetate. The organic layer was extracted with 1 N sodium hydroxide (×2), and then the combined aqueous layer was neutralized with 5 N hydrochloric acid. The resulting solid was collected by filtration, to give the title compound (760 mg) as yellow crude crystals. After suspending the product in methanol, 4 N HCl/ethyl acetate was added thereto to dissolved and it subjected to silica gel column chromatography (elution solvent; dichloromethane, dichloromethane:methanol=40:1, 20:1, 10:1). The resulting crude objective compound was suspended in water, and then neutralized with 5 N sodium hydroxide. The solid was collected by filtration and washed with water, to give the title compound (486 mg, 51%) as a yellow solid.
$^1$H NMR (400 MHz, DMSO-d$_6$) δ ppm; 6.30 (1H, d, J=9.6 Hz), 6.57 (1H, dd, J=1.8, 3.4 Hz), 6.59 (1H, dd, J=0.6, 3.4 Hz), 7.02 (2H, br s), 7.20 (1H, dd, J=2.8, 9.6 Hz), 7.33 (1H, d, J=2.8 Hz), 7.75 (1H, dd, J=0.6, 1.8 Hz), 7.82 (1H, s);
MS m/e (ESI) 279 (MH$^+$).

Example 5
2-Amino-5-(1-ethyl-6-oxo-1,6-dihydro-3-pyridinyl)-6-(2-furyl)nicotinonitrile Sodium methoxide (155 mg, 2.87 mmol) was added to a suspension of 2-amino-6-(2-furyl)-5-(6-oxo-1,6-dihydro-3-pyridinyl)nicotinonitrile (400 mg, 1.44 mmol) in methanol (8 ml) at room temperature in a nitrogen atmosphere, followed by stirring. After 15 minutes, iodoethane (0.35 ml, 4.38 mmol) was added thereto, followed by stirring as it was. After 15 hours, additional iodoethane (0.35 ml, 4.38 mmol) was added thereto, and the mixture was further stirred. After 24 hours, the reaction solution was concentrated. The residue was subjected to silica gel column chromatography (elution solvent; hexane, hexane:ethyl acetate=2:1, 1:2, 1:5). The resulting crude objective compound was suspended in diethyl ether, and then the solid was collected by filtration and washed with diethyl ether, to give the title compound (149 mg, 34%) as a pale yellow solid.

$^1$H NMR (400 MHz, DMSO-d$_6$) δ ppm; 1.23 (3H, t, J=7.2 Hz), 3.91 (2H, q, J=7.2 Hz), 6.34 (1H, d, J=9.2 Hz), 6.57 (1H, dd, J=2.0, 3.2 Hz), 6.62 (1H, dd, J=0.8, 3.2 Hz), 7.06 (2H, br s), 7.19 (1H, dd, J=2.8, 9.2 Hz), 7.71 (1H, d, J=2.8 Hz), 7.75 (1H, dd, J=0.8, 2.0 Hz), 7.88 (1H, s);

MS m/e (ESI) 307 (MH$^+$).

Example 6
2-Amino-6-(2-furyl)-5-(1-methyl-6-oxo-1,6-dihydro-3-pyridinyl)nicotinonitrile The title compound was synthesized in the same manner as in Example 30.

$^1$H NMR (400 MHz, DMSO-d$_6$) δ ppm; 3.45 (3H, s), 6.35 (1H, d, J=9.2 Hz), 6.57 (1H, dd, J=1.6, 3.6 Hz), 6.65 (1H, dd, J=0.8, 3.6 Hz), 7.06 (2H, br s), 7.17 (1H, dd, J=2.8, 9.2 Hz), 7.75 (1H, d, J=2.8 Hz), 7.76 (1H, dd, J=0.8, 1.6 Hz), 7.84 (1H, s);

MS m/e (ESI) 293 (MH$^+$).

Example 7
2-Amino-6-(3-fluorophenyl)-5-(6-oxo-1,6-dihydro-3-pyridinyl)nicotinonitrile The title compound was synthesized in the same manner as in Examples 21 to 29.

$^1$H NMR (400 MHz, DMSO-d$_6$) δ ppm; 6.19 (1H, d, J=9.6 Hz), 6.86 (2H, br s), 7.00 (1H, dd, J=2.8, 9.6 Hz), 7.17–7.28 (4H, m), 7.37–7.45 (1H, m), 8.26 (1H, s)

MS m/e (ESI) 307 (MH$^+$).

Example 8
2-Amino-6-(3-fluorophenyl)-5-(1-methyl-6-oxo-1,6-dihydro-3-pyridinyl)nicotinonitrile Using 2-amino-6-(3-fluorophenyl)-5-(6-oxo-1,6-dihydro-3-pyridinyl)nicotinonitrile, the title compound was synthesized in the same manner as in Example 30.

$^1$H NMR (400 MHz, DMSO-d$_6$) δ ppm; 3.40 (3H, s), 6.17 (1H, d, J=9.6 Hz), 6.85 (1H, dd, J=2.4, 9.6 Hz), 7.12 (2H, br s), 7.14–7.26 (3H, m), 7.34–7.42 (1H, m), 7.74 (1H, d, J=2.4 Hz), 7.98 (1H, s);

MS m/e (ESI) 321 (MH$^+$).

Example 9
2-Amino-5-(4-cyanophenyl)-6-(2-furyl)nicotinonitrile

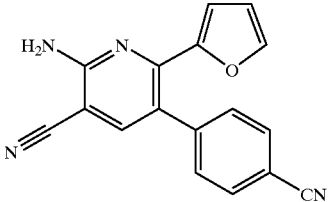

2-Amino-5-bromo-6-(2-furyl)nicotinonitrile (20 mg, 75.7 μmol), 4-cyanophenylboric acid (30 mg, 204 μmol), dichlorobis(acetonitrile) palladium (II) (2 mg, 7.71 μmol), and a solution of 2 M aqueous potassium carbonate (150 μL, 300 μmol) in N,N-dimethylformamide (0.6 mL) was stirred at 80° C. for 14 hours. After cooling as it was, the reaction solution was diluted with ethyl acetate and water. After filtering off the insoluble matters, the organic layer in the filtrate was concentrated. A half of the residue was purified by HPLC on a reverse phase column and using a water-acetonitrile-trifluoroacetic acid system as the elution solvent, to give the title compound (3.33 mg).

MS m/e (ESI) 401 (MH$^+$).

The title compounds of the following Examples 10 to 76 were synthesized in the same manner as in Example 3 or 9, or by its analogous method.

Example 10
2-Amino-5,6-di(2-furyl)nicotinonitrile

Example 11
2-Amino-5-(4-cyanophenyl)-6-(2-furyl)nicotinonitrile

Example 12
2-Amino-6-(2-furyl)-5-phenylnicotinonitrile

Example 13
2-Amino-6-(2-furyl)-5-(4-methylphenyl)nicotinonitrile

Example 14
2-Amino-6-(2-furyl)-5-(3-methylphenyl)nicotinonitrile

Example 15
2-Amino-6-(2-furyl)-5-(2-methylphenyl)nicotinonitrile

Example 16
2-Amino-6-(2-furyl)-5-(4-methoxyphenyl)nicotinonitrile

Example 17
2-Amino-6-(2-furyl)-5-(3-methoxyphenyl)nicotinonitrile

Example 18
2-Amino-5-(2,4-dimethoxyphenyl)-6-(2-furyl)nicotinonitrile

Example 19
2-Amino-5-(3,4-dimethoxyphenyl)-6-(2-furyl)nicotinonitrile

Example 20
2-Amino-6-(2-furyl)-5-(3,4,5-trimethoxyphenyl)nicotinonitrile

Example 21
2-Amino-5-(1,3-benzodioxol-5-yl)-6-(2-furyl)nicotinonitrile

Example 22
2-Amino-5-[4-(benzyloxy)phenyl]-6-(2-furyl)nicotinonitrile

Example 23
2-Amino-5-[3-(benzyloxy)phenyl]-6-(2-furyl)nicotinonitrile

Example 24
2-Amino-6-(2-furyl)-5-(4-phenoxyphenyl)nicotinonitrile

Example 25
2-Amino-5-(3-ethoxyphenyl)-6-(2-furyl)nicotinonitrile

Example 26
2-Amino-6-(2-furyl)-5-[4-(trifluoromethoxy)phenyl]nicotinonitrile

Example 27
2-Amino-6-(2-furyl)-5-[3-(trifluoromethoxy)phenyl)nicotinonitrile]

Example 28
2-Amino-5-(4-dimethylaminophenyl)-6-(2-furyl)nicotinonitrile

Example 29
2-Amino-6-(2-furyl)-5-[4-(methylsulfanyl)phenyl]nicotinonitrile

Example 30
2-Amino-5-(4-fluorophenyl)-6-(2-furyl)nicotinonitrile

Example 31
2-Amino-5-(3-fluorophenyl)-6-(2-furyl)nicotinonitrile

Example 32
2-Amino-5-(2-fluorophenyl)-6-(2-furyl)nicotinonitrile

Example 33
2-Amino-5-(2,4-difluorophenyl)-6-(2-furyl)nicotinonitrile

Example 34
2-Amino-6-(2-furyl)-5-(2,3,4,5,6-pentafluorophenyl)nicotinonitrile

Example 35
2-Amino-6-(2-furyl)-5-[4-(trifluoromethyl)phenyl]nicotinonitrile

Example 36
2-Amino-6-(2-furyl)-5-[3-(trifluoromethyl)phenyl]nicotinonitrile

Example 37
2-Amino-6-(2-furyl)-5-[2-(trifluoromethyl)phenyl]nicotinonitrile

Example 38
2-Amino-5-[3,5-di(trifluoromethyl)phenyl]-6-(2-furyl)nicotinonitrile

Example 39
2-Amino-6-(2-furyl)-5-(4-nitrophenyl)nicotinonitrile

Example 40
2-Amino-6-(2-furyl)-5-(3-nitrophenyl)nicotinonitrile

Example 41
2-Amino-6-(2-furyl)-5-(4-methyl-3-nitrophenyl)nicotinonitrile

Example 42
2-Amino-5-(2-fluoro-4-biphenylyl)-6-(2-furyl)nicotinonitrile

Example 43
2-Amino-6-(2-furyl)-5-(4-methylsulfonylphenyl)nicotinonitrile

Example 44
2-Amino-6-(2-furyl)-5-(4-methylsulfinylphenyl)nicotinonitrile

Example 45
2-Amino-5-(4-biphenylyl)-6-(2-furyl)nicotinonitrile

Example 46
2-Amino-5-(3-biphenylyl)-6-(2-furyl)nicotinonitrile

Example 47
2-Amino-5-(3-cyanophenyl)-6-(2-furyl)nicotinonitrile

Example 48
5-(4-Acetylphenyl)-2-amino-6-(2-furyl)nicotinonitrile

Example 49
5-(3-Acetylphenyl)-2-amino-6-(2-furyl)nicotinonitrile

Example 50
5-(2-Acetylphenyl)-2-amino-6-(2-furyl)nicotinonitrile

Example 51
2-Amino-5-(3-formylphenyl)-6-(2-furyl)nicotinonitrile

Example 52
2-Amino-5-(2-formylphenyl)-6-(2-furyl)nicotinonitrile

Example 53
2-Amino-5-(3-chlorophenyl)-6-(2-furyl)nicotinonitrile

Example 54
2-Amino-5-(2-chlorophenyl)-6-(2-furyl)nicotinonitrile

Example 55
2-Amino-5-(2,4-dichlorophenyl)-6-(2-furyl)nicotinonitrile

Example 56
2-Amino-5-(3,4-dichlorophenyl)-6-(2-furyl)nicotinonitrile

Example 57
2-Amino-5-(2,5-dichlorophenyl)-6-(2-furyl)nicotinonitrile

Example 58
2-Amino-5-(4-tert-butylphenyl)-6-(2-furyl)nicotinonitrile

Example 59
2-Amino-6-(2-furyl)-5-(1-naphthyl)nicotinonitrile

Example 60
2-Amino-6-(2-furyl)-5-(2-naphthyl)nicotinonitrile

Example 61
2-Amino-5-benzo[b]furan-2-yl-6-(2-furyl)nicotinonitrile

Example 62
2-Amino-5-dibenzo[b,d]furan-4-yl-6-(2-furyl)nicotinonitrile

Example 63
2-Amino-6-(2-furyl)-5-(3-furyl)nicotinonitrile

Example 64
2-Amino-6-(2-furyl)-5-(2-thienyl)nicotinonitrile

Example 65
2-Amino-6-(2-furyl)-5-(3-thienyl)nicotinonitrile

Example 66
2-Amino-6-(2-furyl)-5-(5-methyl-2-thienyl)nicotinonitrile

Example 67
2-Amino-6-(2-furyl)-5-(4-methyl-2-thienyl)nicotinonitrile

Example 68
5-(5-Acetyl-2-thienyl)-2-amino-6-(2-furyl)nicotinonitrile

Example 69
2-Amino-5-(2-formyl-3-thienyl)-6-(2-furyl)nicotinonitrile

Example 70
2-Amino-5-(3-formyl-2-thienyl)-6-(2-furyl)nicotinonitrile

Example 71
2-Amino-5-(5-chloro-2-thienyl)-6-(2-furyl)nicotinonitrile

Example 72
2-Amino-5-benzo[b]thiophen-2-yl-6-(2-furyl)nicotinonitrile

Example 73
2-Amino-5-benzo[b]thiophen-3-yl-6-(2-furyl)nicotinonitrile

Example 74
2-Amino-6-(2-furyl)-5-(3-pyridyl)nicotinonitrile

Example 75
2-Amino-6-(2-furyl)-5-(2-pyridyl)nicotinonitrile

Example 76
2-Amino-6-(2-furyl)-5-(4-vinylphenyl)nicotinonitrile

Example 77
2-Amino-5-(1-ethyl-6-oxo-1,6-dihydro-3-pyridinyl)-6-(2-furyl)nicotinic acid

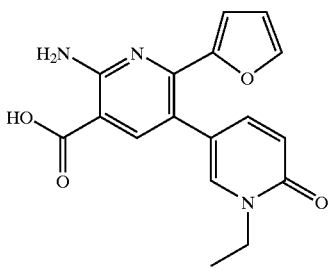

Ethanol (5 mL) and 5 N aqueous sodium hydroxide (10 mL) were added to 2-amino-5-(1-ethyl-6-oxo-1,6-dihydro-3-pyridinyl)-6-(2-furyl)nicotinonitrile (308 mg, 1.01 mmol), followed by heating under reflux for 4 hours. After cooling as it was, the reaction solution was neutralized with 5 N hydrochloric acid. The resulting solid was collected by filtration and then washed with water, to give the title compound (320 mg, 98%) as a yellow solid.
$^1$H-NMR (400 MHz, DMSO-$d_6$) δ ppm; 1.22 (3H, t, J=7.2 Hz), 3.92 (2H, q, J=7.2 Hz) 6.35 (1H, d, J=9.2 Hz), 6.54–6.58 (1H, m), 6.60 (1H, dd, J=0.8, 3.6 Hz), 7.21 (1H, dd, J=2.4, 9.2 Hz), 7.31 (2H, br), 7.71 (1H, d, J=2.4 Hz), 7.73 (1H, dd, J=0.8, 3.6 Hz), 7.93 (1H, s);

The title compounds of the following Examples 78 and 79 were synthesized in the same manner as in the above-mentioned Example 77 or by its analogous method.

Example 78
2-Amino-6-(2-furyl)-5-(6-oxo-1,6-dihydro-3-pyridinyl)nicotinic acid

Example 79
2-Amino-6-(3-fluorophenyl)-5-(4-pyridyl)nicotinonitrile

Example 80
2-Amino-5-(1-ethyl-6-oxo-1,6-dihydro-3-pyridinyl)-6-(2-furyl)nicotinamide

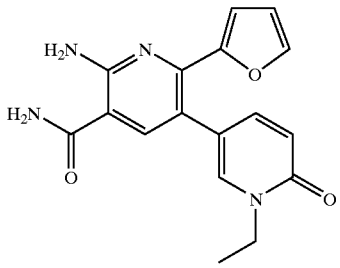

2-Amino-5-(1-ethyl-6-oxo-1,6-dihydro-3-pyridinyl)-6-(2-furyl)nicotinic acid (20 mg, 61.5 μmol), 1-hydroxybenzotriazole (28 mg, 183 μmol), 3-(3'-dimethylaminopropyl)-1-ethyl carbodiimide (29 mg, 187 μmol), ammonium chloride (16 mg, 299 μmol), and a suspension of triethylamine (43 μL, 309 μmol) in N,N-dimethylformamide (1.0 mL) was stirred at room temperature for 18 hours. After diluting the reaction solution with water, the resulting solid was collected by filtration and washed with water, to give the title compound (9 mg, 45%) as a pale yellow solid.
$^1$H-NMR (400 MHz, DMSO-$d_6$) δ ppm; 1.24 (3H, t, J=7.2 Hz), 3.92 (2H, q, J=7.2 Hz), 6.37 (1H, d, J=9.2 Hz), 6.53–6.56 (1H, m), 6.58 (1H, dd, J=0.8, 3.2 Hz), 7.23 (1H, dd, J=2.8, 9.2 Hz), 7.37 (3H, br), 7.67 (1H, d, J=2.8 Hz), 7.70 (1H, dd, J=0.8, 3.2 Hz), 7.93 (1H, s), 7.99 (1H, br);

The title compounds of the following Examples 81 to 102 were obtained in the same manner as in the above-mentioned Example 80 or by its analogous method.

Example 81
2-Amino-6-(3-fluorophenyl)-5-(4-pyridyl)nicotinamide

Example 82
N-(2-Hydroxyethyl)-2-amino-6-(2-furyl)-5-(6-oxo-1,6-dihydro-3-pyridinyl)nicotinamide

Example 83
N—Cyclopropyl-2-amino-6-(2-furyl)-5-(6-oxo-1,6-dihydro-3-pyridinyl)nicotinamide

Example 84
N,N-Dimethyl-2-amino-6-(2-furyl)-5-(6-oxo-1,6-dihydro-3-pyridinyl)nicotinamide

Example 85
N—Cyclopropylmethyl-2-amino-5-(1-ethyl-6-oxo-1,6-dihydro-3-pyridinyl)-6-(2-furyl)nicotinamide

Example 86
N-(2-Fluoroethyl)-2-amino-5-(1-ethyl-6-oxo-1,6-dihydro-3-pyridinyl)-6-(2-furyl)nicotinamide

Example 87
N—Cyclopropyl-2-amino-5-(1-ethyl-6-oxo-1,6-dihydro-3-pyridinyl)-6-(2-furyl)nicotinamide

Example 88
N-(3-Diethylamino)propyl-2-amino-5-(1-ethyl-6-oxo-1,6-dihydro-3-pyridinyl)-6-(2-furyl)nicotinamide

Example 89
N-Methyl-2-amino-5-(1-ethyl-6-oxo-1,6-dihydro-3-pyridinyl)-6-(2-furyl)nicotinamide

Example 90
N-Phenyl-2-amino-5-(1-ethyl-6-oxo-1,6-dihydro-3-pyridinyl)-6-(2-furyl)nicotinamide

Example 91
N-Allyl-2-amino-5-(1-ethyl-6-oxo-1,6-dihydro-3-pyridinyl)-6-(2-furyl)nicotinamide

Example 92
N-(2-Amino-2-oxoethyl)-2-amino-5-(1-ethyl-6-oxo-1,6-dihydro-3-pyridinyl)-6-(2-furyl)nicotinamide

Example 93
N-Isobutyl-2-amino-5-(1-ethyl-6-oxo-1,6-dihydro-3-pyridinyl)-6-(2-furyl)nicotinamide

Example 94
N-(5-Cyanopentyl)-2-amino-5-(1-ethyl-6-oxo-1,6-dihydro-3-pyridinyl)-6-(2-furyl)nicotinamide

Example 95
N-[3-(2-Oxotetrahydro-1H-1-pyrrolyl)propyl]-2-amino-5-(1-ethyl-6-oxo-1,6-dihydro-3-pyridinyl)-6-(2-furyl)nicotinamide

Example 96
N-(2-Pyridylmethyl)-2-amino-5-(1-ethyl-6-oxo-1,6-dihydro-3-pyridinyl)-6-(2-furyl)nicotinamide

Example 97
N-(3-Pyridylmethyl)-2-amino-5-(1-ethyl-6-oxo-1,6-dihydro-3-pyridinyl)-6-(2-furyl)nicotinamide

Example 98
N-[2-(4-Pyridyl)ethyl]-2-amino-5-(1-ethyl-6-oxo-1,6-dihydro-3-pyridinyl)-6-(2furyl)nicotinamide

Example 99
N-[2-(2-Pyridyl)ethyl]-2-amino-5-(1-ethyl-6-oxo-1,6-dihydro-3-pyridinyl)-6-(2furyl)nicotinamide

Example 100
N-(2-Propynyl)-2-amino-5-(1-ethyl-6-oxo-1,6-dihydro-3-pyridinyl)-6-(2-furyl)nicotinamide

Example 101
N-(3-Hydroxypropyl)-2-amino-5-(1-ethyl-6-oxo-1,6-dihydro-3-pyridinyl)-6-(2-furyl)nicotinamide

Example 102
N-Ethyl-2-amino-5-(1-ethyl-6-oxo-1,6-dihydro-3-pyridinyl)-6-(2-furyl)nicotinamide

Example 103
103-(a)
2-Amino-6-(2-furyl)-5-(6-oxo-1-propyl-1,6-dihydro-3-pyridinyl)nicotinonitrile

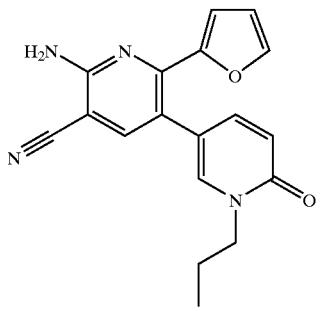

103-(b)

2-Amino-6-(2-furyl)-5-(4-propyl-3-pyridyl)-3-pyridinecarbonitrile

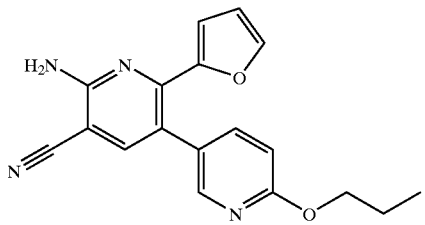

2-Amino-6-(2-furyl)-5-(6-oxo-1,6-dihydro-3-pyridinyl)nicotinonitrile (20 mg, 0.072 mmol) and potassium carbonate (30 mg, 0.22 mmol) were introduced into a reaction vessel, dissolved in N,N-dimethylformamide (1 mL). Propyl iodide (52 mg, 0.31 mmol) was added thereto, followed by stirring at 70° C. for 18 hours. After the reaction was finished, water was added thereto, and it was extracted with ethyl acetate. After removing the aqueous layer, the organic layer was concentrated and purified by high performance liquid chromatography, to give the title product as a yellow solid (2.6 mg, 11%; 1.8 mg, 7.8%).

103-(a)

2-Amino-6-(2-furyl)-5-(6-oxo-1-propyl-1,6-dihydro-3-pyridinyl)nicotinonitrile $^1$H-NMR (400 MHz, CDCl$_3$) δ ppm; 0.98 (3H, t, J=7.4 Hz), 1.83 (2H, q, J=7.4 Hz), 3.99 (2H, t, J=7.4 Hz), 5.50 (2H, brs), 6.47 (1H, dd, J=3.6, 1.8 Hz), 6.73 (1H, dd, J=3.6, 0.8 Hz), 6.81 (1H, d, J=9.2 Hz), 7.26 (1H, m), 7.30 (1H, dd, J=9.2, 2.4 Hz), 7.46 (1H, dd, J=1.8, 0.8 Hz), 7.58 (1H, s);

MS (ESI) m/e 321 (MH$^+$).

103-(b)

2-Amino-6-(2-furyl)-5-(4-propyl-3-pyridyl)-3-pyridinecarbonitrile $^1$H-NMR (400 MHz, CDCl$_3$) δ ppm; 1.07 (3H, t, J=7.4 Hz), 1.85 (2H, m), 4.30 (2H, t, J=6.6 Hz), 6.38–6.41 (2H, m), 6.81 (1H, dd, J=8.8, 0.8 Hz), 7.46–7.48 (2H, m), 7.62 (1H, s), 8.06 (1H, d, J=0.8 Hz)

MS (ESI) m/e 321 (MH$^+$).

Example 104
2-Amino-5-[1-(4-cyanophenyl)-6-oxo-1,6-dihydro-3-pyridinyl]-6-(2-furyl)nicotinonitrile

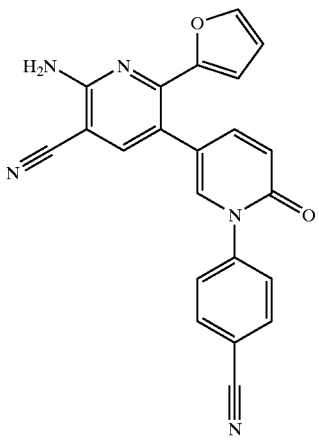

2-Amino-6-(2-furyl)-5-(6-oxo-1,6-dihydro-3-pyridinyl) nicotinonitrile (20 mg, 0.071 mmol), 4-cyanophenylboronic acid (35 mg, 0.24 mmol), copper acetate monohydrate (3.0 mg, 0.015 mmol), pyridine (0.015 mL, 0.19 mmol) and N,N-dimethylformamide (1.0 mL) were introduced into a reaction vessel and stirred at room temperature for 20 hours. Water was added to the reaction solution, followed by extracting with ethyl acetate. The organic layer was dried, and then dissolved in dimethyl sulfoxide (1.0 mL) and purified by high performance liquid chromatography, to give the title compound as a yellow solid (8.32 mg, 62%).

$^1$H-NMR (400 MHz, DMSO-$d_6$) δ ppm: 6.49 (1H, d, J=9.6 Hz), 6.61 (1H, dd, J=1.6, 3.2 Hz), 6.79 (1H, d, J=3.2 Hz), 7.07 (2H, brs), 7.30 (1H, dd, J=2.6, 9.6 Hz), 7.74 (1H, d, J=2.6 Hz), 7.76 (2H, d, J=8.6 Hz), 7.82 (1H, d, J=1.6 Hz), 7.98 (1H, s), 8.02 (2H, d, J=8.6 Hz);

MS (ESI) m/e 380 (MH$^+$).

The title compounds of the following Examples 105 to 146 were obtained in the same manner as in the above-mentioned Example 5, 103 or 104, or by its analogous methods.

Example 105
2-Amino-6-(2-furyl)-5-[6-oxo-1-(3-phenylpropyl)-1,6-dihydro-3-pyridinyl]nicotinonitrile

Example 106
Ethyl 4–5-[6-amino-5-cyano-2-(2-furyl)-3-pyridyl]-2-oxo-1,2-dihydro-1-pyridinylbutanoate

Example 107
2-Amino-5-[1-(3-cyanopropyl)-6-oxo-1,6-dihydro-3-pyridinyl]-6-(2-furyl)nicotinonitrile

Example 108
2-Amino-5-[1-(3-cyanobutylpropyl)-6-oxo-1,6-dihydro-3-pyridinyl]-6-(2-furyl)nicotinonitrile

Example 109
2-Amino-6-(2-furyl)-5-[6-oxo-1-(4,4,4-trifluorobutyl)-1,6-dihydro-3-pyridinyl]nicotinonitrile

Example 110
2-Amino-6-(2-furyl)-5-[6-oxo-1-(3,4,4-trifluoro-3-butenyl)-1,6-dihydro-3-pyridinyl]nicotinonitrile

Example 111
2-Amino-6-(2-furyl)-5-[6-oxo-1-(3,3,3-trifluoropropyl)-1,6-dihydro-3-pyridinyl]nicotinonitrile

Example 112
2-Amino-5-(1-butyl-6-oxo-1,6-dihydro-3-pyridinyl)-6-(2-furyl)nicotinonitrile

Example 113
2-Amino-6-(2-furyl)-5-(1-heptyl-6-oxo-1,6-dihydro-3-pyridinyl)nicotinonitrile

Example 114
2-Amino-6-(2-furyl)-5-(1-isopentyl-6-oxo-1,6-dihydro-3-pyridinyl)nicotinonitrile

Example 115
5-(1-Allyl-6-oxo-1,6-dihydro-3-pyridinyl)-2-amino-6-(2-furyl)nicotinonitrile

Example 116
2-Amino-5-[1-(3-butenyl)-6-oxo-1,6-dihydro-3-pyridinyl]-6-(2-furyl)nicotinonitrile

Example 117
2-Amino-6-(2-furyl)-5-[6-oxo-1-(4-pentenyl)-1,6-dihydro-3-pyridinyl]nicotinonitrile

Example 118
2-Amino-6-(2-furyl)-5-[1-(3-hydroxypropyl)-6-oxo-1,6-dihydro-3-pyridinyl]nicotinonitrile

Example 119
2-Amino-5-[1-(2,3-dihydroxypropyl)-6-oxo-1,6-dihydro-3-pyridinyl]-6-(2-furyl)nicotinonitrile

Example 120
2-Amino-5-[1-(3-fluoropropyl)-6-oxo-1,6-dihydro-3-pyridinyl]-6-(2-furyl)nicotinonitrile

Example 121
2-Amino-5-[1-(3-chloropropyl)-6-oxo-1,6-dihydro-3-pyridinyl]-6-(2-furyl)nicotinonitrile

Example 122
2-Amino-5-[1-(4-chlorobutyl)-6-oxo-1,6-dihydro-3-pyridinyl]-6-(2-furyl)nicotinonitrile

Example 123
2-Amino-5-[1-(5-chloropentyl)-6-oxo-1,6-dihydro-3-pyridinyl]-6-(2-furyl)nicotinonitrile

Example 124
2-Amino-5-[1-(cyclohexylmethyl)-6-oxo-1,6-dihydro-3-pyridinyl]-6-(2-furyl)nicotinonitrile

Example 125
2-Amino-6-(2-furyl)-5-[6-oxo-1-(tetrahydro-2H-2-pyranylmethyl)-1,6-dihydro-3-pyridinyl)nicotinonitrile

Example 126
2-Amino-5-(1-benzyl-6-oxo-1,6-dihydro-3-pyridinyl)-6-(2-furyl)nicotinonitrile

Example 127
2-Amino-5-[1-(2-cyanoethyl)-6-oxo-1,6-dihydro-3-pyridinyl]-6-(2-furyl)nicotinonitrile

Example 128
2-Amino-6-(2-furyl)-5-[6-oxo-1-(2-propynyl)-1,6-dihydro-3-pyridinyl]nicotinonitrile

Example 129
2-Amino-5-[1-(2-butynyl)-6-oxo-1,6-dihydro-3-pyridinyl]-6-(2-furyl)nicotinonitrile

Example 130
2-Amino-6-(2-furyl)-5-{6-oxo-1-[3-(1,1,1-trimethylsilyl)-2-propynyl]-1,6-dihydro-3-pyridinyl}nicotinonitrile

Example 131
2-Amino-5-{1-[(6,7-dimethoxy-2-oxo-2H-4-chromenyl)methyl]-6-oxo-1,6-dihydro-3pyridinyl}nicotinonitrile

Example 132
2-Amino-5-{1-[4-(1,3-dioxo-2,3-dihydro-1H-2-isoindolyl)butyl]-6-oxo-1,6-dihydro-3-pyridinyl}-6-(2-furyl)nicotinonitrile

Example 133
2-Amino-6-(2-furyl)-5–1-[2-(1H-3-indolyl)ethyl]-6-oxo-{1,6-dihydro-3-pyridinyl}nicotinonitrile

Example 134
2-Amino-6-(2-furyl)-5-[6-oxo-1-(2-oxopropyl)-1,6-dihydro-3-pyridinyl]nicotinonitrile

Example 135
2-Amino-6-(2-furyl)-5-{6-oxo-1–2-oxo-2-[4-(trifluoromethyl)phenyl]ethyl-1,6-dihydro-3-pyridinyl}nicotinonitrile

Example 136
2-Amino-6-(2-furyl)-5-(6-oxo-1-phenyl-1,6-dihydro-3-pyridinyl)-6-(2-furyl)nicotinonitrile

Example 137
2-Amino-5-[1-(4-cyanophenyl)-6-oxo-1,6-dihydro-3-pyridinyl]-6-(2-furyl)nicotinonitrile

Example 138
2-Amino-6-(2-furyl)-5-[6-oxo-1-(4-vinylphenyl)-1,6-dihydro-3-pyridinyl]nicotinonitrile

Example 139
2-Amino-6-(2-furyl)-5-[1-(4-methylphenyl)-6-oxo-1,6-dihydro-3-pyridinyl]nicotinonitrile

Example 140
2-Amino-6-(2-furyl)-5-[1-(2-methylphenyl)-]6-oxo-1,6-dihydro-3-pyridinyl)nicotinonitrile

Example 141
2-Amino-6-(2-furyl)-5-[1-(4-methoxyphenyl)-6-oxo-1,6-dihydro-3-pyridinyl]nicotinonitrile

Example 142
2-Amino-6-(2-furyl)-5-[1-(3-methoxyphenyl)-6-oxo-1,6-dihydro-3-pyridinyl]nicotinonitrile

Example 143
2-Amino-6-(2-furyl)-5-[1-(2-methoxyphenyl)-6-oxo-1,6-dihydro-3-pyridinyl]nicotinonitrile

Example 144
2-Amino-5-[1-(4-fluorophenyl)-6-oxo-1,6-dihydro-3-pyridinyl]-6-(2-furyl)nicotinonitrile

Example 145
2-Amino-5-[1-(3-fluorophenyl)-6-oxo-1,6-dihydro-3-pyridinyl]-6-(2-furyl)nicotinonitrile

Example 146
2-Amino-5-[1-(2-fluorophenyl)-6-oxo-1,6-dihydro-3-pyridinyl]-6-(2-furyl)nicotinonitrile The title compounds of the following Examples 147 to 175 were obtained in the same manner as in the above-mentioned Example 103 or by its analogous method.

Example 147
6-Amino-2-(2-furyl)-6'-(3-phenylpropoxy)-[3,3']bipyridinyl-5-carbonitrile

Example 148
Ethyl 4-(6'-amino-5'-cyano-2'-(2-furyl)-[3,3']bipyridinyl-6-yloxy)butyrate

Example 149
6-Amino-6'-(3-cyanopropoxy)-2-(2-furyl)-[3,3']bipyridinyl-5-carbonitrile

Example 150
6-Amino-6'-cyclobutylmethoxy-2-(2-furyl)-[3,3']bipyridinyl-5-carbonitrile

Example 151
6-Amino-2-(2-furyl)-6'-(4,4,4-trifluorobutoxy)-[3,3']bipyridinyl-5-carbonitrile

Example 152
6-Amino-2-(2-furyl)-6'-(3,4,4-trifluoro-3-butenyloxy)-[3,3']bipyridinyl-5-carbonitrile

Example 153
6-Amino-2-(2-furyl)-6'-(3,3,3-trifluoropropoxy)-[3,3']bipyridinyl-5-carbonitrile

Example 154
6-Amino-6'-butoxy-2-(2-furyl)-[3,3']bipyridinyl-5-carbonitrile

Example 155
6-Amino-2-(2-furyl)-6'-heptyloxy-[3,3']bipyridinyl-5-carbonitrile

Example 156
6-Amino-2-(2-furyl)-6'-(3-methylbutoxy)-[3,3']bipyridinyl-5-carbonitrile

Example 157
6'-Allyloxy-6-amino-2-(2-furyl)-[3,3']bipyridinyl-5-carbonitrile

Example 158
6-Amino-6'-(3-butenyloxy)-2-(2-furyl)-[3,3']bipyridinyl-5-carbonitrile

Example 159
6-Amino-2-(2-furyl)-6'-(4-pentenyloxy)-[3,3']bipyridinyl-5-carbonitrile

Example 160
6-Amino-2-(2-furyl)-6'-(3-hydroxypropoxy)-[3,3']bipyridinyl-5-carbonitrile

Example 161
6-Amino-6'-(2,3-dihydroxypropoxy)-2-(2-furyl)-[3,3']bipyridinyl-5-carbonitrile

Example 162
6-Amino-6'-(3-fluoropropoxy)-2-(2-furyl)-[3,3']bipyridinyl-5-carbonitrile

Example 163
6-Amino-6'-(3-chloropropoxy)-2-(2-furyl)-[3,3']bipyridinyl-5-carbonitrile

Example 164
6-Amino-6'-(4-chlorobutoxy)-2-(2-furyl)-[3,3']bipyridinyl-5-carbonitrile

Example 165
6-Amino-6'-(5-chloropentyloxy)-2-(2-furyl)-[3,3']bipyridinyl-5-carbonitrile

Example 166
6-Amino-6'-cyclohexyloxy-2-(2-furyl)-[3,3']bipyridinyl-5-carbonitrile

Example 167
6-Amino-2-(2-furyl)-6'-(2-tetrahydropyranyloxy)-[3,3']bipyridinyl-5-carbonitrile

Example 168
6-Amino-2-(2-furyl)-6'-(2-propynyloxy)-[3,3']bipyridinyl-5-carbonitrile

Example 169
6-Amino-6'-(2-butynyloxy)-2-(2-furyl)-[3,3']bipyridinyl-5-carbonitrile

Example 170
6-Amino-2-(2-furyl)-6'-(3-trimethylsilanyl-2-propynyloxy)-[3,3']bipyridinyl-5-carbonitrile

Example 171
6-Amino-6'-(6,7-dimethoxy-2-oxo-2H-chromen-4-ylmethoxy)-2-(2-furyl)-[3,3']bipyridinyl-5carbonitrile

Example 172
6-Amino-6'-[4-(1,3-dioxo-1,3-dihydro-2-isoindolyl)butoxy]-2-(2-furyl)-[3,3']bipyridinyl-5carbonitrile

Example 173
6-Amino-2-(2-furyl)-6'-[2-(1H-3-indolyl)ethoxy]-[3,3']bipyridinyl-5-carbonitrile

Example 174
6-Amino-2-(2-furyl)-6'-(2-oxopropyl)-[3,3']bipyridinyl-5-carbonitrile

Example 175
6-Amino-2-(2-furyl)-6'-[2-[4-(trifluoromethyl)phenyl]ethoxy]-[3,3']bipyridinyl-5-carbonitrile

Example 176
2-Amino-4,6-di(3-fluorophenyl)-5-(4-methoxy-3-pyridyl)-3-pyridinecarbonitrile

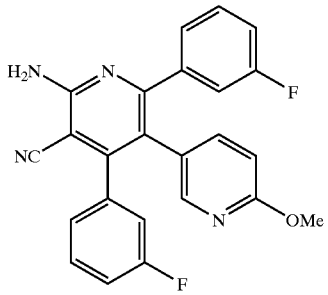

The title compound was obtained in the same manners as in Reference Examples 6 to 9 and Example 3, or by analogous methods of these.
$^1$H NMR (400 MHz, DMSO-d$_6$) δ ppm; 3.81 (3H, s), 5.43 (2H, br s), 6.41–6.46 (1H, m), 6.79–6.83 (1H, m), 6.88–7.04 (6H, m), 7.17 (1H, dt, J=2.4, 5.9 Hz), 7.29 (1H, dt, J=2.4, 5.9 Hz), 7.53–7.57 (1H, m).

Example 177
2-Amino-4,6-di(3-fluorophenyl)-5-(6-oxo-1,6-dihydro-3-pyridyl)nicotinonitrile hydrobromide

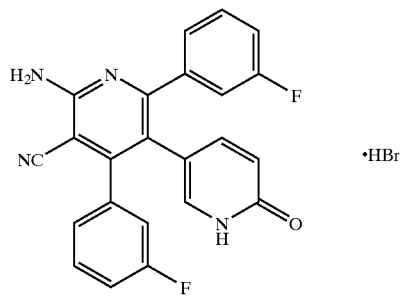

The title compound was obtained in the same manner as in Example 4 or by its analogous method.
$^1$H NMR (400 MHz, DMSO-d$_6$) δ ppm; 6.01 (1H, d, J=9.4 Hz), 6.86 (1H, d, J=2.4 Hz), 6.93 (1H, dd, J=2.4, 9.4 Hz), 7.04–7.24 (6H, m), 7.32–7.39 (1H, m), 7.40–7.47 (1H, m).

Example 178
2-Amino-6-(2-furyl)-4-isopropoxy-5-(4-methoxy-3-pyridyl)-3-pyridinecarbonitrile

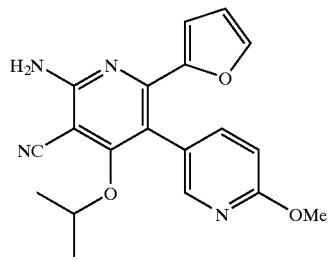

Using 6-(2-furyl)-4-isopropoxy-2-oxo-1,2-dihydro-3-pyridinecarbonitrile, the title compound was obtained in the same manner as in Reference Examples 7 to 9 and Example 3, or by its analogous method.
$^1$H NMR (400 MHz, DMSO-d$_6$) δ ppm; 1.12 (6H, d, J=8.1 Hz), 3.98 (3H, s), 4.58–4.65 (1H, m), 5.44 (2H, br s), 5.97 (1H, d, J=3.3 Hz), 6.29 (1H, dd, J=1.8, 3.3 Hz), 6.81 (1H, d, J=8.4 Hz), 7.37–7.43 (2H, m), 7.96 (1H, d, J=1.8 Hz).

Example 179
2-Amino-6-(2-furyl)-4-hydroxy-5-(6-oxo-1,6-dihydro-3-pyridinyl)nicotinonitrile hydrobromide

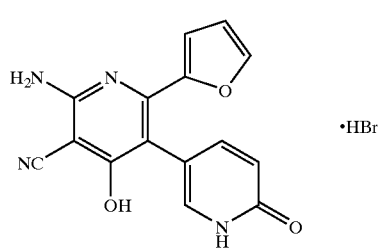

Using 2-amino-6-(2-furyl)-4-isopropoxy-5-(4-methoxy-3-pyridyl)-3-pyridinecarbonitrile, the title compound was obtained in the same manner as in Example 4 or by its analogous method.

¹H NMR (400 MHz, DMSO-d₆) δ ppm; 6.20 (1H, d, J=3.7 Hz), 6.31 (1H, d, J=9.3 Hz), 6.61 (1H, dd, J=1.5, 3.7 Hz), 7.01 (2H, br s), 7.08 (1H, dd, J=2.4, 9.3 Hz), 7.12 (1H, d, J=2.4 Hz), 7.92 (1H, d, J=1.5 Hz), 10.79 (1H, br s).

Example 180

2-Amino-6-(3-fluorophenyl)-4-isopropoxy-5-(4-methoxy-3-pyridyl)-3-pyridinecarbonitrile

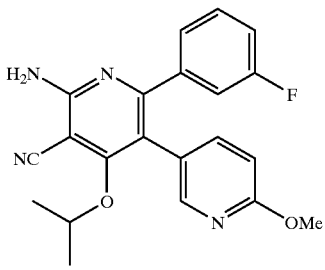

The title compound was obtained in the same manner as in Examples 14 to 16, Reference Examples 7 to 9 and Example 3 or by analogous method of these.

¹H NMR (400 MHz, DMSO-d₆) δ ppm; 1.13 (6H, d, J=8.1 Hz), 3.95 (3H, s), 4.44–4.58 (1H, m), 5.28 (2H, br s), 6.66 (1H, d, J=8.6 Hz), 6.89–7.01 (3H, m), 7.16 (1H, dt, J=5.9, 8.0 Hz), 7.28 (1H, dd, J=1.6, 8.6 Hz), 7.79–7.81 (1H, m).

Example 181

2-Amino-6-(3-fluorophenyl)-4-hydroxy-5-(6-oxo-1,6-dihydro-3-pyridinyl)nicotinonitrile hydrobromide

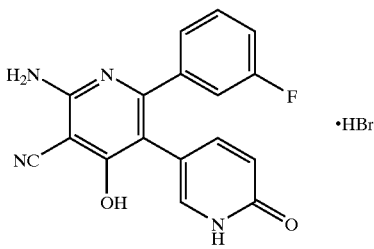

Using 2-amino-6-(3-fluorophenyl)-4-isopropoxy-5-(4-methoxy-3-pyridyl)-3-pyridinecarbonitrile, the title compound was obtained in the same manner as in Example 4 or by its analogous method.

¹H NMR (400 MHz, DMSO-d₆) δ ppm; 6.10 (1H, d, J=9.6 Hz), 6.75–6.80 (1H, m), 6.89–6.93 (1H, m), 6.99 (1H, dd, J=2.7, 9.6 Hz), 7.12 (1H, d, J=7.4 Hz), 7.22–7.29 (2H, m), 7.41–7.48 (1H, m), 10.95 (1H, s).

Example 182
2-Amino-6-(3-fluorophenyl)-5-(4-methoxy-3-pyridyl)-3-pyridinecarbonitrile

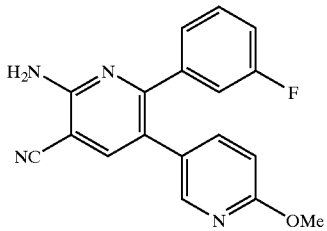

The title compound was obtained in the same manners as in Reference Examples 7 to 9 and Example 3 or by its analogous methods.

¹H NMR (400 MHz, DMSO-d₆) δ ppm; 3.82 (3H, s), 6.71 (1H, d, J=8.4 Hz), 6.99–7.04 (1H, m), 7.08–7.20 (4H, m), 7.28–7.35 (1H, m), 7.36 (1H, dd, J=2.5, 8.4 Hz), 7.95 (1H, d, J=2.5 Hz), 8.01 (1H, s);
MS m/e(ESI) 321 (MH⁺).

Example 183
2-Amino-6-(3-fluorophenyl)-5-(6-oxo-1,6-dihydro-3-pyridinyl)nicotinonitrile

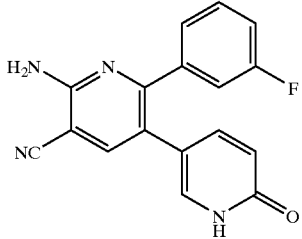

Using 2-amino-6-(3-fluorophenyl)-5-(4-methoxy-3-pyridyl)-3-pyridinecarbonitrile, the title compound was obtained in the same manner as in Example 4 or by its analogous method.

¹H NMR (400 MHz, DMSO-d₆) δ ppm; 6.15 (1H, d, J=8.2 Hz), 6.94–7.02 (1H m), 7.04–7.28 (6H, m), 7.34–7.44 (1H, m), 7.97 (1H, s);
MS m/e(ESI) 307 (MH⁺).

Example 184
2-Amino-6-(3-fluorophenyl)-5-(6-oxo-1,6-dihydro-3-pyridinyl)nicotinonitrile

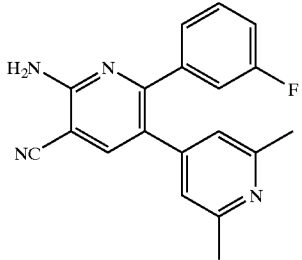

The title compound was obtained in the same manner as in Reference Examples 1 to 4 and Example 1, or by its analogous method.

¹H NMR (400 MHz, DMSO-d₆) δ ppm; 2.30 (6H, s), 6.78 (2H, s), 7.01 (1H, d, J=8.0 Hz), 7.10–7.16 (1H m), 7.17–7.23 (1H, m), 7.26 (2H, s), 7.29–7.35 (1H, m), 8.03 (1H, s); MS m/e(ESI) 319 (MH⁺).

The structural formulae of the title compounds of the above-mentioned Examples 1 to 8, 10 to 76, 78, 79, 81 to 102, 105 to 175 are shown below.

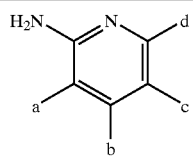

| Example No. | a | b | c | d |
|---|---|---|---|---|
| 1 | -CN | -H | 4-pyridyl | 2-furyl |
| 2 | -CN | -H | 4-pyridyl | 3-fluorophenyl |
| 3 | -CN | -H | 6-methoxy-3-pyridyl | 2-furyl |
| 4 | -CN | -H | 6-oxo-1H-pyridin-3-yl | 2-furyl |
| 5 | -CN | -H | 1-ethyl-6-oxo-pyridin-3-yl | 2-furyl |
| 6 | -CN | -H | 1-methyl-6-oxo-pyridin-3-yl | 2-furyl |
| 7 | -CN | -H | 1-ethyl-6-oxo-pyridin-3-yl | 3-fluorophenyl |
| 8 | -CN | -H | 1-methyl-6-oxo-pyridin-3-yl | 3-fluorophenyl |

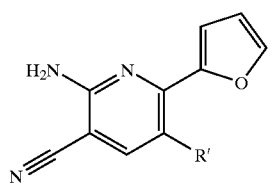

| Example No. | R' | MS m/e (ESI, MH+) |
|---|---|---|
| 10 | 2-Furyl | 366 |
| 11 | 4-Cyanophenyl | 401 |
| 12 | Phenyl | 262 |
| 13 | 4-Methylphenyl | 276 |
| 14 | 3-Methylphenyl | 276 |
| 15 | 2-Methylphenyl | 276 |
| 16 | 4-Methoxyphenyl | 292 |
| 17 | 3-Methoxyphenyl | 292 |
| 18 | 2,4-Dimethoxyphenyl | 322 |
| 19 | 3,4-Dimethoxyphenyl | 322 |

-continued

| | | |
|---|---|---|
| 20 | 3,4,5-Trimethoxyphenyl | 352 |
| 21 | 3,4-Methylenedioxyphenyl | 306 |
| 22 | 4-Benzyloxyphenyl | 368 |
| 23 | 3-Benzyloxyphenyl | 368 |
| 24 | 4-Phenoxyphenyl | 354 |
| 25 | 3-Ethoxyphenyl | 306 |
| 26 | 4-Trifluoromethoxyphenyl | 346 |
| 27 | 3-Trifluoromethoxyphenyl | 346 |
| 28 | 4-Dimethylaminophenyl | 305 |
| 29 | 4-Thiomethylphenyl | 308 |
| 30 | 4-Fluorophenyl | 280 |
| 31 | 3-Fluorophenyl | 280 |
| 32 | 2-Fluorophenyl | 280 |
| 33 | 2,4-Difluorophenyl | 298 |
| 34 | 2,3,4,5-Pentafluoraphenyl | 352 |
| 35 | 4-Trifluoromethylphenyl | 330 |
| 36 | 3-Trifluoromethylphenyl | 330 |
| 37 | 2-Trifluoromethylphenyl | 330 |
| 38 | 3,5-Bis(trifluoromethyl)phenyl | 398 |
| 39 | 4-Nitrophenyl | 307 |
| 40 | 3-Nitrophenyl | 307 |
| 41 | 3-Nitro-4-methylphenyl | 321 |
| 42 | 2-Fluoro-4-biphenylyl | 356 |
| 43 | 4-Methanesulfonylphenyl | 340 |
| 44 | 4-Methanesulfinylphenyl | 324 |
| 45 | 4-Biphenylyl | 338 |
| 46 | 3-Biphenylyl | 338 |
| 47 | 3-Cyanophenyl | 287 |
| 48 | 4-Acetylphenyl | 304 |
| 49 | 3-Acetylphenyl | 304 |
| 50 | 2-Acetylphenyl | 304 |
| 51 | 3-Formylphenyl | 290 |
| 52 | 2-Formylphenyl | 290 |
| 53 | 3-Chlorophenyl | 296 |
| 54 | 2-Chlorophenyl | 296 |
| 55 | 2,4-Dichlorophenyl | 330 |
| 56 | 3,4-Dichlorophneyl | 330 |
| 57 | 3,5-Dichlorophneyl | 330 |
| 58 | 4-tert-Butylpheyl | 318 |
| 59 | 1-Naphthyl | 312 |
| 60 | 2-Naphthyl | 312 |
| 61 | 2-Benzofuranyl | 302 |
| 62 | 4-Dibenzofuranyl | 352 |
| 63 | 3-Furyl | 252 |
| 64 | 2-Thienyl | 268 |
| 65 | 3-Thienyl | 268 |
| 66 | 5-Methyl-2-thienyl | 282 |
| 67 | 4-Methyl-2-thienyl | 282 |
| 68 | 5-Acetyl-2-thienyl | 310 |
| 69 | 2-Formyl-3-thienyl | 296 |
| 70 | 3-Formyl-2-thienyl | 296 |
| 71 | 5-Chloro-2-thienyl | 302 |
| 72 | 2-Benzothiophenyl | 318 |
| 73 | 3-Benzothiophenyl | 318 |
| 74 | 3-Pyridyl | 263 |
| 75 | 2-Pyridyl | 263 |
| 76 | 4-Vinylphenyl | 288 |

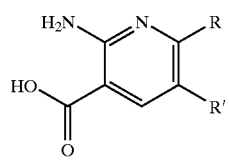

| Example No. | R | R' | MS m/e (MH$^+$) |
|---|---|---|---|
| 78 | (2-furyl) | (2-oxo-1,2-dihydropyridin-5-yl) | 298 (ESI) |

-continued

| | | | | |
|---|---|---|---|---|
| 79 | 3-fluorophenyl | pyridin-4-yl | | 310 (FAB) |

Structure: 2-amino-pyridine-3-carboxamide with R at 6-position, R' at 5-position, and N(R")(R''') on the carboxamide nitrogen.

| Example No. | R | R' | R" | R''' | MS m/e (MH+) |
|---|---|---|---|---|---|
| 81 | 3-fluorophenyl | pyridin-4-yl | H | H | 309 (FAB) |
| 82 | furan-2-yl | 2-oxo-1,2-dihydropyridin-5-yl (NH) | -CH₂CH₂OH | H | 341 (ESI) |
| 83 | furan-2-yl | 2-oxo-1,2-dihydropyridin-5-yl (NH) | cyclopropyl | H | 337 (ESI) |
| 84 | furan-2-yl | 2-oxo-1,2-dihydropyridin-5-yl (NH) | Me | Me | 325 (ESI) |
| 85 | furan-2-yl | 1-ethyl-2-oxo-1,2-dihydropyridin-5-yl | -CH₂-cyclopropyl | H | 379 (ESI) |
| 86 | furan-2-yl | 1-ethyl-2-oxo-1,2-dihydropyridin-5-yl | -CH₂CH₂F | H | 371 (ESI) |
| 87 | furan-2-yl | 1-ethyl-2-oxo-1,2-dihydropyridin-5-yl | cyclopropyl | H | 365 (ESI) |
| 88 | furan-2-yl | 1-ethyl-2-oxo-1,2-dihydropyridin-5-yl | -CH₂CH₂CH₂-N(Et)₂ | H | 438 (ESI) |

| | | | | | |
|---|---|---|---|---|---|
| 89 | furan-2-yl | 1-Et-2-oxo-pyridin-5-yl, N-Me | | H | 339 (ESI) |
| 90 | furan-2-yl | 1-Et-2-oxo-pyridin-5-yl, N-Ph | | H | 401 (ESI) |
| 91 | furan-2-yl | 1-Et-2-oxo-pyridin-5-yl | allyl | H | 365 (ESI) |
| 92 | furan-2-yl | 1-Et-2-oxo-pyridin-5-yl | CH₂C(O)NH₂ | H | 382 (ESI) |
| 93 | furan-2-yl | 1-Et-2-oxo-pyridin-5-yl | isobutyl | H | 381 (ESI) |
| 94 | furan-2-yl | 1-Et-2-oxo-pyridin-5-yl | (CH₂)₅CN | H | 420 (ESI) |
| 95 | furan-2-yl | 1-Et-2-oxo-pyridin-5-yl | (CH₂)₃-(2-oxopyrrolidin-1-yl) | H | 450 (ESI) |
| 96 | furan-2-yl | 1-Et-2-oxo-pyridin-5-yl | CH₂-(pyridin-2-yl) | H | 416 (ESI) |
| 97 | furan-2-yl | 1-Et-2-oxo-pyridin-5-yl | CH₂-(pyridin-4-yl) | H | 416 (ESI) |

-continued
| | | | | | |
|---|---|---|---|---|---|
| 98 | furan | 1-Et-pyridin-2-one | (CH2)2-(4-pyridyl) | H | 430 (ESI) |
| 99 | furan | 1-Et-pyridin-2-one | (CH2)2-(2-pyridyl) | H | 430 (ESI) |
| 100 | furan | 1-Et-pyridin-2-one | CH2-C≡CH | H | 363 (ESI) |
| 101 | furan | 1-Et-pyridin-2-one | (CH2)3OH | H | 383 (ESI) |
| 102 | furan | 1-Et-5-Et-pyridin-2-one | | H | 353 (ESI) |
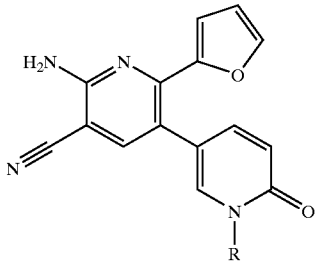
| Example No. | R | MS m/e (ESI, MH+) |
|---|---|---|
| 105 | (CH2)3Ph | 397 |
| 106 | (CH2)3COOEt | 393 |
| 107 | (CH2)3CN | 346 |
| 108 | (CH2)3c-C4H7 | 347 |
| 109 | (CH2)3CF3 | 389 |
| 110 | (CH2)2CF=CF2 | 387 |
| 111 | (CH2)2CF3 | 375 |
| 112 | n-pentyl | 335 |
| 113 | n-octyl | 377 |

| | | |
|---|---|---|
| 114 | 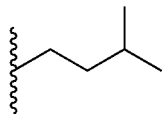 | 349 |
| 115 | 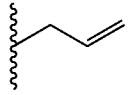 | 319 |
| 116 | 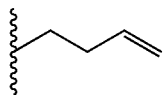 | 333 |
| 117 | 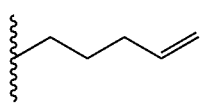 | 347 |
| 118 | 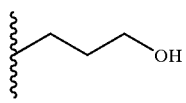 | 337 |
| 119 | 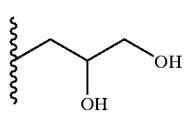 | 353 |
| 120 | 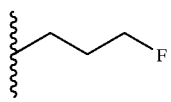 | 339 |
| 121 | 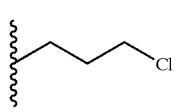 | 355 |
| 122 | 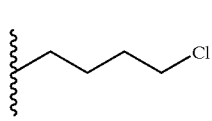 | 369 |
| 123 | 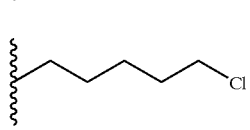 | 383 |
| 124 | 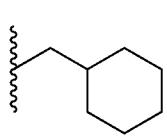 | 375 |
| 125 | 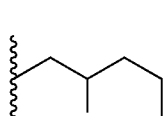 | 377 |
| 126 | 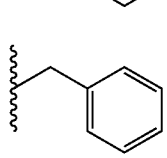 | 369 |

-continued
| | | |
|---|---|---|
| 127 | 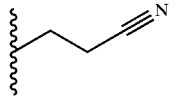 | 332 |
| 128 | 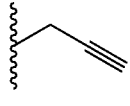 | 317 |
| 129 | 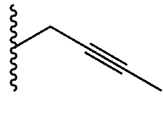 | 331 |
| 130 | 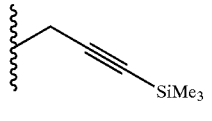 | 389 |
| 131 | 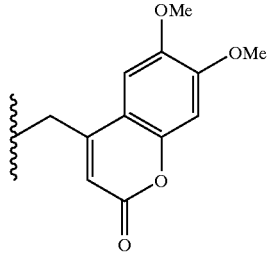 | 497 |
| 132 | 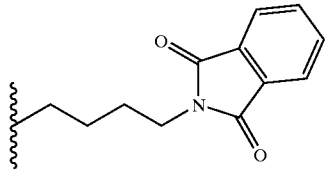 | 480 |
| 133 | 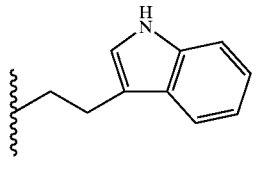 | 422 |
| 134 | 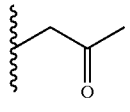 | 335 |
| 135 | 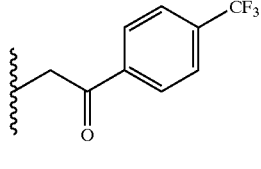 | 465 |
| 136 | 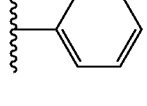 | 355 |
| 137 | 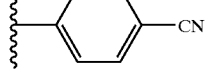 | 380 |

-continued
| | | |
|---|---|---|
| 138 | 4-vinylphenyl | 381 |
| 139 | 4-methylphenyl | 369 |
| 140 | 2-methylphenyl | 369 |
| 141 | 4-methoxyphenyl | 385 |
| 142 | 3-methoxyphenyl | 385 |
| 143 | 2-methoxyphenyl | 380 |
| 144 | 4-fluorophenyl | 373 |
| 145 | 3-fluorophenyl | 373 |
| 146 | 2-fluorophenyl | 373 |
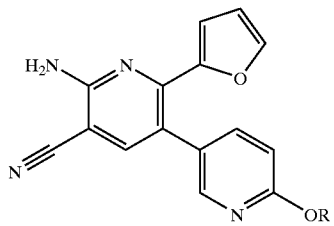
| Example No. | R | MS m/e (ESI, MH+) |
|---|---|---|
| 147 | (CH$_2$)$_3$Ph | 397 |
| 148 | (CH$_2$)$_3$COOEt | 393 |
| 149 | (CH$_2$)$_3$CN | 346 |
| 150 | (CH$_2$)$_3$c-C$_4$H$_7$ | 347 |

-continued

| | | |
|---|---|---|
| 151 | (CH$_2$)$_3$CF$_3$ | 389 |
| 152 | (CH$_2$)$_2$CF=CF$_2$ | 387 |
| 153 | (CH$_2$)$_2$CF$_3$ | 375 |
| 154 | n-pentyl | 335 |
| 155 | n-octyl | 377 |
| 156 | isopentyl | 349 |
| 157 | allyl | 319 |
| 158 | but-3-enyl | 333 |
| 159 | pent-4-enyl | 347 |
| 160 | (CH$_2$)$_3$OH | 337 |
| 161 | CH$_2$CH(OH)CH$_2$OH | 353 |
| 162 | (CH$_2$)$_3$F | 339 |
| 163 | (CH$_2$)$_3$Cl | 355 |
| 164 | (CH$_2$)$_5$Cl | 369 |
| 165 | (CH$_2$)$_6$Cl | 383 |
| 166 | CH$_2$-cyclohexyl | 375 |

| | | |
|---|---|---|
| | -continued | |
| 167 | [tetrahydropyran-2-ylmethyl] | 377 |
| 168 | [CH2-C≡CH] | 317 |
| 169 | [CH2-C≡C-CH3] | 331 |
| 170 | [CH2-C≡C-SiMe3] | 389 |
| 171 | [4-(6,7-dimethoxycoumarin-4-yl)methyl] | 497 |
| 172 | [N-phthalimidobutyl] | 480 |
| 173 | [2-(1H-indol-3-yl)ethyl] | 422 |
| 174 | [CH2-C(=O)-CH3] | 335 |
| 175 | [CH2-C(=O)-C6H4-4-CF3] | 465 |

The compound of the present invention represented by the above formula (I) is useful as an adenosine receptor ($A_1$, $A_{2a}$, $A_{2b}$, or $A_3$ receptor) antagonist, particularly an $A_{2B}$ receptor antagonist. Test Examples showing the usefulness of the compound of the present invention as a medicament are shown below.

Test Example 1
Measurement of the Ability to Bind to Adenosine $A_1$ Receptor

A human adenosine $A_1$ receptor cDNA was expressed in excess in CHOK1 cells, and this membrane sample was added at a protein concentration of 66.7 μg/ml to, and suspended in, 20 mM HEPES buffer, pH 7.4 (10 mM $MgCl_2$, 100 mM NaCl). To 0.45 ml of this membrane sample suspension were added 0.025 ml of 60 nM tritium-labeled chlorocyclopentyl adenosine ($^3$H—CCPA, from NEN Ltd.) and 0.025 ml test compound. This mixture was left at 30° C. for 120 minutes, filtered rapidly under suction through a glass fiber filter (GF/B, from Whatman), and immediately washed twice with 5 ml of 50 mM water-cooled Tris-HCl buffer. Thereafter, the glass fiber filter was transferred to a vial, a scintillator was added thereto, and the radioactivity on the filter was measured by a liquid scintillation counter. The inhibition of binding of $^3$H—CCPA to $A_1$ receptor by the test compound was determined using the following formula, and from this inhibition, 50% inhibition concentration ($IC_{50}$) was calculated (the following equation).

Inhibition (%)=[1−{binding in the presence of the test compound−non-specific binding)/(total binding−non-specific binding)}]×100

In the above formula, the total binding means $^3$H—CCPA-bound radioactivity in the absence of the test compound; the non-specific binding means $^3$H—CCPA-bound radioactivity in the presence of 100 μM RPIA ([R]-[1-methyl-2-phenylethyl] adenosine); and the binding in the presence of the test compound means $^3$H—CCPA-bound radioactivity in the presence of the test compound at predetermined concentrations. The inhibition constant (Ki value) in the table was determined from the formula of Cheng-Prusoff.

Test Example 2
Measurement of the Ability to Bind to Adenosine $A_{2a}$ Receptor An experiment of inhibition of binding to adenosine $A_{2a}$ receptor was conducted using a membrane sample (Receptor Biology Inc.) where an adenosine $A_{2a}$ receptor cDNA was expressed in excess. This membrane sample was added at a protein concentration of 22.2 μg/ml to, and suspended in, 20 mM HEPES buffer, pH 7.4 (10 mM $MgCl_2$ and 100 mM NaCl). To 0.45 ml of this membrane sample suspension were added 0.025 ml of 500 nM tritium-labeled 2-p-[2-carboxyethyl]phenetylamino-5'-N-ethylarboxyamide adenosine ($^3$H—CGS21680, from NEN) and 0.025 ml test compound. This mixture was left at 25° C. for 90 minutes, filtered rapidly under suction through a glass fiber filter (GF/B, from Whatman), and immediately washed twice with 5 ml of 50 mM water-cooled Tris-HCl buffer. Thereafter, the glass fiber filter was transferred to a vial, a scintillator was added thereto, and the radioactivity on the filter was measured by a liquid scintillation counter. The inhibition of binding of $^3$H—CGS21680 to $A_{2a}$ receptor by the test compound was determined using the following formula, and from this inhibition, 50% inhibition concentration ($IC_{50}$) was calculated.

Inhibition (%)=[1−{binding in the presence of the test compound−nonspecific binding)/(total binding−nonspecific binding)}]×100

Here, the total binding means $^3$H—CGS21680-bound radioactivity in the absence of the test compound; the nonspecific binding means $^3$H—CGS21680-bound radioactivity in the presence of 100 μM RPIA; and the binding in the presence of the test compound means $^3$H—CGS21680-bound radioactivity in the absence of the test compound at predetermined concentrations. The inhibition constant (Ki value) in the table was determined from the formula of Cheng-Prusoff.

Test Example 3
Experiment of Inhibition of NECA-stimulated Production of cAMP in Adenosine $A_{2b}$ Receptor-expressing Cells CHOK1 cells where a human adenosine $A_{2b}$ receptor had been expressed in excess were plated onto a 24-well plate at a density of 1.5×10$^5$ cells/well, cultured overnight, and used in the experiment. The degree of inhibitory effect of the test compound on the amount of cAMP produced by stimulation with 30 nM 5'-N-ethylcarboxyamide adenosine (NECA from Sigma) was evaluated in terms of affinity for $A_{2b}$ receptor. That is, the adhering cells were washed twice with 2 ml/well Krebs-Ringer buffer solution (containing 0.1% BSA; pH 7.4) and pre-incubated for 30 minutes in a volume of 0.5 ml/well. Then, a mixed solution containing NECA and the test compound was added in a volume of 0.1 ml/well in the presence of a phosphodiesterase inhibitor Ro-20-1724 (a product of RBI). After pre-incubation for 15 minutes, the reaction was terminated with 0.1 N HCl in a volume of 300 μl/well. Measurement of intracellular cAMP was carried out using a cAMP enzyme immunoassay kit produced by Amersham. The inhibition of NECA-stimulated production of cAMP by the test compound was determined using the following equation:

Inhibition (%)=[1−{(amount of cAMP in the coexistence of NECA and the test compound−amount of CAMP in only the Krebs-Ringer buffer solution)/(amount of CAMP upon stimulation with NECA only−amount of cAMP in only the Krebs-Ringer buffer solution)}]×100

The ability of the compound according to the present invention to bind to or the ability to inhibit adenosine receptor are as follows.

TABLE 1

| Test Compound | Ki (nM) A1 | Ki (nM) A2a | $IC_{50}$ (nM) A2b |
|---|---|---|---|
| Example 1 | 990 | 23 | 2.7 |
| 2 | 66 | 22 | 3.7 |
| 5 | 400 | 7 | 6.5 |

The compound according to the present invention or a salt thereof exhibited an excellent inhibitory activity on adenosine receptor.

Test Example 4
Evaluation of Defecation-Promoting Action

The defecation-promoting action of the adenosine $A_{2b}$ receptor-inhibiting compound which was identified by measuring the binding ability and inhibitory ability thereof to the adenosine receptor in Test Example 1, a salt thereof, a hydrate of them, or a pharmaceutical composition containing it can be evaluated on the basis of the following method. That is, SD IGS rats (6 weeks-old, from Charles River) were placed in cages (3 animals/cage) and preliminarily allowed food and water ad libitum and raised for 1 week. Then, a tared water-absorbing sheet was placed below each cage, and the animals were fasted but allowed water ad libitum throughout the experiment. After 1.5 hours, the fecal pellets were recovered from each cage and observed for abnormality before the experiment. The compound suspended or dissolved in 0.5% (w/v) methyl cellulose (MC) was orally administered in a dose of 5 ml/kg. On one hand, 0.5% (w/v) MC only was orally given to the control group. After administration of the compound, the rats were returned to the cage provided with a new water-absorbing sheet, and 90 minutes after the administration, the fecal pellets on the water-absorbing sheet were recovered from each cage, and the external appearance was observed, and then counted and weighed. The number of fecal pellets is expressed per each cage. After the fecal pellets were recovered, the water-absorbing sheet was weighed, and the weight determined by subtracting the initial weight of the water-adsorbing sheet from the weight after the experiment was regarded as the volume of urine.

TABLE 2

| Example | | The number of fecal pellets |
|---|---|---|
| Control | — | 0.50 ± 0.29 |
| 1 | 1 mg/kg | 1.75 ± 1.03 |
|   | 3 mg/kg | 7.25 ± 1.65 |
|   | 10 mg/kg | 22.25 ± 2.93 |
| 2 | 1 mg/kg | 7.80 ± 0.20 |
|   | 10 mg/kg | 18.00 ± 1.30 |
| 5 | 1 mg/kg | 7.00 ± 1.23 |
|   | 3 mg/kg | 14.25 ± 3.38 |

The compound according to the present invention or a salt thereof exhibited an excellent defecation-promoting action.

What is claimed is:

1. A compound represented by the formula:

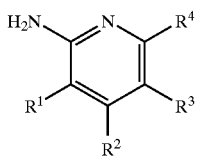

(I)

(wherein $R^1$ represents cyano group, carboxyl group or an optionally substituted carbamoyl group; $R^2$ represents hydrogen atom, hydroxyl group, an optionally substituted $C_{1-6}$ alkoxy group, an optionally substituted $C_{6-14}$ aromatic hydrocarbon cyclic group or an optionally substituted 5- to 14-membered aromatic heterocyclic group; and $R^3$ and $R^4$ are the same as or different from each other and each represents a $C_{3-8}$ cycloalkyl group, a $C_{3-8}$ cycloalkenyl group, a $C_{6-14}$ aromatic hydrocarbon cyclic group, a 5- to 14-membered non-aromatic heterocyclic group or a 5- to 14-membered aromatic heterocyclic group which may have a substituent group, respectively, provided that the cases where (1) $R^1$ is cyano group, $R^2$ is 4-bromo-2-thienyl group, $R^3$ is 3,4-dimethoxyphenyl group and $R^4$ is 2-thienyl group, (2) $R^1$ is cyano group, $R^2$ is hydrogen atom, and each of $R^3$ and $R^4$ is phenyl group, (3) $R^1$ is cyano group, $R^2$ is 4-chlorophenyl group, $R^3$ is phenyl group and $R^4$ is 4-(3,4-dichlorophenyl)-1-oxo-2(1H)-phthalazinyl group, (4) $R^1$ is cyano group, $R^2$ is hydrogen atom, $R^3$ is 4-pyridyl group and $R^4$ is 1-piperazinyl group, (5) $R^1$ is cyano group, $R^2$ is hydrogen atom, $R^3$ is 4-pyridyl group and $R^4$ is a 1-pyridyl group, (6) $R^1$ is cyano group, $R^2$ is hydrogen atom, $R^3$ is 4-pyridyl group and $R^4$ is 4-diphenylmethyl-1-piperazinyl group, (7) $R^1$ is cyano group, $R^2$ is hydrogen atom, $R^3$ is 4-pyridyl group and $R^4$ is 4-morpholinyl group, (8) $R^1$ is cyano group, $R^2$ is 4-methylphenyl group, and each of $R^3$ and $R^4$ is phenyl group and (9) $R^1$ is cyano group, and each of $R^2$, $R^3$ and $R^4$ is phenyl group are excluded) or a salt thereof.

2. The compound according to claim 1 or a salt thereof, in which $R^1$ is cyano group.

3. The compound according to claim 1 or a salt thereof, in which $R^1$ is a carbamoyl group represented by the formula:

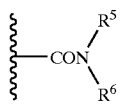

wherein $R^5$ and $R^6$ are the same as or different from each other and each represents hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group or an optionally substituted 5- to 14-membered aromatic heterocyclic group.

4. The compound according to claim 1 or a salt thereof, in which $R^2$ is a $C_{6-14}$ aromatic hydrocarbon cyclic group or 5- to 14-membered aromatic heterocyclic group, each of which may have a substituent group.

5. The compound according to claim 1 or a salt thereof, in which $R^2$ is a phenyl group, naphthyl group, pyridyl group, thienyl group or furyl group, each of which may have a substituent group.

6. The compound according to claim 1 or a salt thereof, in which $R^2$ is a phenyl group which may be substituted with a halogen atom.

7. The compound according to claim 1 or a salt thereof, in which $R^2$ is hydrogen atom.

8. The compound according to claim 1 or a salt thereof, in which $R^3$ and $R^4$ are the same as or different from each other and each represents a $C_{6-14}$ aromatic hydrocarbon cyclic group or a 5- to 14-membered aromatic heterocyclic group, each of which may have a substituent group.

9. The compound according to claim 1 or a salt thereof, in which $R^3$ and $R^4$ are the same as or different from each other and each represents a phenyl group, pyrrolyl group, pyridinyl group, pyridazinyl group, pyrimidinyl group, pyrazinyl group, thienyl group, thiazolyl group, furyl group, naphthyl group, quinolinyl group, isoquinolinyl group, phthalazinyl group, naphthyridinyl group, indolyl group or isoindolyl group, each of which may have a substituent group.

10. The compound according to claim 1 or a salt thereof, in which each of $R^3$ and $R^4$ represents a phenyl group, pyridyl group, thienyl group or furyl group which may have a substituent group, respectively.

11. The compound according to claim 1 or a salt thereof, in which $R^3$ and/or $R^4$ represent a 5- to 14-membered non-aromatic heterocyclic group, a $C_{6-14}$ aromatic hydrocarbon cyclic group or a 5- to 14-membered aromatic heterocyclic group, each of which may be substituted with at least one group selected from the following substituent group a, <substituent group a> a group consisting of (1) hydroxyl group, (2) a halogen atom, (3) cyano group, (4) nitro group, (5) a $C_{1-6}$ alkyl group, $C_{2-6}$ alkenyl group or $C_{2-6}$ alkynyl group, each of which may be substituted with at least one group selected from (i) hydroxyl group, (ii) cyano group, (iii) halogen atom, (iv) $C_{1-6}$ alkylamino group, (v) di($C_{1-6}$ alkyl)amino group, (vi) $C_{2-6}$ alkenylamino group, (vii) di($C_{2-6}$ alkenyl)amino group, (viii) $C_{2-6}$ alkynylamino group, (ix) di($C_{2-6}$ alkynyl)amino group, (x) N—$C_{1-6}$ alkyl-N—$C_{2-6}$ alkenylamino group, (xi) N—$C_{1-6}$ alkyl-N—$C_{2-6}$ alkynylamino group, (xii) N—$C_{2-6}$ alkenyl-N—$C_{2-6}$ alkynylamino group, (xiii) aralkyloxy group, (xiv) TBDMS oxy group, (xv) $C_{1-6}$ alkylsulfonylamino group, (xvi) $C_{1-6}$ alkylcarbonyloxy group, (xvii) $C_{2-6}$ alkenylcarbonyloxy group, (xviii) $C_{2-6}$ alkynylcarbonyloxy group, (xix) N—$C_{1-6}$ alkylcarbamoyl group, (xx) N—$C_{2-6}$ alkenylcarbamoyl group and (xxi) N—$C_{1-6}$ alkynylcarbamoyl group, (6) a $C_{1-6}$ alkoxy group, $C_{2-6}$ alkenyloxy group or $C_{2-6}$ alkynyloxy group, each of which may be substituted with at least one group selected from (i) $C_{1-6}$ alkylamino group, (ii) aralkyloxy group and (iii) hydroxyl group, (7) a $C_{1-6}$ alkylthio group, $C_{2-6}$ alkenylthio group or $C_{2-6}$ alkynylthio group, each of which may be substituted with at least one group selected from (i) hydroxyl group, (ii) nitrile group, (iii) halogen atom, (iv) $C_{1-6}$ alkylamino group, (v) aralkyloxy group, (vi) TBDMS oxy group, (vii) $C_{1-6}$ alkylsulfonylamino group, (viii) $C_{1-6}$ alkylcarbonyloxy group and (ix) alkylcarbamoyl group, (8) a carbonyl group substituted with a group selected from (i) $C_{1-6}$ alkoxy group, (ii) amino group, (iii) $C_{1-6}$ alkylamino group, (iv) di($C_{1-6}$ alkyl)amino group, (v) $C_{2-6}$ alkenylamino group, (vi) di($C_{2-6}$ alkenyl)amino group, (vii) $C_{2-6}$ alkynylamino group, (vii) di($C_{2-6}$ alkynyl)amino group, (viii) N—$C_{1-6}$ alkyl-N—$C_{2-6}$ alkenylamino group, (ix) N—$C_{1-6}$ alkyl-N—$C_{2-6}$ alkynylamino group and (x) N—$C_{2-6}$ alkenyl-N—$C_{2-6}$ alkynylamino group, (9) an amino group which may be substituted with one or two groups selected from (i) $C_{1-6}$ alkyl group, (ii) $C_{2-6}$ alkenyl group, (iii) $C_{2-6}$ alkynyl group, (iv) $C_{1-6}$ alkylsulfonyl group, (v) $C_{2-6}$ alkenylsulfonyl group, (vi) $C_{2-6}$ alkynylsulfonyl group, (vii) $C_{1-6}$ alkylcarbonyl group, (viii) $C_{2-6}$ alkenylcarbonyl group and (ix) $C_{2-6}$ alkynylcarbonyl group, (10) a $C_{1-6}$ alkylsulfonyl group, (11) a $C_{2-6}$ alkenylsulfonyl group, (12) a $C_{2-6}$ alkynylsulfonyl group, (13) a $C_{1-6}$ alkylsulfinyl group, (14) a $C_{2-6}$ alkenylsulfinyl group, (15) a $C_{2-6}$ alkynylsulfinyl group, (16) formyl group, (17) a $C_{3-8}$ cycloalkyl group or $C_{3-8}$ cycloalkenyl group, each of which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, (18) a 5- to 14-membered non-aromatic heterocyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, (19) a $C_{6-14}$ aromatic hydrocarbon cyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, and (20) a 5- to 14-membered aromatic heterocyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group.

12. The compound according to claim 1 or a salt thereof, in which $R^3$ and/or $R^4$ represent a phenyl group, pyridyl group, thienyl group or furyl group, each of which may be substituted with at least one group selected from hydroxyl group, a halogen atom, a $C_{1-6}$ alkyl group and a $C_{1-6}$ alkoxy group.

13. The compound according to claim 1 or a salt thereof, in which $R^3$ or $R^4$ is a 6-oxo-1,6-dihydropyridyl group which may have a substituent group.

14. The compound according to claim 1 represented by the formula:

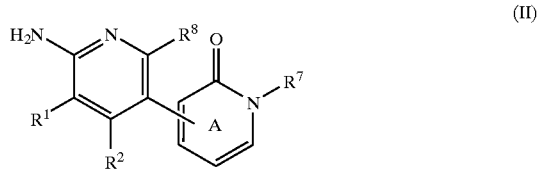

(II)

(wherein $R^1$ represents cyano group, carboxyl group or an optionally substituted carbamoyl group; $R^2$ represents hydrogen atom, hydroxyl group, an optionally substituted $C_{1-6}$ alkoxy group, an optionally substituted $C_{1-6}$ alkylthio group, an optionally substituted $C_{6-14}$ aromatic hydrocarbon cyclic group or an optionally substituted 5- to 14-membered aromatic heterocyclic group; $R^7$ represents a group selected from the following substituent group b; $R^8$ represents a $C_{6-14}$ aromatic hydrocarbon cyclic group or a 5- to 14-membered aromatic heterocyclic group which may have a substituent group, respectively; and ring A represents a nitrogen-containing 6-membered ring which may be substituted with 1 to 4 groups selected from the following substituent group b, <substituent group b> a group consisting of hydrogen atom, a halogen atom, hydroxyl group, nitro group, cyano group, an optionally substituted $C_{1-6}$ alkyl group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{2-6}$ alkenyloxy group, an optionally substituted $C_{2-6}$ alkynyloxy group, an optionally substituted $C_{1-6}$ alkylthio group, an optionally substituted $C_{2-6}$ alkenylthio group, an optionally substituted $C_{2-6}$ alkynylthio group, a $C_{2-7}$ fatty acyl group, an optionally substituted carbamoyl group, an arylacyl group, a heteroaryl acyl group, an optionally substituted amino group, an optionally substituted $C_{1-6}$ alkylsulfonyl group, an optionally substituted $C_{2-6}$ alkenylsulfonyl group, an optionally substituted $C_{2-6}$ alkynylsulfonyl group, an optionally substituted $C_{1-6}$ alkylsulfinyl group, an optionally substituted $C_{2-6}$ alkenylsulfinyl group, an optionally substituted $C_{2-6}$ alkynylsulfinyl group, formyl group, an optionally substituted $C_{3-8}$ cycloalkyl group, an optionally substituted $C_{3-8}$ cycloalkenyl group, an optionally substituted 5- to 14-membered non-aromatic heterocyclic group, an optionally substituted $C_{6-14}$ aromatic hydrocarbon cyclic group and an optionally substituted 5- to 14-membered aromatic heterocyclic group) or a salt thereof.

15. The compound according to claim 14 or a salt thereof, in which $R^1$ is cyano group.

16. The compound according to claim 14 or a salt thereof, in which $R^1$ is carboxyl group.

17. The compound according to claim 14 or a salt thereof, in which $R^1$ is a carbamoyl group represented by the formula:

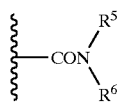

in which $R^5$ and $R^6$ have the same meanings as defined above.

18. The compound according to claim 14 or a salt thereof, in which $R^2$ is hydrogen atom.

19. The compound according to claim 1 represented by the formula:

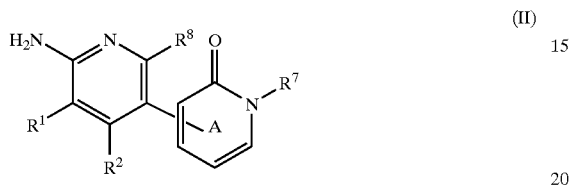

(II)

(wherein $R^1$ represents cyano group, carboxyl group or an optionally substituted carbamoyl group; $R^2$ represents hydrogen atom, hydroxyl group, an optionally substituted $C_{1-6}$ alkoxy group, an optionally substituted $C_{1-6}$ alkylthio group, an optionally substituted $C_{6-14}$ aromatic hydrocarbon cyclic group or an optionally substituted 5- to 14-membered aromatic heterocyclic group; $R^7$ represents a group selected from the following substituent group b; $R^8$ represents a $C_{6-14}$ aromatic hydrocarbon cyclic group or a 5- to 14-membered aromatic heterocyclic group which may have a substituent group, respectively; and ring A represents a nitrogen-containing 6-membered ring which may be substituted with 1 to 4 groups selected from the following substituent group a, <substituent group a> a group consisting of (1) hydroxyl group, (2) a halogen atom, (3) cyano group, (4) nitro group, (5) a $C_{1-6}$ alkyl group, $C_{2-6}$ alkenyl group or $C_{2-6}$ alkynyl group, each of which may be substituted with at least one group selected from (i) hydroxyl group, (ii) cyano group, (iii) halogen atom, (iv) $C_{1-6}$ alkylamino group, (v) di($C_{1-6}$ alkyl)amino group, (vi) $C_{2-6}$ alkenylamino group, (vii) di($C_{2-6}$ alkenyl)amino group, (viii) $C_{2-6}$ alkynylamino group, (ix) di($C_{2-6}$ alkynyl)amino group, (x) N—$C_{1-6}$ alkyl-N—$C_{2-6}$ alkenylamino group, (xi) N—$C_{1-6}$ alkyl-N—$C_{2-6}$ alkynylamino group, (xii) N—$C_{2-6}$ alkenyl-N—$C_{2-6}$ alkynylamino group, (xiii) aralkyloxy group, (xiv) TBDMS oxy group, (xv) $C_{1-6}$ alkylsulfonylamino group, (xvi) $C_{1-6}$ alkylcarbonyloxy group, (xvii) $C_{2-6}$ alkenylcarbonyloxy group, (xviii) $C_{2-6}$ alkynylcarbonyloxy group, (xix) N—$C_{1-6}$ alkylcarbamoyl group, (xx) N—$C_{2-6}$ alkenylcarbamoyl group and (xxi) N—$C_{1-6}$ alkynylcarbamoyl group, (6) a $C_{1-6}$ alkoxy group, $C_{2-6}$ alkenyloxy group or $C_{2-6}$ alkynyloxy group, each of which may be substituted with at least one group selected from (i) $C_{1-6}$ alkylamino group, (ii) aralkyloxy group and (iii) hydroxyl group, (7) a $C_{1-6}$ alkylthio group, $C_{2-6}$ alkenylthio group or $C_{2-6}$ alkynylthio group, each of which may be substituted with at least one group selected from (i) hydroxyl group, (ii) nitrile group, (iii) halogen atom, (iv) $C_{1-6}$ alkylamino group, (v) aralkyloxy group, (vi) TBDMS oxy group, (vii) $C_{1-6}$ alkylsulfonylamino group, (viii) $C_{1-6}$ alkylcarbonyloxy group and (ix) $C_{1-6}$ alkylcarbamoyl group, (8) a carbonyl group substituted with a group selected from (i) $C_{1-6}$ alkoxy group, (ii) amino group, (iii) $C_{1-6}$ alkylamino group, (iv) di($C_{1-6}$ alkyl)amino group, (v) $C_{2-6}$ alkenylamino group, (vi) di($C_{2-6}$ alkenyl)amino group, (vii) $C_{2-6}$ alkynylamino group, (vii) di($C_{2-6}$ alkynyl)amino group, (viii) N—$C_{1-6}$ alkyl-N—$C_{2-6}$ alkenylamino group, (ix) N—$C_{1-6}$ alkyl-N—$C_{2-6}$ alkynylamino group and (x) N—$C_{2-6}$ alkenyl-N—$C_{2-6}$ alkynylamino group, (9) an amino group which may be substituted with one or two groups selected from (i) $C_{1-6}$ alkyl group, (ii) $C_{2-6}$ alkenyl group, (iii) $C_{2-6}$ alkynyl group, (iv) $C_{1-6}$ alkylsulfonyl group, (v) $C_{2-6}$ alkenylsulfonyl), group, (vi) $C_{2-6}$ alkynylsulfonyl group, (vii) $C_{1-6}$ alkylcarbonyl group, (viii) $C_{2-6}$ alkenylcarbonyl group and (ix) $C_{2-6}$ alkynylcarbonyl group, (10) a $C_{1-6}$ alkylsulfonyl group, (11) a $C_{2-6}$ alkenylsulfonyl group, (12) a $C_{1-6}$ alkynylsulfonyl group, (13) a $C_{1-6}$ alkylsulfinyl group, (14) a $C_{2-6}$ alkenylsulfinyl group, (15) a $C_{2-6}$ alkynylsulfinyl group, (16) formyl group, (17) a $C_{3-8}$ cycloalkyl group or $C_{3-8}$ cycloalkenyl group, each of which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, (18) a 5- to 14-membered non-aromatic heterocyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, (19) a $C_{6-14}$ aromatic hydrocarbon cyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, and (20) a 5- to 14-membered aromatic heterocyclic group which may be substituted with at least one group selected from (i) hydroxyl group, (ii) halogen atom, (iii) nitrile group, (iv) $C_{1-6}$ alkyl group, (v) $C_{1-6}$ alkoxy group, (vi) $C_{1-6}$ alkoxy-$C_{1-6}$ alkyl group and (vii) aralkyl group, or a salt thereof.

20. The compound according to claim 14 or a salt thereof, in which $R^7$ is hydrogen atom, an optionally substituted $C_{1-6}$ alkyl group, an optionally substituted $C_{2-6}$ alkenyl group or an optionally substituted $C_{1-6}$ alkoxy group.

21. The compound according to claim 14 or a salt thereof, in which $R^8$ is a phenyl group, pyridyl group, furyl group or a thienyl group, each of which may have a substituent group.

22. The compound according to claim 14 or a salt thereof, in which $R^8$ is a phenyl group, pyridyl group, furyl group or a thienyl group, each of which may be substituted with a halogen atom.

23. The compound according to claim 1, in which the compound is any one selected from 2-amino-6-(2-furyl)-5-(4-pyridyl)-3-pyridinecarbonitrile, 2-amino-6-(3-fluorophenyl)-5-(4-pyridyl)-3-pyridinecarbonitrile, 2-amino-6-(2-furyl)-5-(4-methoxy-3-pyridyl)-3-pyridinecarbonitrile, 2-amino-6-(2-furyl)-5-(6-oxo-1,6-dihydro-3-pyridinyl)nicotinonitrile, 2-amino-5-(1-ethyl-6-oxo-1,6-dihydro-3-pyridinyl)-6-(2-furyl)nicotinonitrile, 2-amino-6-(2-furyl)-5-(1-methyl-6-oxo-1,6-dihydro-3-pyridinyl)nicotinonitrile, 2-amino--6-(3-fluorophenyl)-5-(6-oxo-1,6-dihydro-3-pyridinyl)nicotinonitrile and 2-amino-6-(3-fluorophenyl)-5-(1-methyl-6-oxo-1,6-dihydro-3-pyridinyl)nicotinonitrile, or a salt thereof.

24. A pharmaceutical composition comprising a compound represented by the formula:

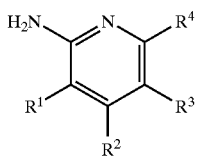
(I)

(wherein $R^1$ represents cyano group, carboxyl group or an optionally substituted carbamoyl group; $R^2$ represents hydrogen atom, hydroxyl group, an optionally substituted $C_{1-6}$ alkoxy group, an optionally substituted $C_{6-14}$ aromatic hydrocarbon cyclic group or an optionally substituted 5- to 14-membered aromatic heterocyclic group; and $R^3$ and $R^4$ are the same as or different from each other and each represents a $C_{3-8}$ cycloalkyl group, a $C_{3-8}$ cycloalkenyl group, a $C_{6-14}$ aromatic hydrocarbon cyclic group, a 5- to 14-membered non-aromatic heterocyclic group or a 5- to 14-membered aromatic heterocyclic group which may have a substituent group, respectively, provided that the cases where (1) $R^1$ is cyano group, $R^2$ is 4-bromo-2-thienyl group, $R^3$ is 3,4-dimethoxyphenyl group and $R^4$ is 2-thienyl group, (2) $R^1$ is cyano group, $R^2$ is hydrogen atom and each of $R^3$ and $R^4$ is phenyl group, (3) $R^1$ is cyano group, $R^2$ is 4-chloro-phenyl group, $R^3$ is phenyl group and $R^4$ is 4-(3,4-dichlorophenyl)-1-oxo-2(1H)-phthalazinyl group, (4) $R^1$ is cyano group, $R^2$ is hydrogen atom, $R^3$ is 4-pyridyl group and $R^4$ is 1-piperazinyl group, (5) $R^1$ is cyano group, $R^2$ is hydrogen atom, $R^3$ is 4-pyridyl group and $R^4$ is 1-pyridyl group, (6) $R^1$ is cyano group, $R^2$ is hydrogen atom, $R^3$ is 4-pyridyl group and $R^4$ is 4-diphenylmethyl-1-Piperazinyl group, (7) $R^1$ is cyano group, $R^2$ is hydrogen atom, $R^3$ is 4-pyridyl group and $R^4$ is 4-morpholinyl group, (8) $R^1$ is cyano group, $R^2$ is 4-methylphenyl group and each of $R^3$ and $R^4$ is phenyl group, and (9) $R^1$ is cyano group and each of $R^2$, $R^3$ and $R^4$ is phenyl group are excluded) or a pharmacologically acceptable salt thereof and a pharmacologically acceptable carrier.

25. The composition according to claim 24, which is an agent for treating or preventing a disease to which an adenosine receptor relates.

26. The composition according to claim 24, which is an agent for treating or preventing a disease to which an adenosine $A_2$ receptor relates.

27. The composition according to claim 24, which is an agent for treating or preventing a disease to which an adenosine $A_{2B}$ receptor relates.

28. The composition according to claim 24, which is an adenosine receptor antagonist.

29. The composition according to claim 24, which is an adenosine $A_2$ receptor antagonist.

30. The composition according to claim 24, which is an adenosine $A_{2B}$ receptor antagonist.

31. The composition according to claim 24, which is used for promoting defecation.

32. The composition according to claim 24, which is an agent for treating, preventing or improving constipation.

33. The composition according to claim 24, in which the constipation is functional constipation.

34. The composition according to claim 24, which is an agent for treating irritable bowel syndrome, constipation accompanying irritable bowel syndrome, organic constipation, constipation accompanying enteroparalytic ileus, constipation accompanying congenital digestive tract dysfunction or constipation accompanying ileus.

35. The composition according to claim 24, which is used for evacuating intestinal tracts at the time of examination of digestive tracts or before and after an operation.

36. The composition according to claim 24, which is an agent for treating or preventing diabetes, diabetic complications, diabetic retinopathy, obesity or asthma.

37. The composition according to claim 24, which is a hypoglycemic agent, an improving agent for impaired glucose tolerance or a potentiating agent for insulin sensitivity.

38. The composition according to claim 24, which is a hypotensive agent, a diuretic, a therapeutic agent for osteoporosis, an anti-Parkinson's disease agent, an anti-Alzheimer's disease agent, a therapeutic agent for inflammatory intestinal diseases or a therapeutic agent for Crohn's disease.

39. A method of treating or preventing a disease to which an adenosine receptor relates, by administering a pharmacologically effective dose of the compound according to claim 1 or a pharmacologically acceptable salt thereof to a patient.

* * * * *